US011608328B2

(12) United States Patent
North et al.

(10) Patent No.: US 11,608,328 B2
(45) Date of Patent: Mar. 21, 2023

(54) CHEMICAL PROBES TO IDENTIFY ANTI-MYCOBACTERIAL MMPL3 INHIBITORS

(71) Applicants: Creighton University, Omaha, NE (US); Colorado State University Research Foundation, Fort Collins, CO (US)

(72) Inventors: E. Jeffrey North, Omaha, NE (US); Amitkumar Navinchandra Pandya, Omaha, NE (US); Mary C. Jackson, Fort Collins, CO (US); Wei Li, Fort Collins, CO (US); Mercedes Gonzalez-Juarrero, Fort Collins, CO (US)

(73) Assignees: Creighton University, Omaha, NE (US); Colorado State University Research Foundation, Fort Collins, CO (US)

( * ) Notice: Subject to any disclaimer, the term of this patent is extended or adjusted under 35 U.S.C. 154(b) by 238 days.

(21) Appl. No.: 16/797,744

(22) Filed: Feb. 21, 2020

(65) Prior Publication Data
US 2020/0331897 A1 Oct. 22, 2020

Related U.S. Application Data

(60) Provisional application No. 62/808,469, filed on Feb. 21, 2019.

(51) Int. Cl.
C07D 405/14 (2006.01)
C07F 5/02 (2006.01)
G01N 33/50 (2006.01)

(52) U.S. Cl.
CPC ............ *C07D 405/14* (2013.01); *C07F 5/022* (2013.01); *G01N 33/502* (2013.01)

(58) Field of Classification Search
None
See application file for complete search history.

(56) References Cited

PUBLICATIONS

Li et al., Direct Inhibition of MmpL3 by Novel Antitubercular Compounds. ACS Infectious Diseases, May 2019, 1001-1012.*
Koch et al., Imaging of Tie2 with a Fluorescently Labeled Small Molecule Affinity Ligand. ACS Chemical Biology, 2020, 15, 151-157 (published on Dec. 6, 2019).*
Grant & Hackh's Chemical Dictionary (5th Ed. 1987) at p. 148.*
Belardinelli et al., "Structure-function profile of MmpL3, the essential mycolic acid transporter from *Mycobacterium tuberculosis*," ACS Infectious Diseases, Oct. 14, 2016, 2(10):702-13.
Brown et al., "The structure-activity relationship of urea derivatives as anti-tuberculosis agents," Bioorganic & Medicinal Chemistry, Sep. 15, 2011, 19(18):5585-95.

Carel et al., "*Mycobacterium tuberculosis* proteins involved in mycolic acid synthesis and transport localize dynamically to the old growing pole and septum," PLoS One, May 2014, 9(5), https://doi.org/10.1371/journal.pone.0097148, 15 pages.
Cox Jet al., "THPP target assignment reveals EchA6 as an essential fatty acid shuttle in mycobacteria," Nature Microbiology, Jan. 18, 2016, 1(2), 10 pages.
De Groote et al., "Optimization and lead selection of benzothiazole amide analogs toward a novel antimycobacterial agent," Frontiers in Microbiology, Sep. 20, 2018, 9:2231, 10 pages.
Degiacomi et al., "Essentiality of mmpL3 and impact of its silencing on *Mycobacterium tuberculosis* gene expression," Scientific Reports, Feb. 27, 2017, 7:43495, 8 pages.
Feng et al., "Antiinfectives targeting enzymes and the proton motive force," Proceedings of the National Academy of Sciences, Dec. 22, 2015, 112(51):E7073-82.
Foss et al., "Diphenylether-modified 1, 2-diamines with improved drug properties for development against *Mycobacterium tuberculosis*," ACS Infectious Diseases, Jul. 8, 2016, 2(7):500-8.
Franz et al., "Design, synthesis and evaluation of indole-2-carboxamides with pan anti-mycobacterial activity," Bioorganic & Medicinal Chemistry, Jul. 15, 2017, 25(14):3746-55.
Goldman, "Why are membrane targets discovered by phenotypic screens and genome sequencing in *Mycobacterium tuberculosis*?," Tuberculosis, Nov. 1, 2013, 93(6):569-88.
Grzegorzewicz et al, "Inhibition of mycolic acid transport across the *Mycobacterium tuberculosis* plasma membrane," Nat. Chem. Biol. 2012, 8:334-341.
Kozikowski et al, "Targeting Mycolic Acid Transport by Indole-2-carboxamides for the Treatment of *Mycobacterium abscessus* Infections," J. Med. Chem. 2017, 60:5876-5888.
La Rosa et al, "MmpL3 Is the Cellular Target of the Antitubercular Pyrrole Derivative BM212," Antimicrob. Agents Chemother, 2012, 56:324-331.
Li et al, "Therapeutic Potential of the *Mycobacterium tuberculosis* Mycolic Acid Transporter, MmpL3," Antimicrob. Agents Chemother. 2016, 60(9):5198-5207.
Li et al, "MmpL3 as a Target for the Treatment of Drug-Resistant Nontuberculous Mycobacterial Infections," Front Microbiol. 2018, 9:1547.
Li et al, "Multitarget Drug Discovery for Tuberculosis and Other Infectious Diseases," J. Med. Chem. 2014, 57(7):3126-3139.
Li et al, "Novel Insights into the Mechanism of Inhibition of MmpL3, a Target of Multiple Pharmacophores in *Mycobacterium tuberculosis*," Antimicrob. Agents Chemother. 2014, 58(11):6413-6423.
Li, et al, "Synergistic interactions of MmpL3 inhibitors with anti-tubercular compounds in vitro," Antimicrob. Agents Chemother. 2017, 61(4):e02399-16.
Lun et al. "Indoleamides are active against drug-resistant *Mycobacterium tuberculosis*," Nat. Commun. 2013, 4:2907.
Martin et al, "Resazurin Microtiter Assay Plate Testing of *Mycobacterium tuberculosis* Susceptibilities to Second-Line Drugs: Rapid, Simple, and Inexpensive Method," Antimicrob. Agents Chemother, 2003, 47(11):3616-3619.

(Continued)

*Primary Examiner* — Po-Chih Chen
(74) *Attorney, Agent, or Firm* — Fish & Richardson P.C.

(57) ABSTRACT

The present application provides detectable compounds useful for identifying compounds that bind (e.g., inhibit) MmpL3. Methods of identifying compounds that bind and/or inhibit MmpL3 are also provided.

17 Claims, 24 Drawing Sheets

Specification includes a Sequence Listing.

(56) References Cited

PUBLICATIONS

McNeil et al, "Mutations in MmpL3 alter membrane potential, hydrophobicity and antibiotic susceptibility in *Mycobacterium smegmatis*," Microbiology, 2017, 163(7):1065-1070.

Onajole et al., "Preliminary Structure-Activity Relationships and Biological Evaluation of Novel Antitubercular Indolecarboxamide Derivatives Against Drug-Susceptible and Drug-Resistant *Mycobacterium tuberculosis* Strains," J. Med. Chem. 2013, 56(10): 4093-4103.

Pandya et al., "Indole-2-carboxamides are active against *Mycobacterium abscessus* in a mouse model of acute infection," Antimicrobial Agents and Chemotherapy, Mar. 1, 2019, 63(3).

Rao et al., "Indolcarboxamide is a preclinical candidate for treating multidrug-resistant tuberculosis," Science translational medicine, Dec. 4, 2013, 5(214): 11 Pages.

Remuiñán et al., "Tetrahydropyrazolo [1, 5-a] pyrimidine-3-carboxamide and N-benzyl-6', 7'-dihydrospiro [piperidine-4, 4'-thieno [3, 2-c] pyran] analogues with bactericidal efficacy against *Mycobacterium tuberculosis* targeting MmpL3," PloS one, Apr. 17, 2013, 8(4):e60933, 1-10.

Sacksteder et al., "Discovery and development of SQ109: a new antitubercular drug with a novel mechanism of action," Future microbiology, Jul. 2012, 7(7):823-837.

Stanley et al., "Identification of novel inhibitors of M. tuberculosis growth using whole cell based high-throughput screening," ACS chemical biology, Aug. 17, 2012, 7(8):1377-1384.

Stec et al., "Indole-2-carboxamide-based MmpL3 inhibitors show exceptional antitubercular activity in an animal model of tuberculosis infection," Journal of medicinal chemistry, Jul. 14, 2016, 59(13):6232-6247.

Tahlan et al., "SQ109 targets MmpL3, a membrane transporter of trehalose monomycolate involved in mycolic acid donation to the cell wall core of *Mycobacterium tuberculosis*," Antimicrobial agents and chemotherapy, Apr. 1, 2012, 56(4):1797-1809.

Tantry et al., "Whole cell screen based identification of spiropiperidines with potent antitubercular properties," Bioorganic & medicinal chemistry letters, Aug. 15, 2015, 25(16): 13 Pages.

Tikhonova et al., "Kinetic control of TolC recruitment by multidrug efflux complexes," Proceedings of the National Academy of Sciences, Sep. 22, 2009, 106(38):16416-16421.

Xu et al., "MmpL3 is the flippase for mycolic acids in mycobacteria," Proceedings of the National Academy of Sciences, Jul. 25, 2017, 114(30):7993-7998.

Yokokawa et al., "Discovery of tetrahydropyrazolopyrimidine carboxamide derivatives as potent and orally active antitubercular agents," ACS medicinal chemistry letters, May 9, 2013, 4(5):451-455.

Zhang et al., "Crystal structures of membrane transporter MmpL3, an anti-TB drug target," Cell, Jan. 24, 2019, 176(3): 27 Pages.

* cited by examiner

CHEMICAL PROBES TO IDENTIFY ANTI-MYCOBACTERIAL MMPL3 INHIBITORS

CROSS-REFERENCE TO RELATED APPLICATIONS

This application claims the benefit of U.S. Provisional Application Ser. No. 62/808,469, filed Feb. 21, 2019, the disclosure of which is incorporated herein by reference in its entirety.

FEDERALLY SPONSORED RESEARCH OR DEVELOPMENT

This invention was made with Government support under Grant No. AI116525, awarded by the National Institutes of Health. The Government has certain rights in the invention.

TECHNICAL FIELD

The present application provides detectable compounds useful for identifying compounds that bind (e.g., inhibit) MmpL3.

BACKGROUND

MmpL3 is required for the translocation of mycolic acids in the form of trehalose monomycolates (TMM) from the cytoplasm to the periplasmic space where mycolic acids can then be used in the assembling of the mycobacterial outer membrane (see e.g., Grzegorzewicz et al, *Nat. Chem. Biol.*, 2012, 8:334-341; Tahlan et al, *Antimicrob. Agents Chemother.* 2012, 56:1797-1809; Li et al, *Antimicrob. Agents Chemother.* 2016, 60:5198-5207; and Belardinelli et al, *ACS Infect. Dis.* 2016, 2:702-713). The steep decrease in *Mycobacterium tuberculosis* (Mtb) viability that follows the chemical or genetic inhibition of MmpL3 in vitro, inside macrophages, and in acute and chronic mouse models of *tuberculosis* (TB) infection points to the vulnerability of this transporter (see e.g., Grzegorzewicz et al, *Nat. Chem. Biol.*, 2012, 8:334-341; Tahlan et al, *Antimicrob. Agents Chemother.* 2012, 56:1797-1809; Li et al, *Antimicrob. Agents Chemother.* 2016, 60:5198-5207; Stanley et al, *ACS Chem. Biol.* 2012, 7:1377-1384; Rao et al, *Sci. Transl. Med.* 2013, 5:214ra168; Lun et al. *Nat. Commun.* 2013, 4:2907; Remuinan et al. *PLoS ONE,* 2013, 8:e60933; Tantry et al, *Bioorg. Med. Chem. Lett.* 2015, 25:3234-3245; and Degiacomi et al, *Sci. Rep.* 2017, 7:43495).

SUMMARY

The present application provides, inter alia, a compound of Formula I:

A-B-C    I or a salt thereof, wherein:
A is a detectable moiety;
B is a linking group; and
C is an MmpL3 inhibitor moiety.

In some embodiments, A is a fluorescent detectable moiety. In some embodiments, the fluorescent detectable moiety comprises a xanthene moiety, an anthracene moiety, an anthraquinone moiety, an acridine moiety, or any combination thereof. In some embodiments, the fluorescent detectable moiety is selected from the group consisting of:

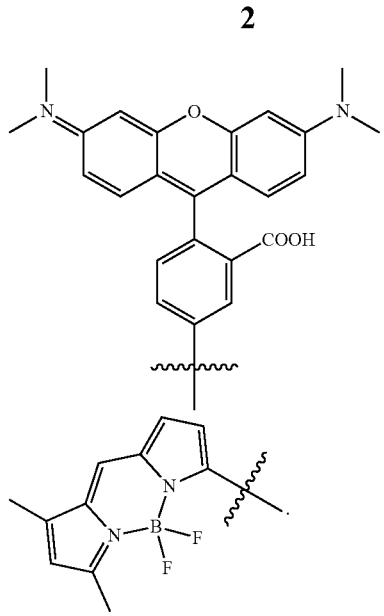

and wherein ∿∿∿ refers to the bond between A and B.

In some embodiments, B is a linking group comprising one or more alkylene groups, one or more C(O)NH groups, and one or more 5-10 membered heteroaryl rings. In some embodiments, B is a linking group comprising one or more $C_{1-10}$ alkylene groups, one or more C(O)NH groups, and one 5-10 membered heteroaryl ring. In some embodiments, B is a linking group comprising one, two, or three $C_{1-10}$ alkylene groups, one C(O)NH group, and one 5-6 membered heteroaryl ring.

In some embodiments, B is a linking group selected from the group consisting of:
—C(O)NH—($C_{1-10}$ alkylene)-(5-6 membered heteroaryl)-($C_{1-10}$ alkylene)-; and
—($C_{1-10}$ alkylene)-C(O)NH—($C_{1-10}$ alkylene)-(5-6 membered heteroaryl)-($C_{1-10}$ alkylene)-.

In some embodiments, B is a linking group selected from the group consisting of:
—C(O)NH—($C_{1-6}$ alkylene)-(5-6 membered heteroaryl)-($C_{1-3}$ alkylene)-; and
—($C_{1-3}$ alkylene)-C(O)NH—($C_{1-3}$ alkylene)-(5-6 membered heteroaryl)-($C_{1-3}$ alkylene)-. In some embodiments, the heteroaryl ring of group sB is a triazolyl ring.

In some embodiments, B is a linking group selected from the group consisting of:
—C(O)NHCH$_2$CH$_2$CH$_2$CH$_2$CH$_2$CH$_2$-triazolyl-CH$_2$—; and
—CH$_2$CH$_2$C(O)NHCH$_2$CH$_2$CH$_2$-triazolyl-CH$_2$—.

In some embodiments, C is an MmpL3 inhibitor moiety selected from the group consisting of:

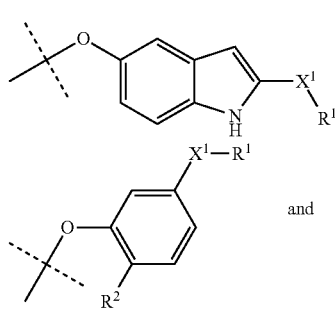

and

-continued

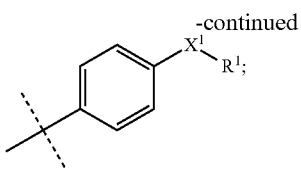

wherein:
- - - - - - refers to the bond between B and C;
$X^1$ is selected from the group consisting of C(O)NH, $C_{1-4}$ alkyl-C(O)NH, and NHC(O)NH; $R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups; and
$R^2$ is selected from the group consisting of C(O)$C_{1-4}$ alkyl and C(O)$C_{1-4}$ alkoxy.

In some embodiments, C is

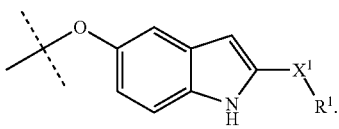

In some embodiments, C is

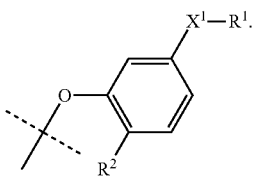

In some embodiments, C is

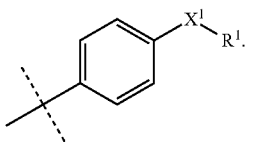

In some embodiments, $X^1$ is C(O)NH. In some embodiments, $X^1$ is NHC(O)NH.

In some embodiments, $R^1$ is $C_{5-10}$ cycloalkyl, which is optionally substituted by 1, 2, or 3 independently selected $C_{1-4}$ alkyl groups. In some embodiments, $R^1$ is selected from the group consisting of cyclooctyl, bicyclo[3.1.1]heptyl, and adamantyl, each of which is optionally substituted by 1, 2, or 3 methyl groups. In some embodiments, $R^1$ is selected from the group consisting of cyclooctyl, trimethylbicyclo [3.1.1]heptyl, and adamantyl. In some embodiments, $R^1$ is cyclooctyl.

In some embodiments, $R^2$ is C(O)$C_{1-4}$ alkoxy. In some embodiments, $R^2$ is C(O)OCH$_3$.

In some embodiments:
A is a fluorescent detectable moiety;
B is a linking group comprising one or more alkylene groups, one or more C(O)NH groups, and one or more 5-10 membered heteroaryl rings; and
C is an MmpL3 inhibitor moiety selected from the group consisting of:

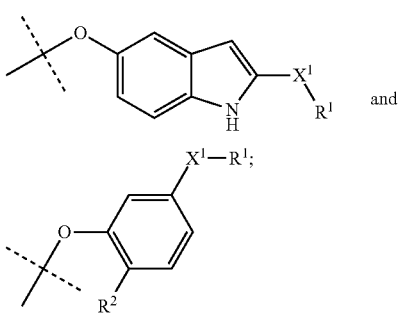

wherein:
- - - - - - refers to the bond between B and C;
$X^1$ is selected from the group consisting of C(O)NH and NHC(O)NH;
$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups; and
$R^2$ is selected from the group consisting of C(O)$C_{1-4}$ alkyl and C(O)$C_{1-4}$ alkoxy.

In some embodiments:
A is a fluorescent detectable moiety selected from the group consisting of:

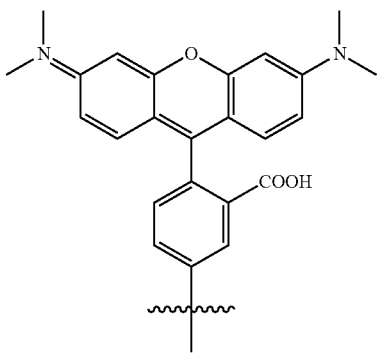

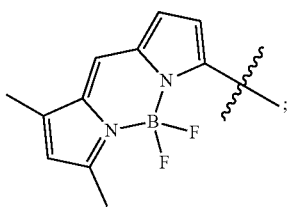

wherein ~~~~ refers to the bond between A and B;
B is a linking group comprising one or more $C_{1-10}$ alkylene groups, one or more C(O)NH groups, and one 5-6 membered heteroaryl ring; and
C is an MmpL3 inhibitor moiety selected from the group consisting of:

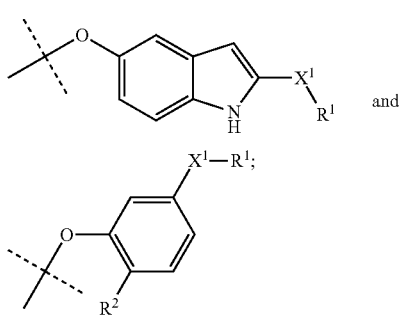 and wherein:

------ refers to the bond between B and C;

$X^1$ is selected from the group consisting of C(O)NH and NHC(O)NH;

$R^1$ is $C_{5-10}$cycloalkyl, which is optionally substituted by 1, 2, 3, or 4 independently selected $C_{1-4}$ alkyl groups; and $R^2$ is C(O)$C_{1-4}$ alkoxy.

In some embodiments:

A is a fluorescent detectable moiety selected from the group consisting of:

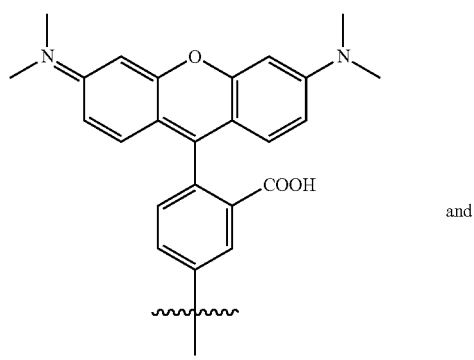

wherein ⁓⁓⁓ refers to the bond between A and B;

B is a linking group selected from the group consisting of —C(O)NH—($C_{1-6}$ alkylene)-(triazolyl)-($C_{1-3}$ alkylene)- and —($C_{1-3}$ alkylene)-C(O)NH—($C_{1-3}$ alkylene)-(triazolyl)-($C_{1-3}$ alkylene)-; and C is an MmpL3 inhibitor moiety selected from the group consisting of:

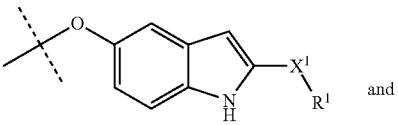 and

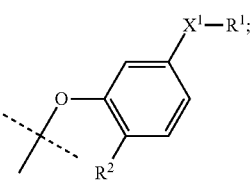

wherein:

------ refers to the bond between B and C;

$X^1$ is selected from the group consisting of C(O)NH and NHC(O)NH;

$R^1$ is selected from the group consisting of cyclooctyl, bicyclo[3.1.1]heptyl, and adamantyl, each of which is optionally substituted by 1, 2, or 3 methyl groups; and $R^2$ is C(O)OCH$_3$.

In some embodiments, the compound of Formula I is a compound of Formula II:

II

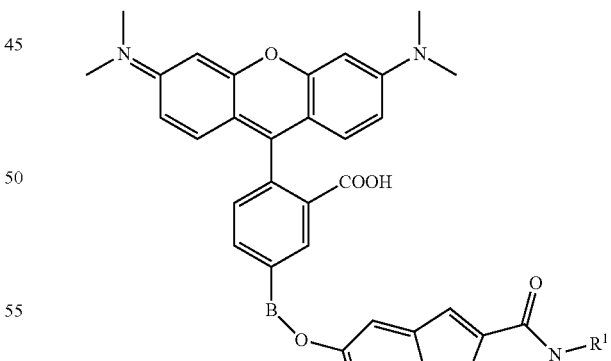

or a salt thereof.

In some embodiments, the compound of Formula I is a compound of Formula III:

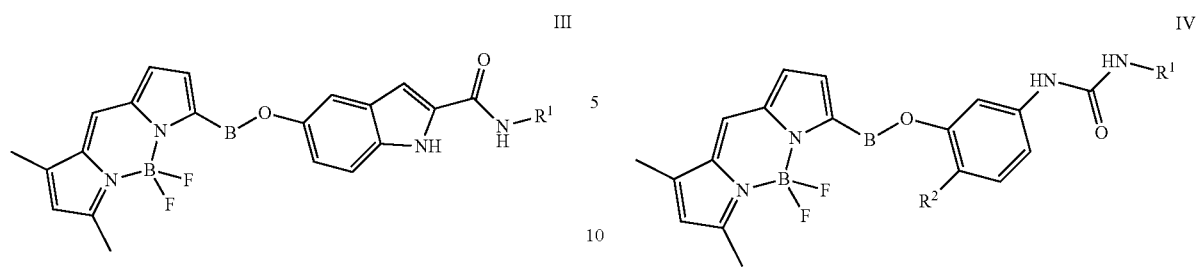
or a salt thereof.
In some embodiments, the compound of Formula I is a compound of Formula IV:
or a salt thereof.
In some embodiments, the compound provided herein is selected from the group consisting of:
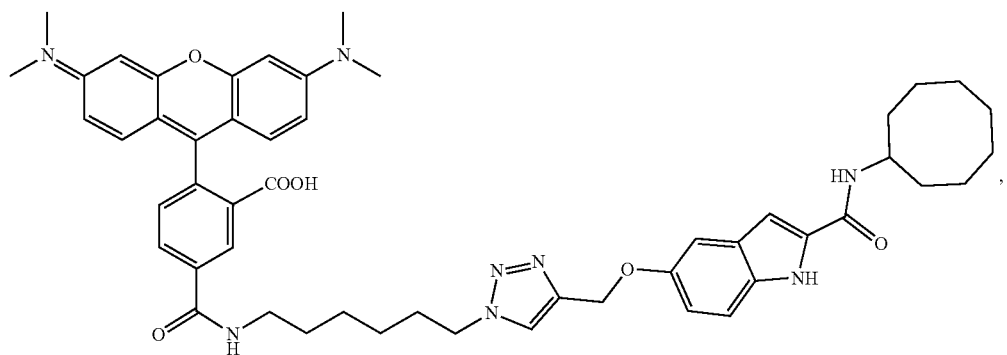
,
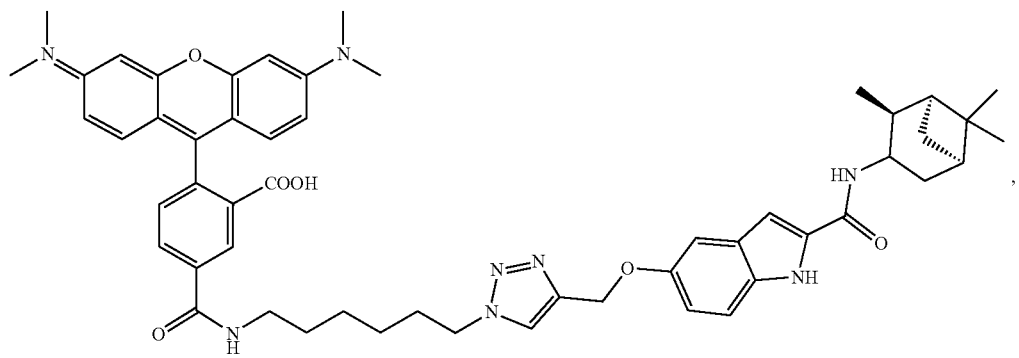
,
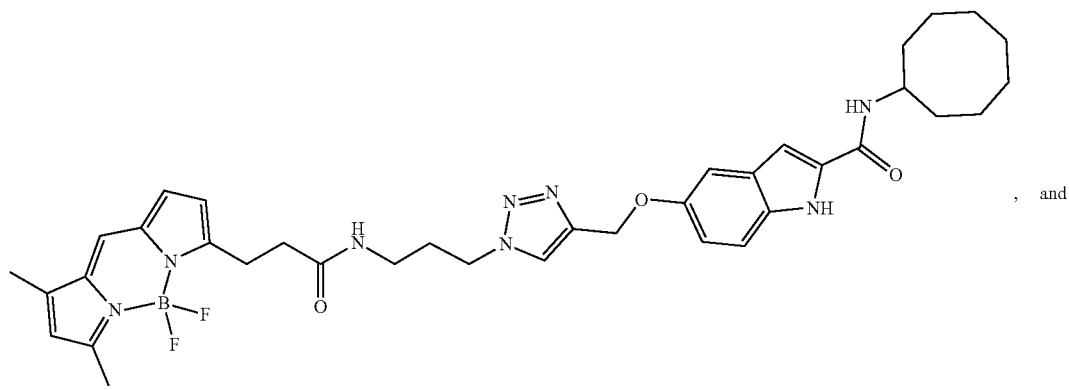
, and -continued

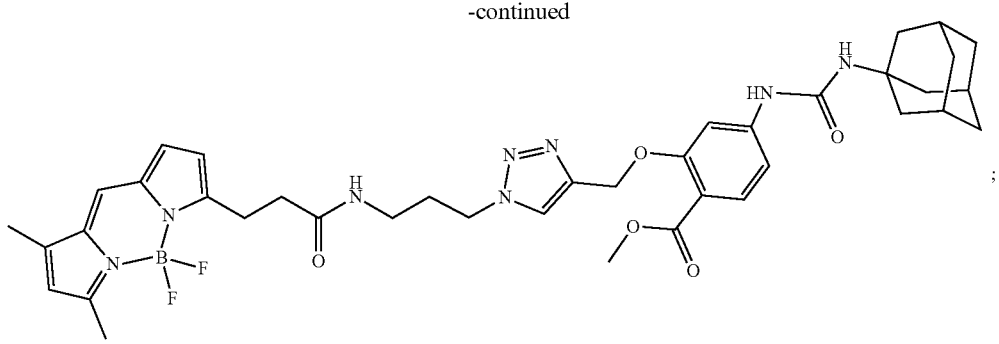

or a salt thereof.

The present application further provides a composition, comprising a compound provided herein (e.g., a compound of Formula I), or a salt thereof, and a carrier.

The present application further provides a method of identifying an inhibitor of MmpL3, comprising:

i) contacting a cell with a compound provided herein (e.g., a compound of Formula I), or a salt thereof, to form a compound-MmpL3 complex in the cell;

ii) contacting the cell with a test compound; and iii) measuring displacement of the compound from the compound-MmpL3 complex and formation of a test compound-MmpL3 complex in the cell.

In some embodiments, step i) and step ii) are performed simultaneously. In some embodiments, the displacement is measured by flow cytometry.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The SPR sensorgrams were fitted into different kinetic models and are shown along with the best fits.

Figure 6:
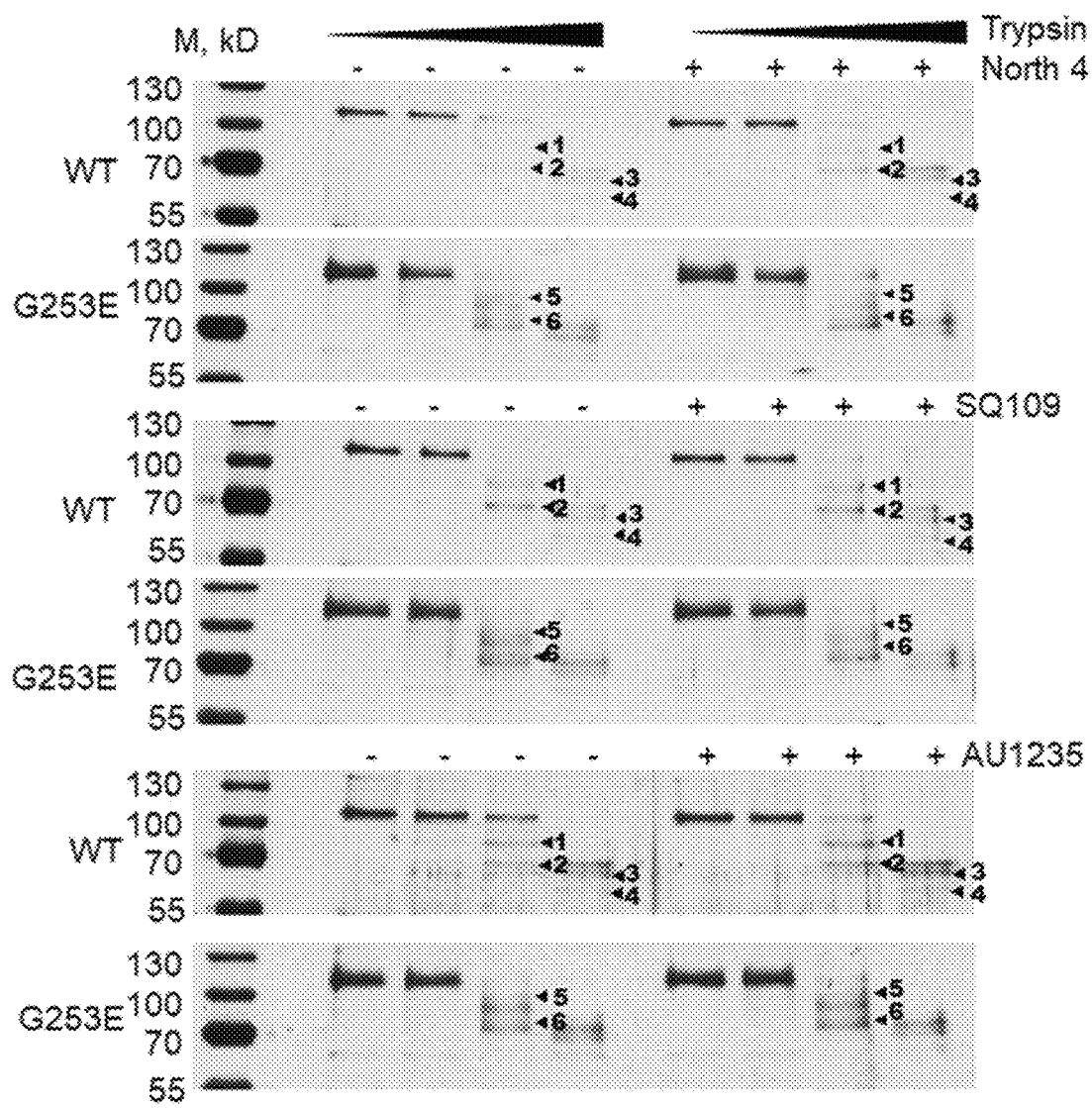

FIG. 6 shows proteolytic profiles of the wild-type MmpL3$^{WT}$ and its resistant variant MmpL3$^{G253E}$ in the presence and absence of inhibitors. Purified proteins (100 nM final concentrations) were incubated with increasing concentrations of trypsin (0.01, 0.1 and 1.0 µg/mL). Inhibitors were added where indicated to the final concentration of 200 µM prior to trypsin. The digest was carried out for 30 min at 37° C. and the tryptic fragments were separated by 12% SDS-PAGE followed by silver nitrate staining. The dominant bands are indicated by arrowheads.

Figure 7A:
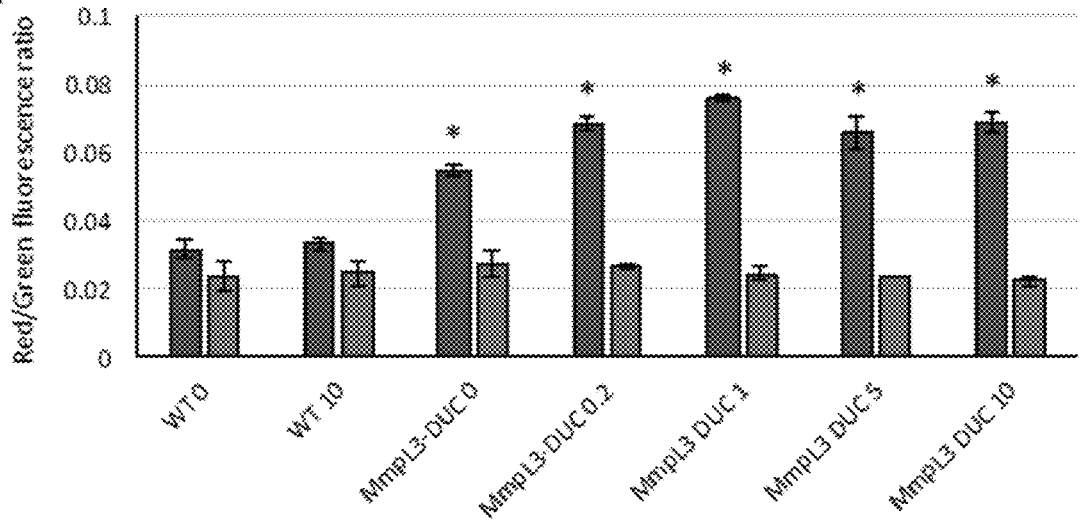
Figure 7B:
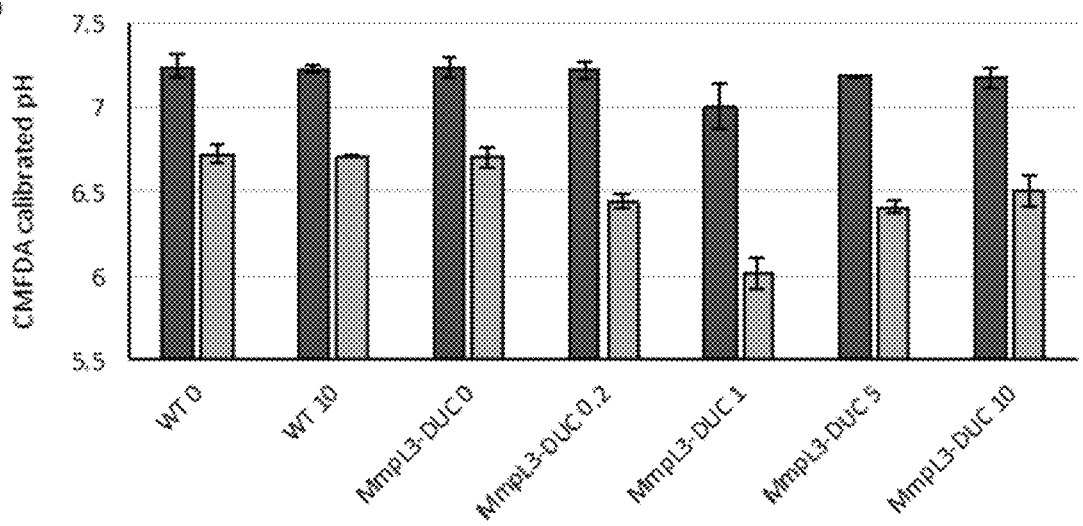

FIGS. 7A-7B show effects of silencing mmpL3 expression on the membrane potential ($\Delta\Psi$) and electrochemical proton gradient ($\Delta$pH) of Mtb. The $\Delta\Psi$ (FIG. 7A) and inner bacterial pH (FIG. 7B) of wild-type (WT) Mtb and mmpL3 knock-down (MmpL3-DUC) cells grown in the presence of 0, 0.2, 1, 5 or 10 ng/mL anhydro-tetracycline were determined. The expression of mmpL3 was previously shown to be inhibited in an anhydro-tetracycline concentration-dependent manner in the MmpL3-DUC knock-down strain (see e.g., Li et al, *Antimicrob. Agents Chemother.* 2016, 60:5198-5207). The values represent the averages and standard deviations of measurements performed on three independent bacterial suspensions after exposure to CCCP (4-times MIC; 25 µM) (right bars) or the DMSO solvent (1%) solvent alone (left bars) for 30 minutes at 37° C. Results are representative of two independent tests. Asterisks denote statistically significant differences between WT and DUC mutant cells as per the Student's t-test (P<0.05).

Figure 8A:
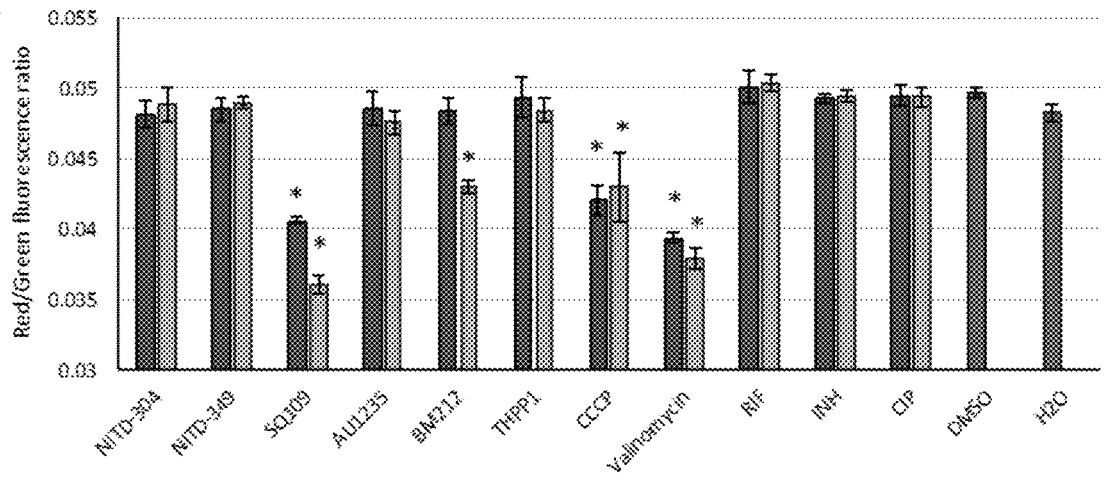
Figure 8B:
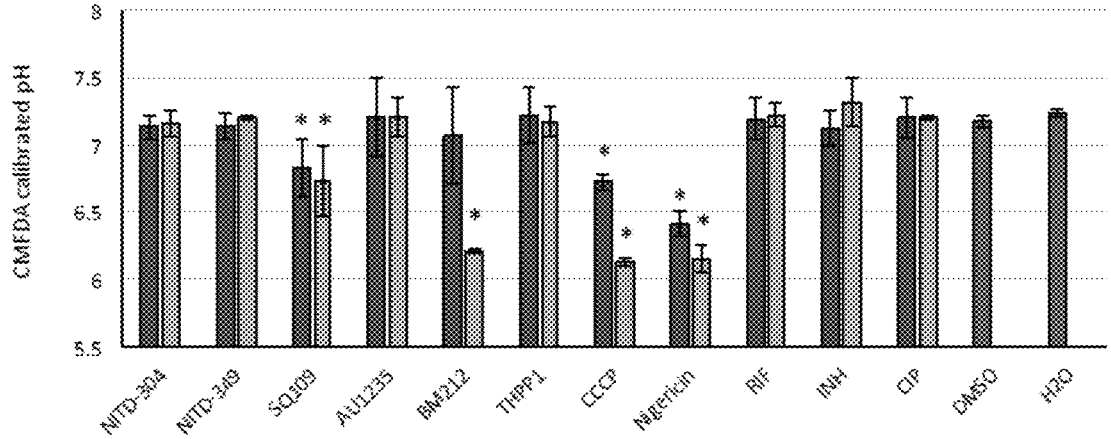

FIGS. 8A-8B show the effect of SQ109, BM212, THPP1, AU1235, NITD-304 and NITD-349 on the membrane potential ($\Delta\Psi$; FIG. 8A) and electrochemical proton gradient ($\Delta$pH; FIG. 8B) of intact Mtb bacilli. The $\Delta\Psi$ and inner bacterial pH of Mtb cells treated with DMSO and water (solvent controls: "DMSO" and "H2O" bars), control antibiotics (isoniazid, rifampicin, ciprofloxacin), PMF dissipators (valinomycin, nigericin and CCCP), or the MmpL3 inhibitors SQ109, THPP1, AU1235, NITD-304 and NITD-349 at 4 times and 20 times their MIC value were determined. For solubility reasons, BM212 and nigericin were tested at 2- and 8-times their MIC value. [MIC values: NITD-304, 0.02 µM; NITD-349, 0.05 µM; SQ109, 2.36 µM; AU1235, 0.48 µM; BM212, 3.76 µM; THPP1, 13.44 µM; INH, 0.58 µM; RIF, 0.19 µM; nigericin, 4.31 µM; CCCP, 6.25 µM]. Left bars are for the 2- or 4-times MIC treatments; right bars are for the 8- or 20-times MIC treatments. Results are representative of three independent tests. The values represent the averages and standard deviations of measurements performed on three independent bacterial suspensions after exposure to the test compounds or solvents for 30 minutes at 37° C. Asterisks denote statistically significant differences between water or DMSO controls and inhibitor-treated cells as per the Student's t-test (P<0.05).

Figure 9A:
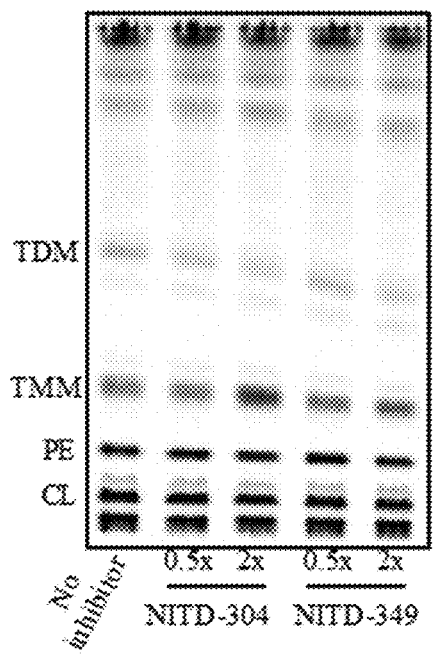
Figure 9A:
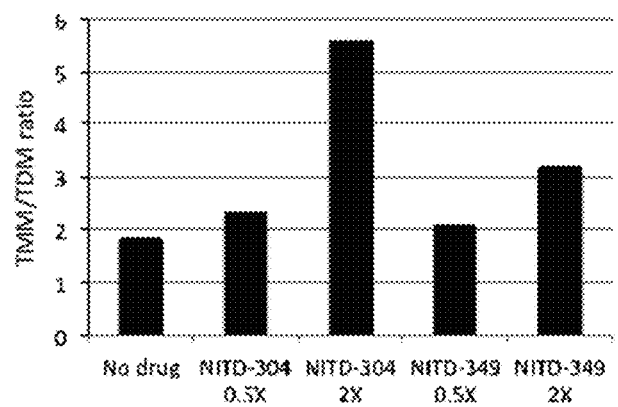
Figure 9B:
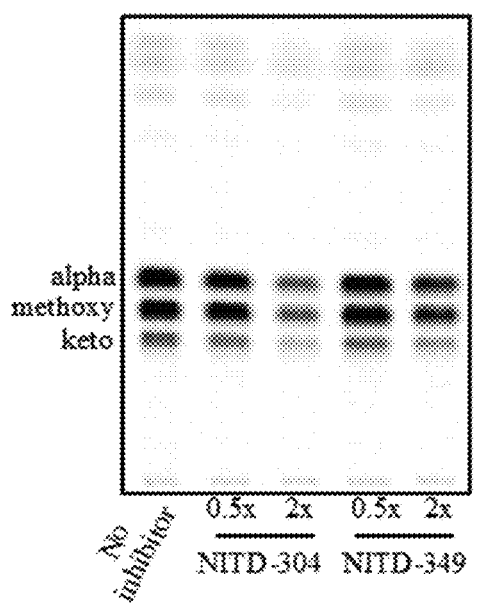
Figure 9B:
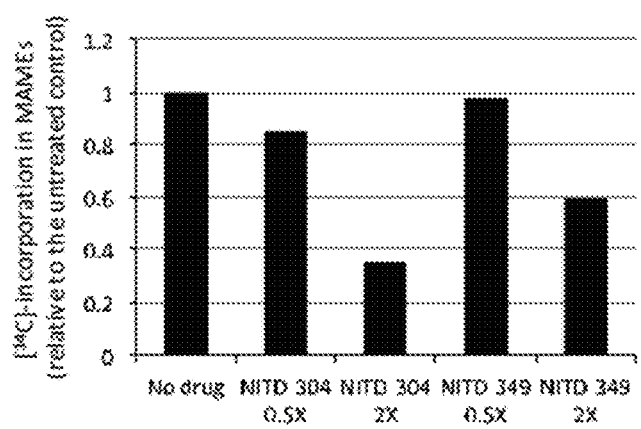

FIGS. 9A-9B shows the effects of NITD-304 and NITD-349 on the transfer of mycolic acids onto their cell envelope acceptors in Mtb. Lipid and cell wall-bound mycolic acid methyl ester (MAME) analysis of untreated and NITD304- and NITD-349-treated Mtb H37Rv mc$^2$6206 cells. Bacterial cultures were treated for 24 hours with 0.5× and 2×MIC concentrations of compounds and labeled concomitantly with [1,2-$^{14}$C]-acetate (0.5 µCi/ml; specific activity 54.3 Ci/mol; Perkin Elmer, Inc.). FIG. 9A: 20,000 cpm of [$^{14}$C]-acetate-labeled lipids from each sample was analyzed by TLC in the solvent system [CHCl$_3$:CH$_3$OH:H$_2$O, 20:4:0.5] and revealed by phosphorimaging. PE, phosphatidylethanolamine; CL, cardiolipin; TMM, trehalose monomycolate; TDM, trehalose dimycolate. The amount of radioactivity incorporated in TMM and TDM was semi-quantified using a PhosphorImager and the TMM to TDM ratio in each sample presented as a histogram. FIG. 9B: MAMEs prepared from the same untreated and NITD-treated cells (same volume loaded per sample) were analyzed by TLC in the solvent system (n-hexane:ethyl acetate, 95:5; three developments). The amount of radioactivity incorporated in the products was semi-quantified using a PhosphorImager and the results are expressed relative to the value measured in the untreated control (arbitrarily set to 1).

Figure 10:
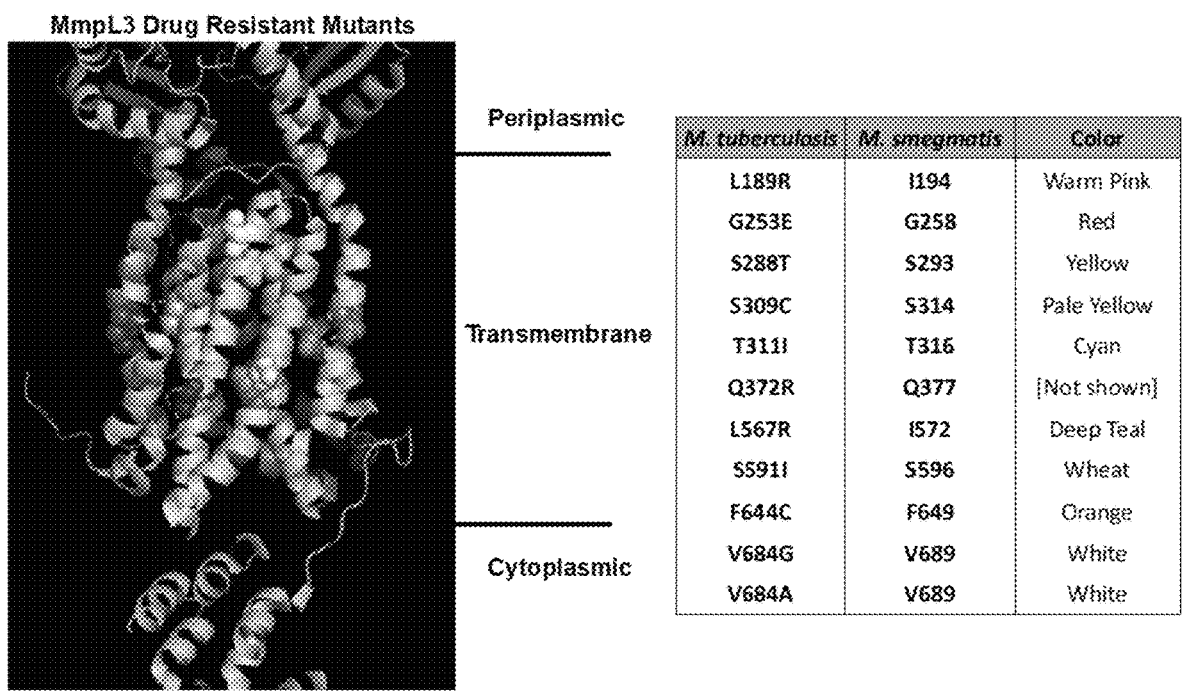

FIG. 10 shows Structure of monomeric MmpL3 from Msmg showing some of the most common resistance mutations in the transmembrane region of the transporter.

Figure 11A:
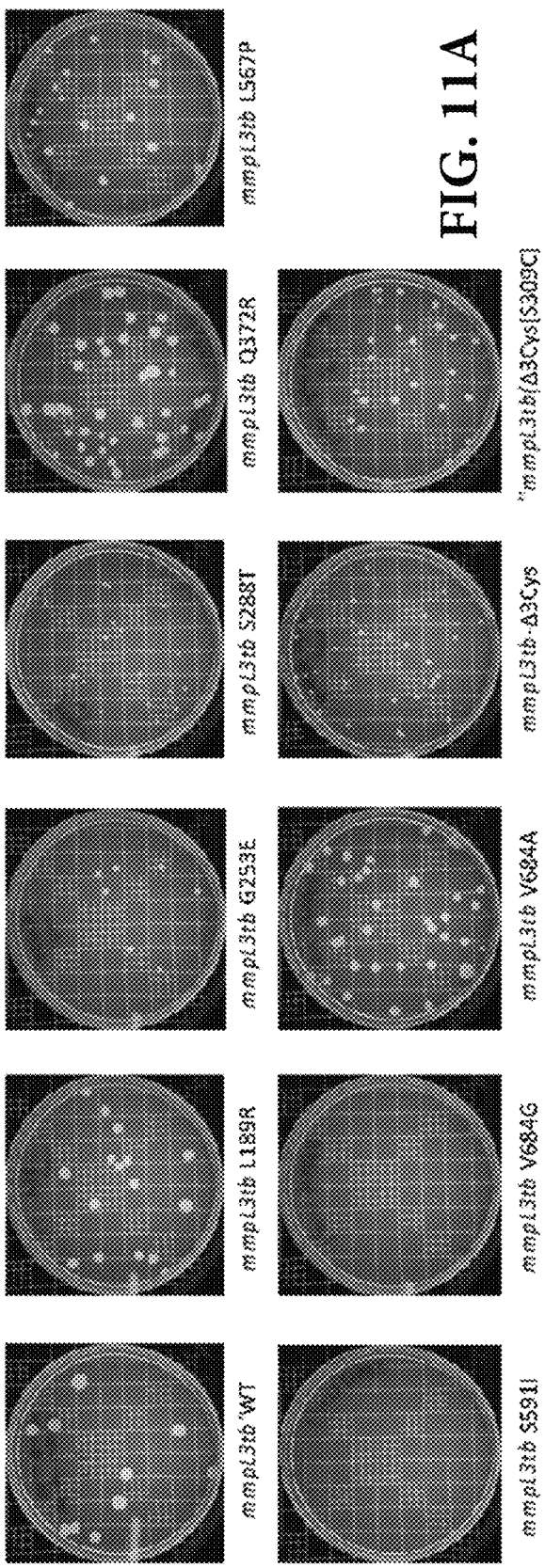
Figure 11B:
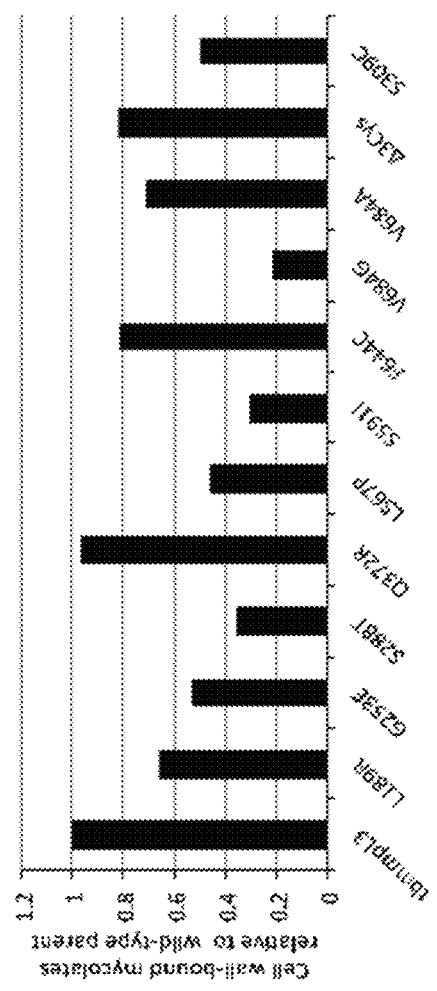
Figure 12:
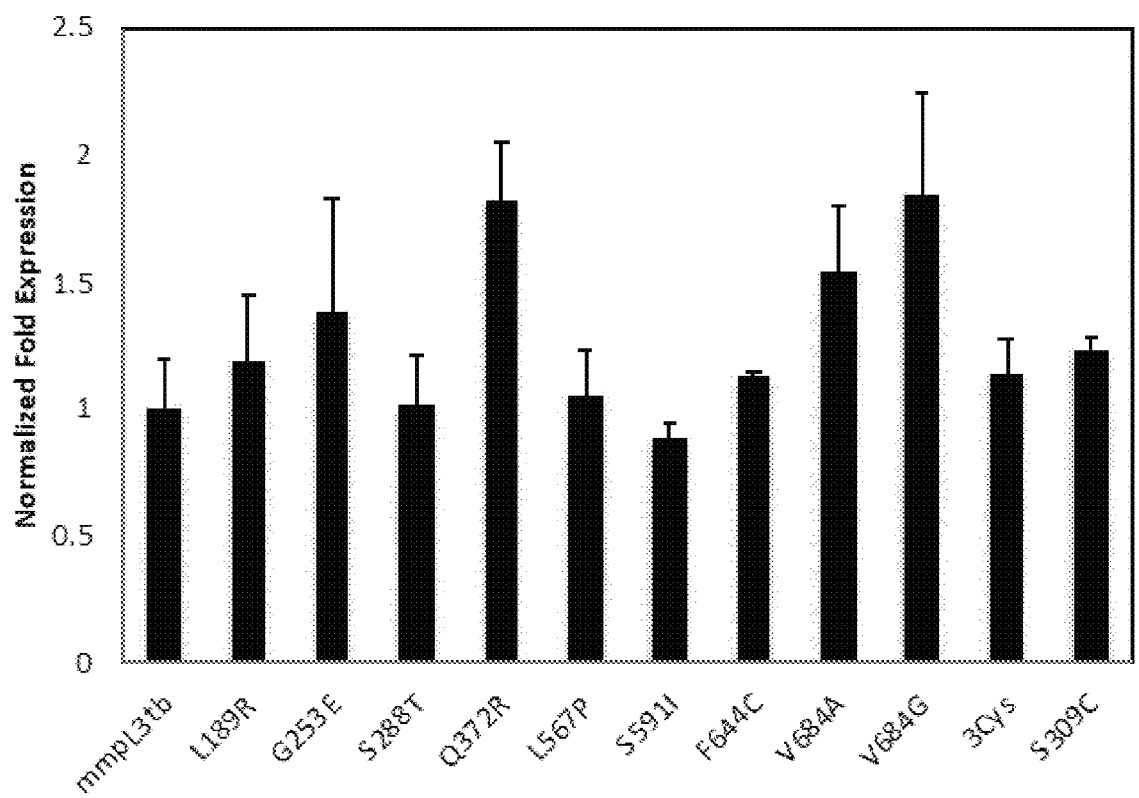

FIGS. 11A-11B shows effects of resistance mutations on growth and mycolic acid export. FIG. 11A: Representative images of growth rate of Msmg$\Delta$mmpL3 rescued with the different mmpL3tb resistant mutants shown in Tables 1A-1B on LB agar after six days of incubation at 37° C. The level of expression of the various mmpL3tb mutants was comparable in all strains, as shown in FIG. 12. FIG. 11B: Log phase cultures (OD$_{600\,nm}$=0.6) of the control and mutant strains were labeled with [1,2-$^{14}$C]acetate for 3 hours in LB-Tween 80 broth and their cell wall-bound mycolic acids analyzed by TLC. A decrease in mycolic acid transfer to arabinogalactan was observed in most mutants. Msmg$\Delta$mmpL3/pMVGH1-mmpL3tb$\Delta$3Cys ($\Delta$3Cys), expressing a triple Cys mutant of MmpL3tb (see e.g., Belardinelli et al, *ACS Infect. Dis.* 2016, 2, 702-713), was used as the control strain for the S309C mutant. Msmg$\Delta$mmpL3/pMVGH1-mmpL3tb (mmpL3tb) was used as the control strain for all other mutants. The amount of radioactivity incorporated in cell wall-bound mycolic acids was semi-quantified using a PhosphorImager and the results are expressed relative to the value measured in the mmpL3tb control (arbitrarily set to 1).

FIG. 12 shows qRT-PCR analysis of mmpL3tb expression in the Msmg parent and resistant mutants shown in Tables 1A-1B. Msmg$\Delta$mmpL3/pMVGH1-mmpL3tb$\Delta$3Cys ($\Delta$3Cys) was used as the control strain for the S309C mutant. Msmg$\Delta$mmpL3/pMVGH1-mmpL3tb (mmpL3tb) was used as the control strain for all other mutants. Expression data were normalized to sigA expression in each sample and represent the mean of three independent PCRs performed on one to two independent cDNA preparations. qRT-PCRs were run using the pairs of primers, mmpL3RT2A (5'-CGTGTTCTCCGACCTGGTGATG-3') (SEQ ID NO.: 1) and mmpL3RT2B (5'-GCTTGCGCTCGTCGGGCAG-3') (SEQ ID NO.: 2) for mmpL3tb, and sigAF (5'-CGGTGCA-CATGGTCGAGGTG-3') (SEQ ID NO.: 3) and sigAR1 (5'-TCGTCGCCGATGGTCTGGTC-3') (SEQ ID NO.: 4) for sigA, and the SsoFast™ Evagreen® Supermix kit (Bio-Rad) as per the manufacturers' protocols. Data were analyzed on a CFX96 real-time PCR machine (Biorad). PCR conditions: 98° C. (2 min; enzyme activation), followed by 35 cycles of 98° C. (5 sec; denaturation) and 55° C. (5 sec; annealing/extension). Mock reactions (no reverse transcription) were done on each RNA sample to rule out DNA contamination. Differences in mmpL3 expression between the WT mmpL3tb control and mutant mmpL3tb-expressing strains were considered to be not significant as per the Student's t-test (P>0.05).

Figure 13A:
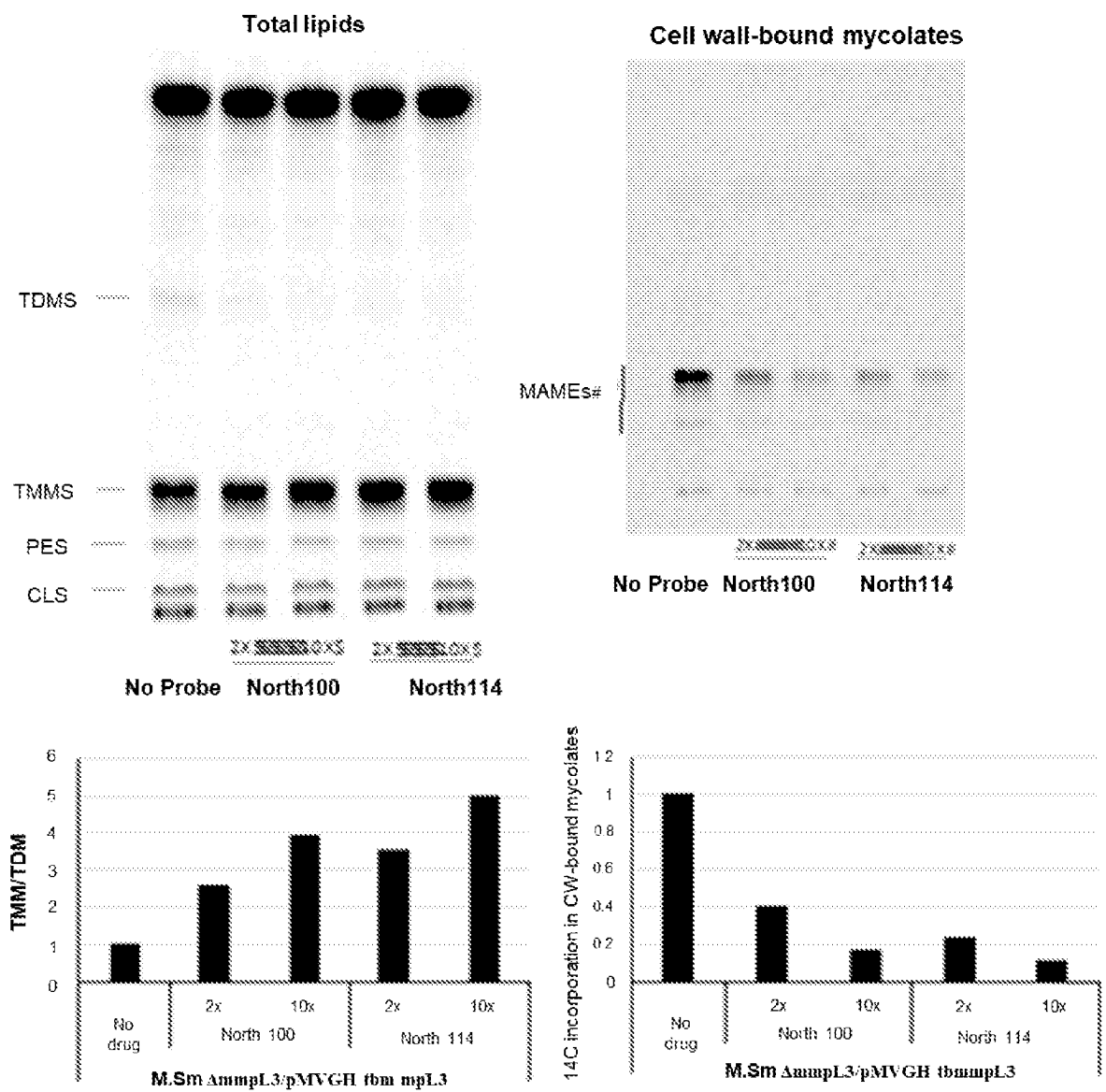
Figure 13B:
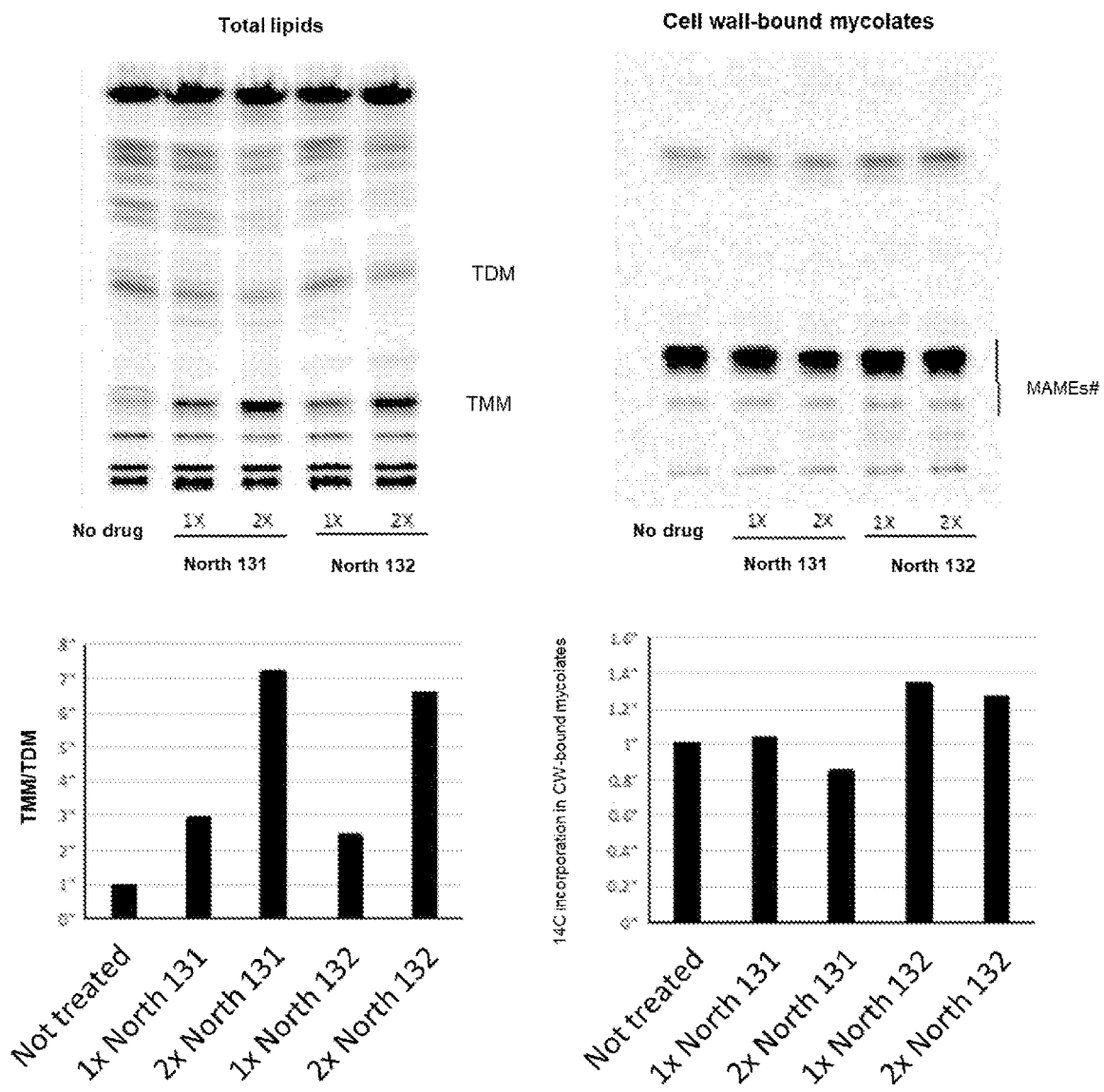

FIGS. 13A-13B show effects of inhibitor probes Compound 1, Compound 2, Compound 3 (i.e., North 131) and Compound 4 (i.e., North 132) on the transfer of mycolic acids onto their cell envelope acceptors in Msmg$\Delta$mmpL3/pMVGH1-mmpL3tb. Bacterial cultures were treated with 2× and 10×MIC concentrations of North 100 and North 114

(FIG. 13A) or 1× and 2×MIC concentrations of North 131 and North 132 (FIG. 13B) and labeled concomitantly with [1,2-$^{14}$C]-acetate (0.5 µCi/ml; specific activity 54.3 Ci/mol; Perkin Elmer, Inc.). 20,000 cpm of [$^{14}$C]-acetate-labeled lipids from each sample was analyzed by TLC in the solvent system [CHCl$_3$:CH$_3$OH:H$_2$O, 20:4:0.5] and revealed by phosphorimaging. Mycolic acid esters (MAMEs) prepared from the same untreated and probe-treated cells (same volume loaded per sample) were analyzed by TLC in the solvent system (n-hexane:ethyl acetate, 95:5; three developments). The amount of radioactivity incorporated in MAMEs, TMM and TDM was semi-quantified using a PhosphorImager, and both TMM to TDM ratios and MAME content in each sample expressed relative to the values measured in the untreated control are shown (arbitrarily set to 1). Similar results were obtained in MsmgΔmmpL3/pMVGH1-mmpL3tb-gfp cells. The MIC values of the probes against MsmgΔmmpL3/pMVGH1-mmpL3tb are indicated in Table 1B.

Figure 3A:
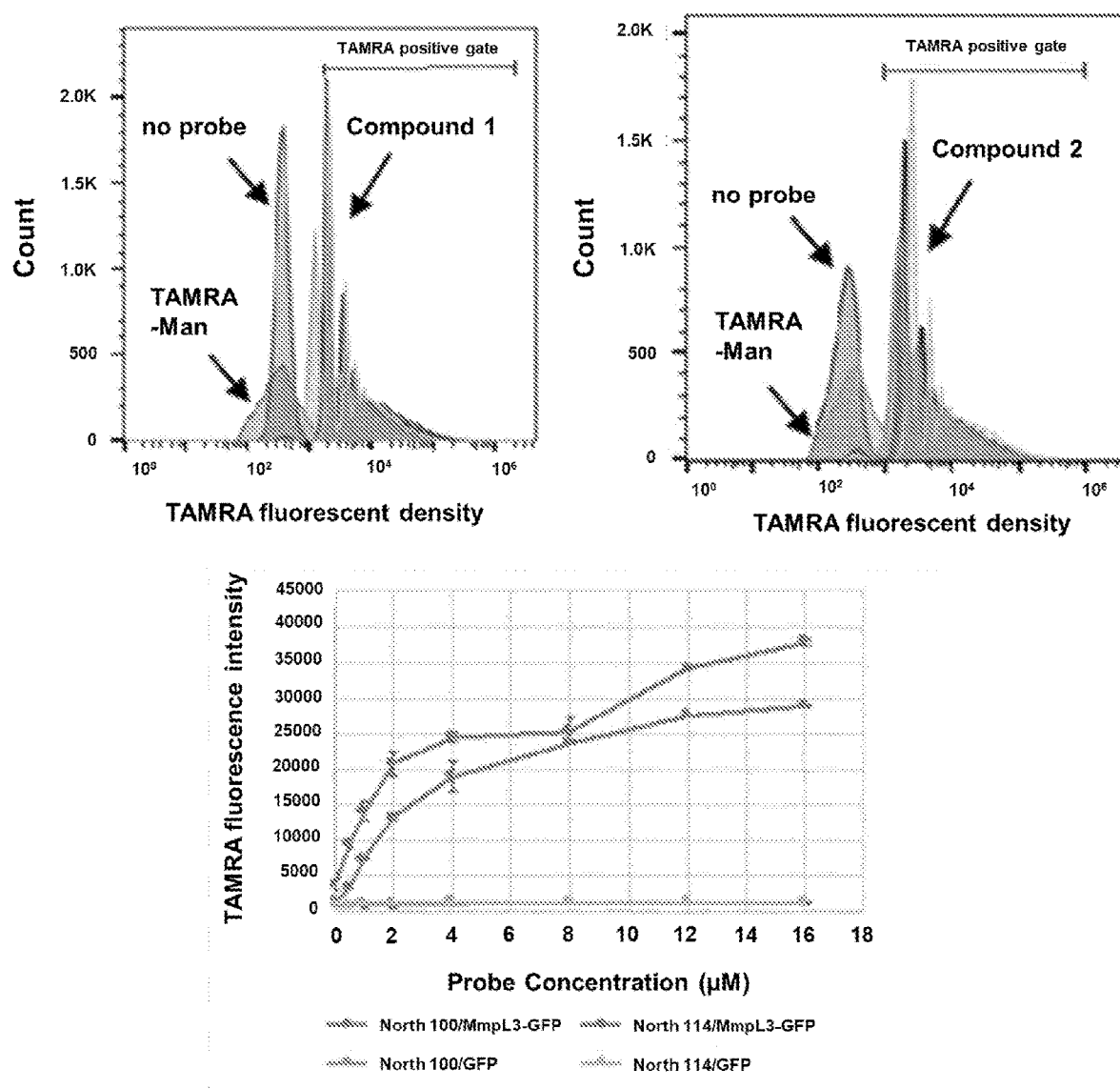
FIG. 3A shows comparative analysis of the binding of indolecarboxamide probes to MmpL3tb-GFP bound to polystyrene particles. MmpL3tb-GFP-coated beads were incubated for 15 min at room temperature with different concentrations of Compound 1 (i.e., North 100) and Compound 2 (i.e., North 114). After three washes in PBS pH 7.0-5% glycerol, the TAMRA mean fluorescence intensity (MFI) of the beads was analyzed by flow cytometry. The histograms show the absence of binding of the TAMRA-mannose probe to MmpL3tb-GFP-coated beads, while Compound 1 and Compound 2 bind to particles coated with different concentrations of MmpL3tb-GFP. The graph shows the concentration-dependent binding of Compound 1 and Compound 2 to particles coated with MmpL3tb-GFP; no binding is observed on particles coated with GFP alone. The MFI reported are mean values SD of technical triplicates and are representative of at least two independent experiments.
Figure 3B:
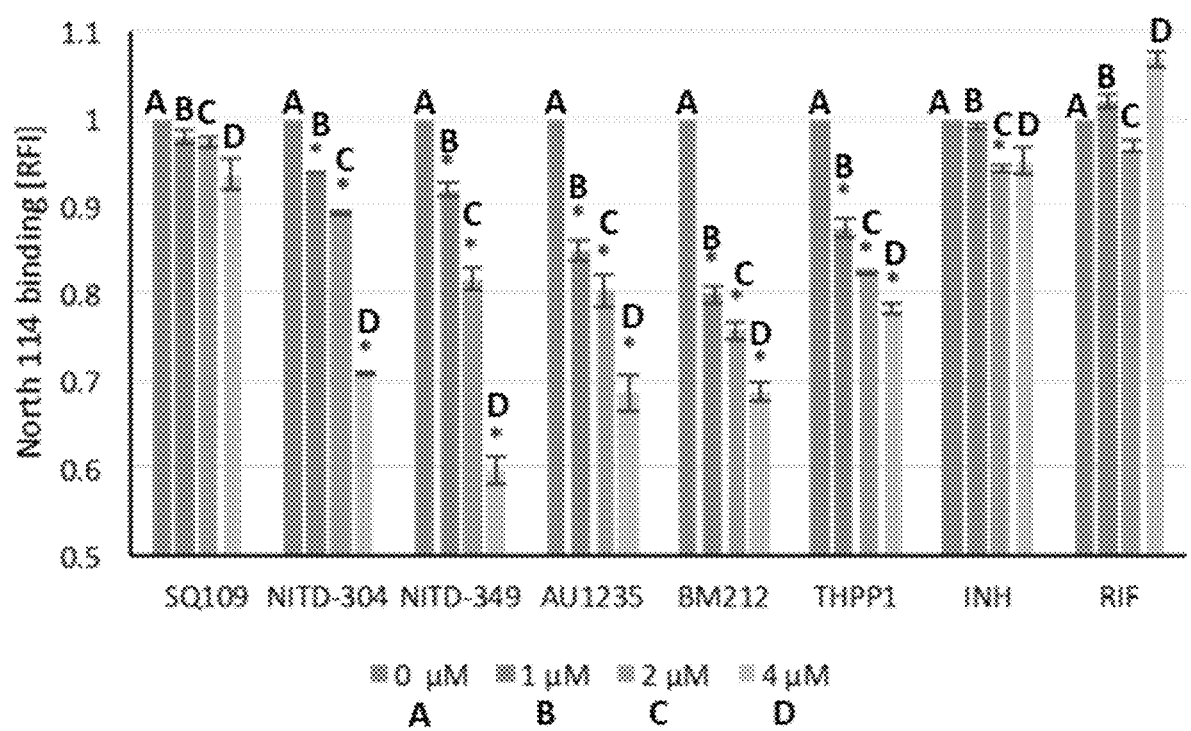
FIG. 3B shows flow cytometry-based competition binding assay performed on purified MmpL3-GFP. Cells were co-treated with 2 μM Compound 2 and increasing concentrations of the inhibitors as described under Methods. The concentrations of inhibitors are indicated under the X-axis. Shown on the Y-axis are the MFI of the polystyrene particles from each treatment group expressed relative to that of particles not treated with any inhibitor (relative fluorescence value [RFI] arbitrarily set to 1). MFIs were determined by analyzing 10,000 particles under each condition. The data reported are mean values SD of technical duplicates and are representative of at least three independent experiments. Asterisks denote statistically significant decreases in fluorescence intensity between no inhibitor control ("A" bars) and beads co-treated with Compound 2 and various concentrations of the inhibitors as per the Student's t-test (P<0.05). No significant displacement was seen with the negative control drugs isoniazid (INH) and rifampicin (RIF) whose mechanisms of action are independent of MmpL3tb (with the exception of INH at 2 μM but not 4 μM).
Figure 4:
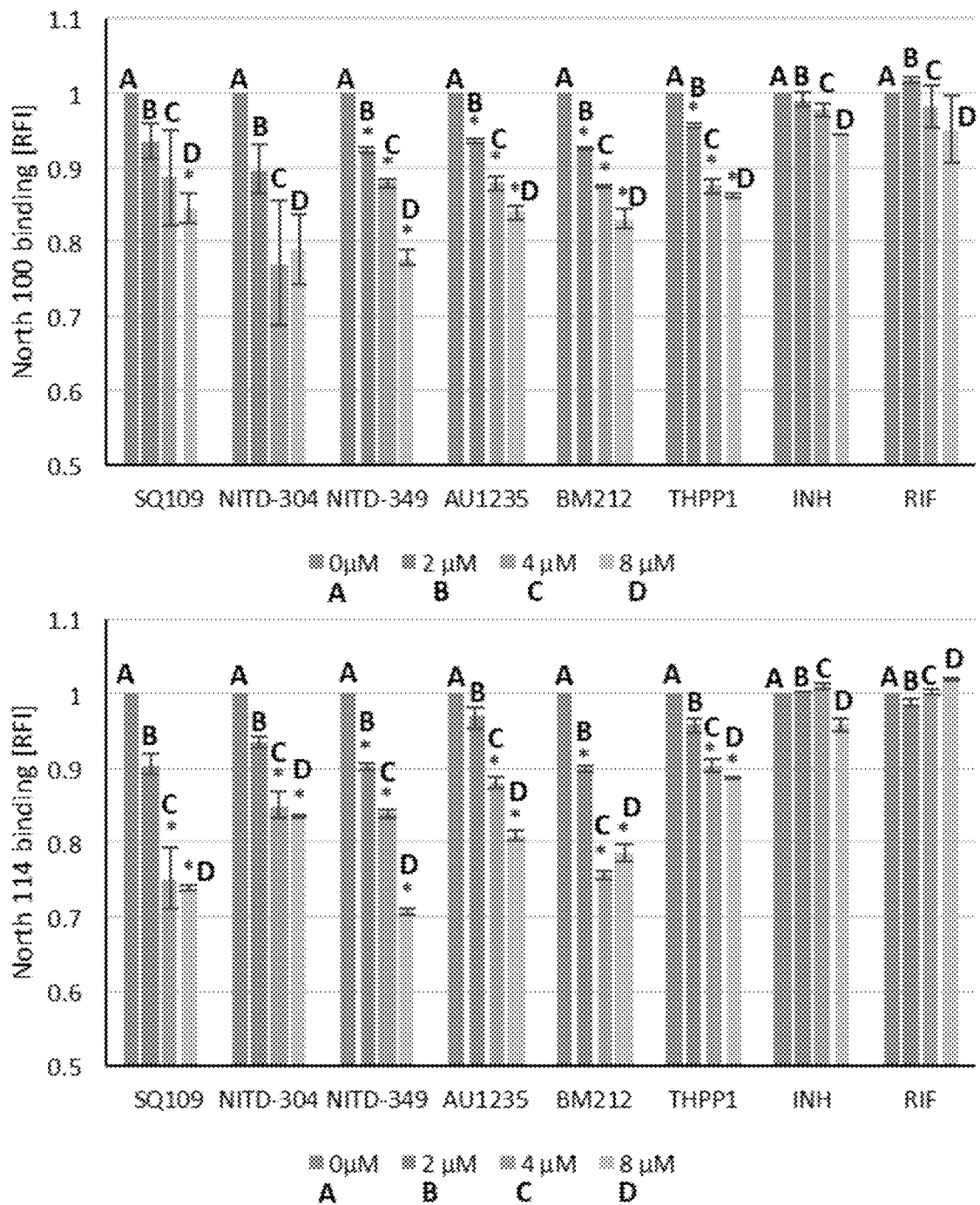
FIG. 4 shows flow cytometry-based competition binding assay performed in an Msmg mmpL3 deletion mutant expressing the wild-type mmpL3tb gene fused to gfp (MsmgΔmmpL3/pMVGH1-mmpL3tb). Cells were labeled with 4 μM Compound 1 (top graph) or Compound 2 (bottom graph) and subsequently treated with increasing concentrations of the inhibitors as described herein. The concentrations of inhibitors are indicated under the X-axis. Shown on the Y-axis are the mean fluorescence intensities (MFI) of the bacilli from each treatment group expressed relative to that of bacilli not treated with any inhibitor (relative fluorescence value [RFI] arbitrarily set to 1). MFIs were determined by analyzing 10,000 bacilli under each condition. The data reported are mean values SD of technical duplicates and are representative of at least three independent experiments. Asterisks denote statistically significant decreases in fluorescence intensity between no inhibitor controls ("A" bars) and bacilli co-treated with Compound 1 or Compound 2 and various concentrations of the inhibitors as per the Student's t-test (P<0.05).
Figure 14:
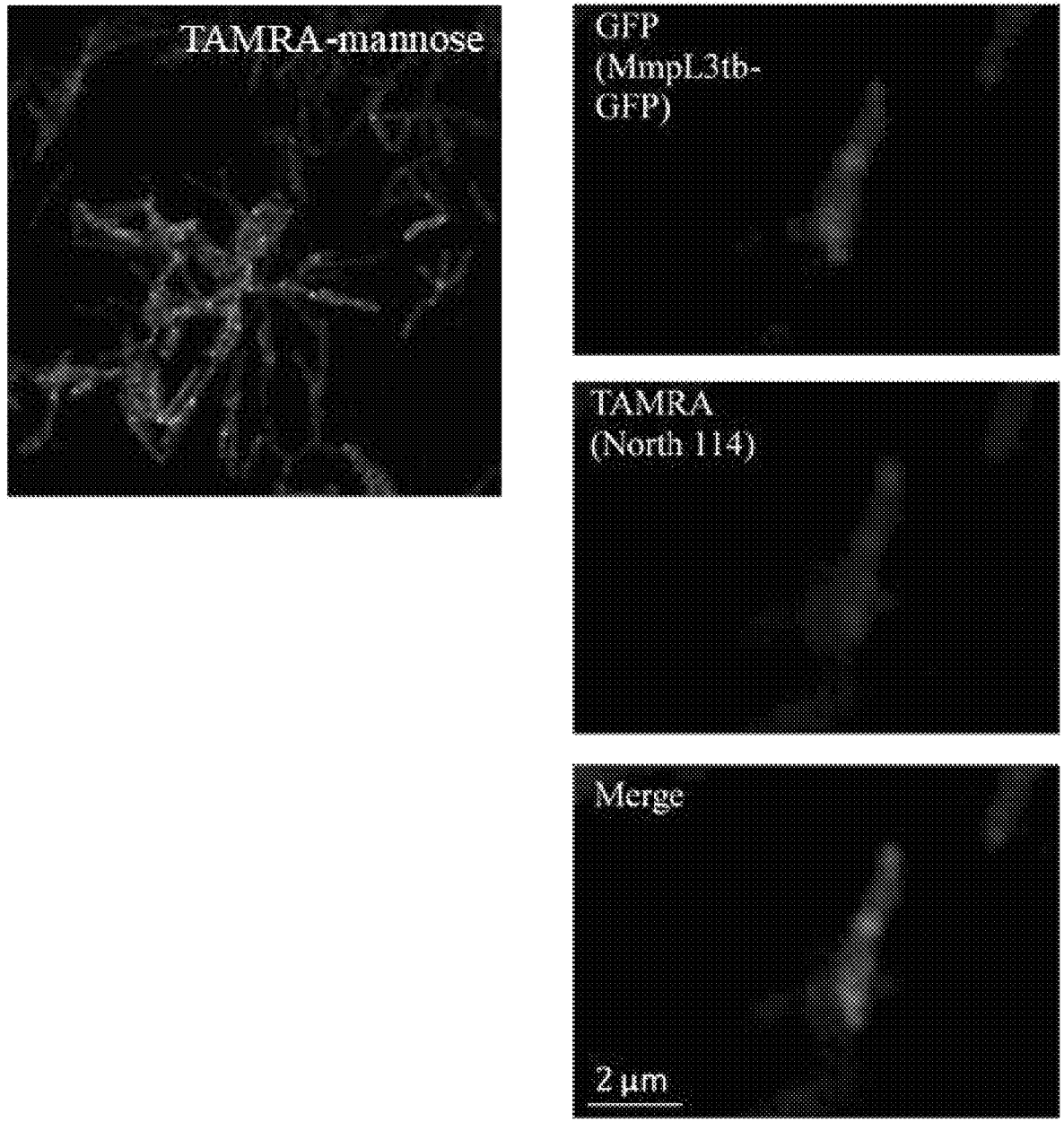
Figure 15:
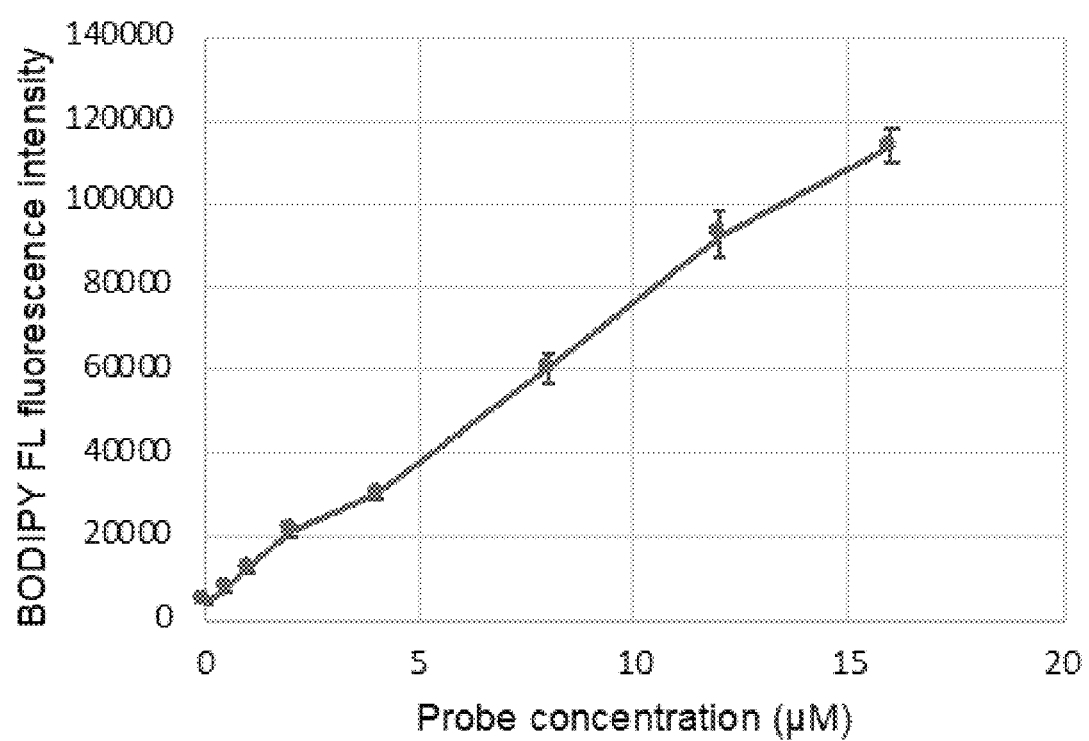

FIG. 14 shows co-localization of Compound 2 with MmpL3tb-GFP at the old poles and septa of an M. smegmatis mmpL3 deletion mutant expressing an mmpL3tb-gfp fusion. No colocalization with MmpL3 as observed with the negative control probe TAMRA-Mannose FIG. 15 shows evidence of adamantyl urea probe binding to purified MmpL3tb. The beads were incubated with the probe as described in FIG. 3 and the BODIPY FL mean fluorescence intensity (MFI) of the beads was analyzed by flow cytometry. The MFI reported are mean values±SD of technical triplicates and are representative of at least two independent experiments.

Figure 16A:
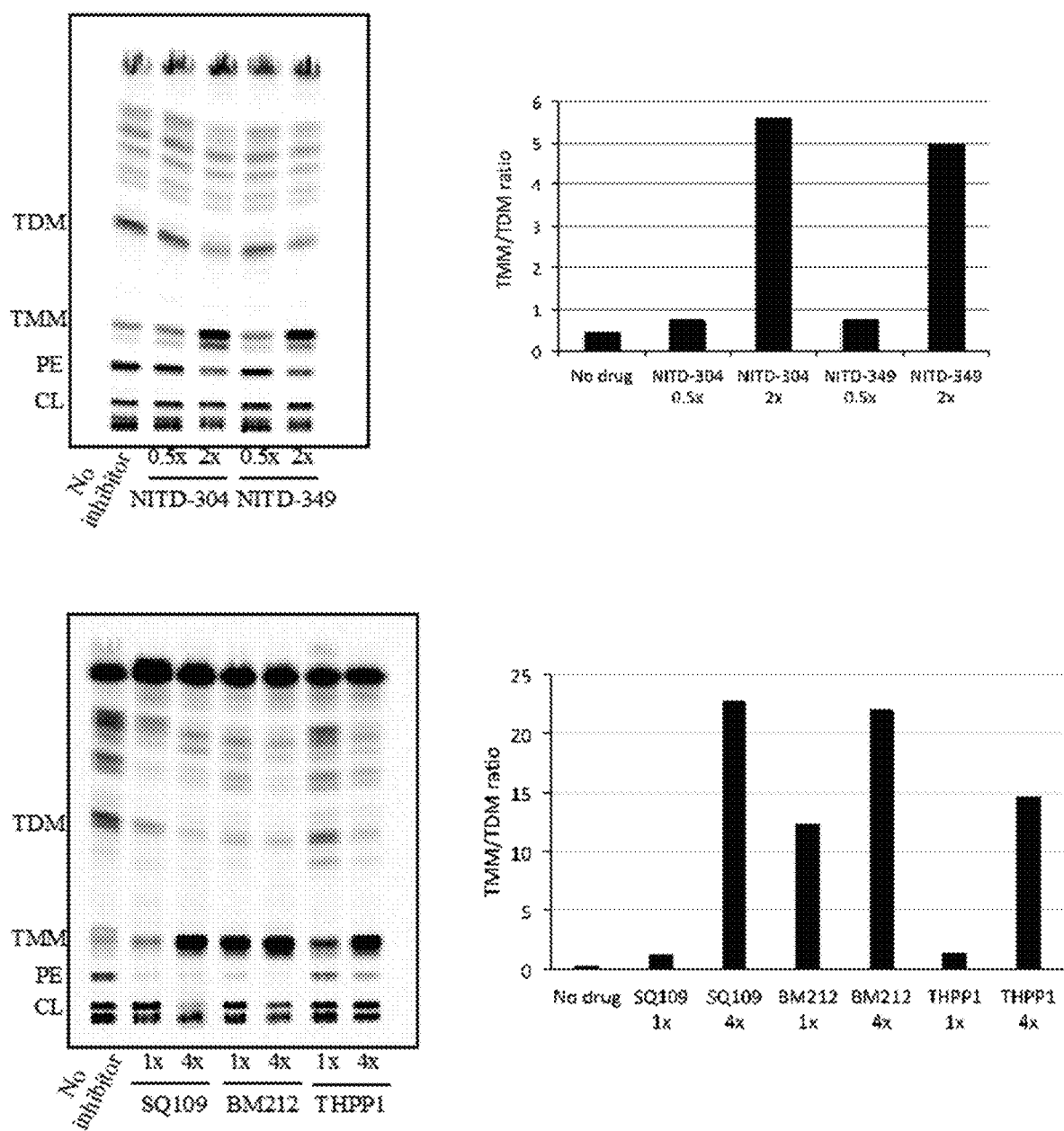
Figure 16B:
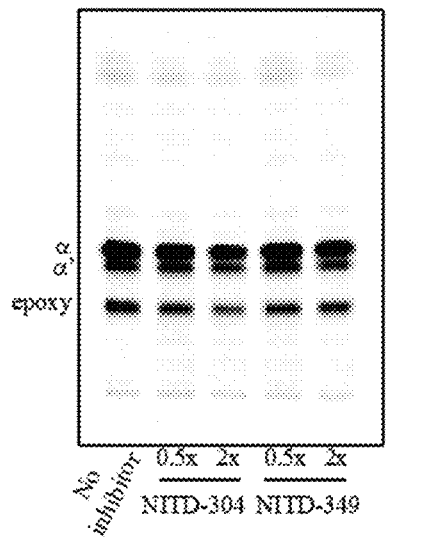
Figure 16B:
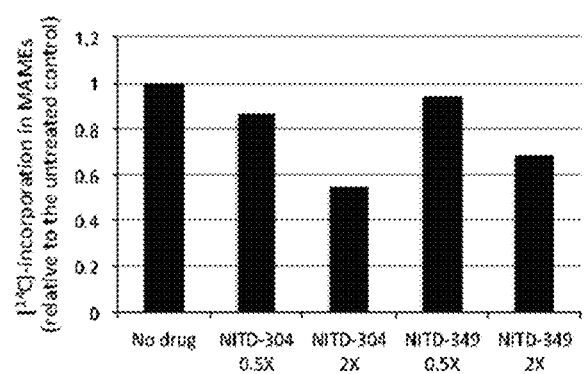
Figure 16B:
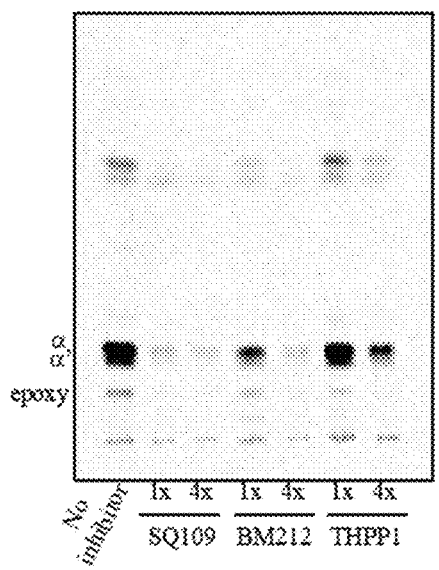
Figure 16B:
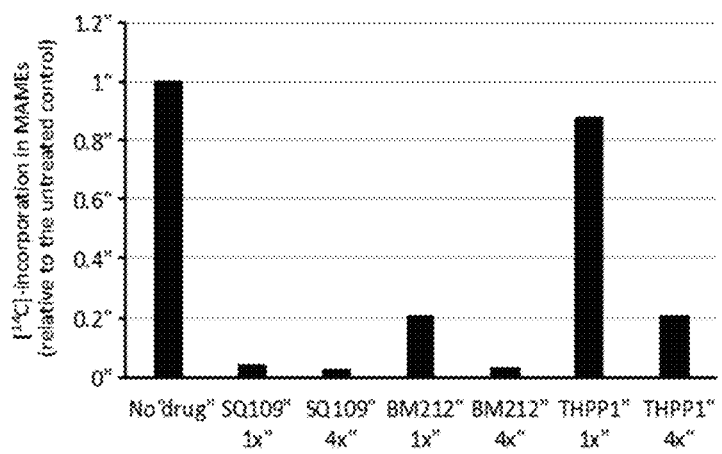

FIGS. 16A-16B show effects of NITD-304, NITD-349, BM212, THPP1 and SQ109 on the transfer of mycolic acids onto their cell envelope acceptors in MsmgΔmmpL3/pMVGH1-mmpL3tb. Bacterial cultures were treated for 3 hours with 0.5×, 1×, 2× or 4×MIC concentrations of compounds and labeled concomitantly with [1,2-$^{14}$C]-acetate (0.5 µCi/ml; specific activity 54.3 Ci/mol; Perkin Elmer, Inc.). FIG. 16A: 20,000 cpm of [$^{14}$C]-acetate-labeled lipids from each sample was analyzed by TLC in the solvent system (CHCl$_3$:CH$_3$OH:H$_2$O, 20:4:0.5) and revealed by phosphorimaging. PE, phosphatidylethanolamine; CL, cardiolipin; TMM, trehalose monomycolate; TDM, trehalose dimycolate. The amount of radioactivity incorporated in TMM and TDM was semi-quantified using a PhosphorImager and are shown as the TMM to TDM ratio in each sample. FIG. 16B: MAMEs prepared from the same untreated and NITD-treated cells (same volume loaded per sample) were analyzed by TLC in the solvent system (n-hexane:ethyl acetate, 95:5; three developments). The amount of radioactivity incorporated in the products of interest was semi-quantified using a PhosphorImager and the results are shown relative to the value measured in the untreated control (arbitrarily set to 1).

Figure 17A:
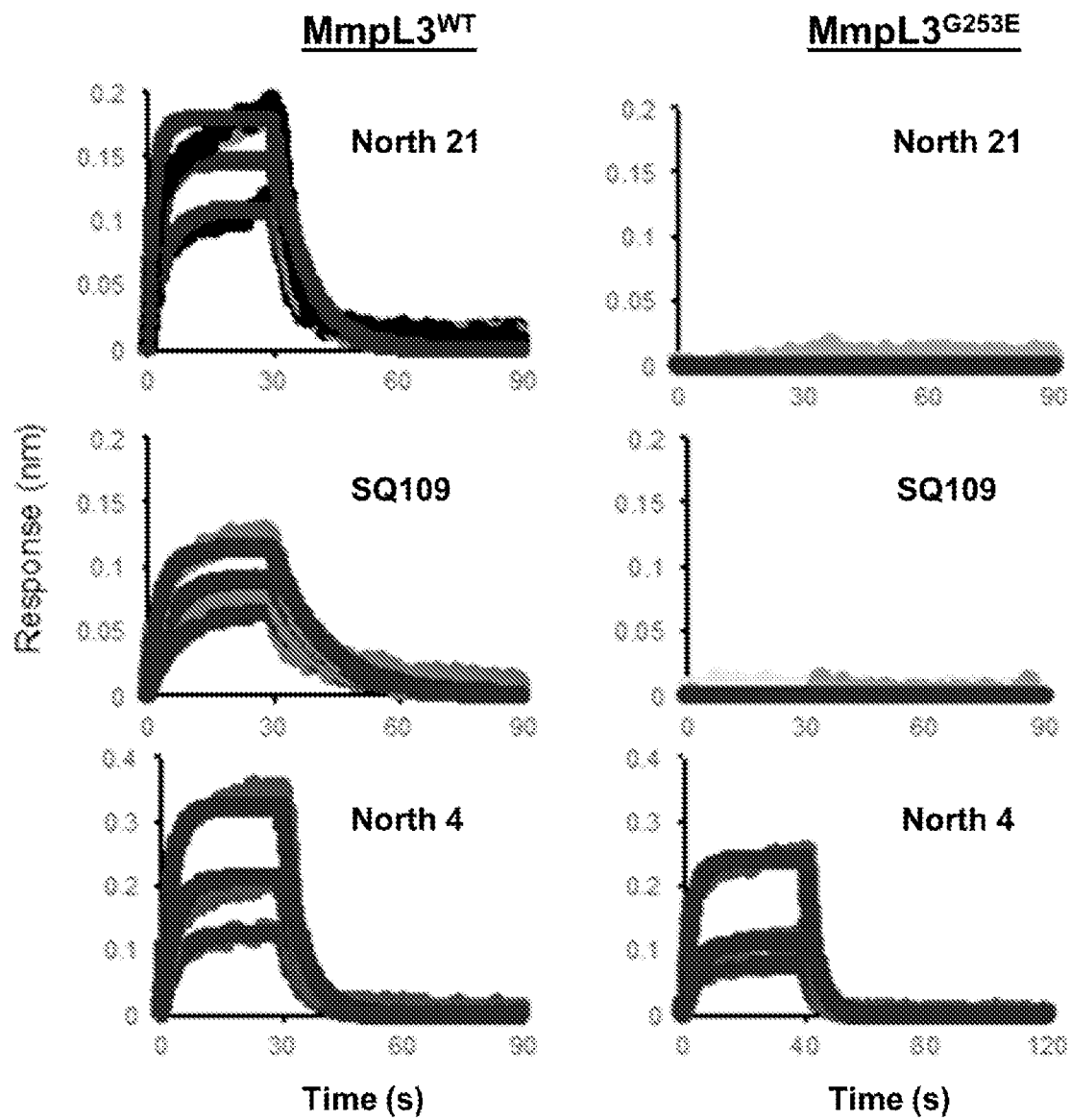
Figure 17B:
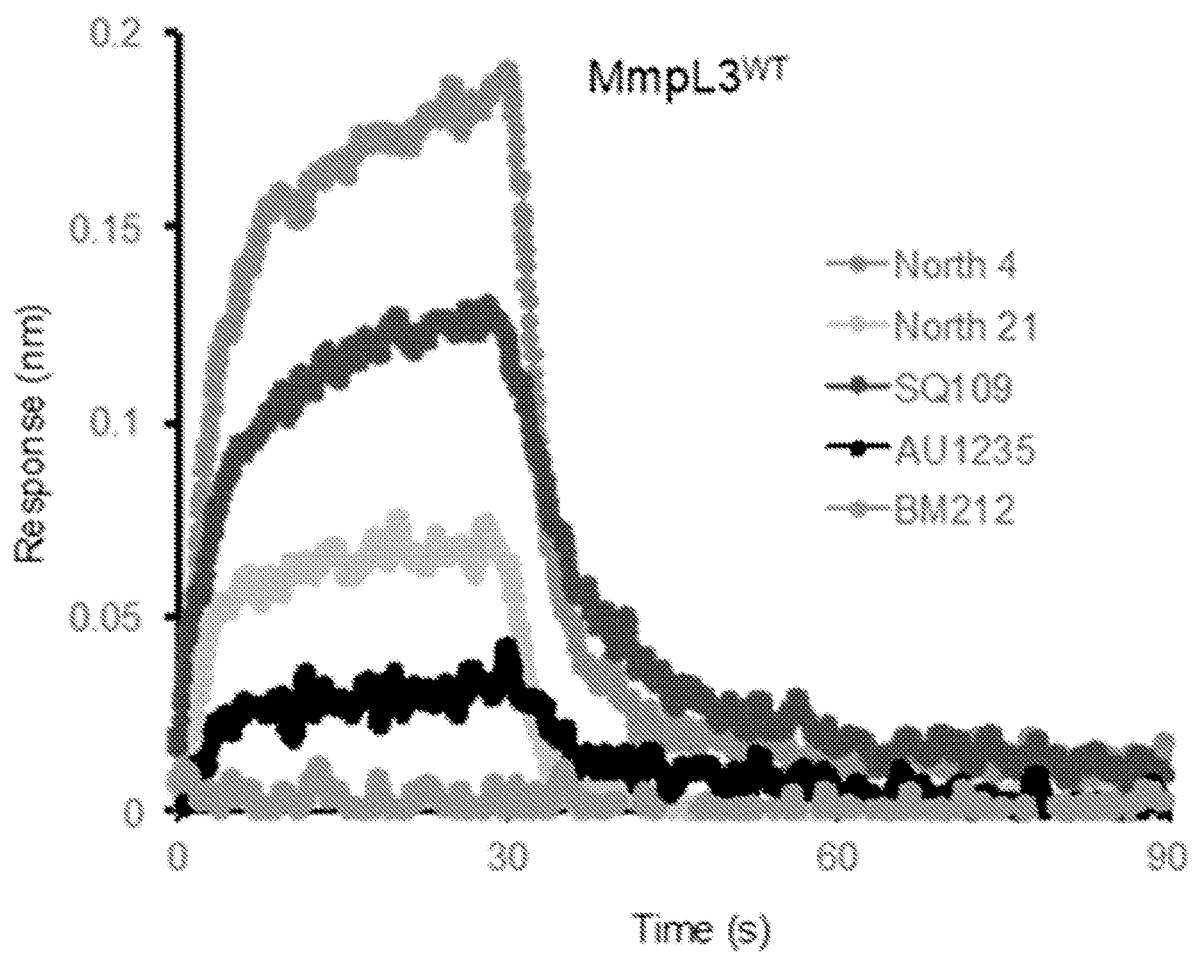

FIGS. 17A-17B show biolayer interferometry spectra for inhibitors binding to MmpL3$^{WT}$ and its resistant variant MmpL3$^{G253E}$. FIG. 17A: Binding of indicated inhibitors at increasing concentrations of 50, 100 and 200 µM to the sensor tips with immobilized MmpL3$^{WT}$ (left) or MmpL3$^{G253E}$ (right). FIG. 17B: Normalized binding response of North 4, SQ109, North 21, and AU1235 at concentration of 200 µM and 50 µM for BM212 (the solubility limit in 5% DMSO) to MmpL3$^{WT}$.

Figure 18:
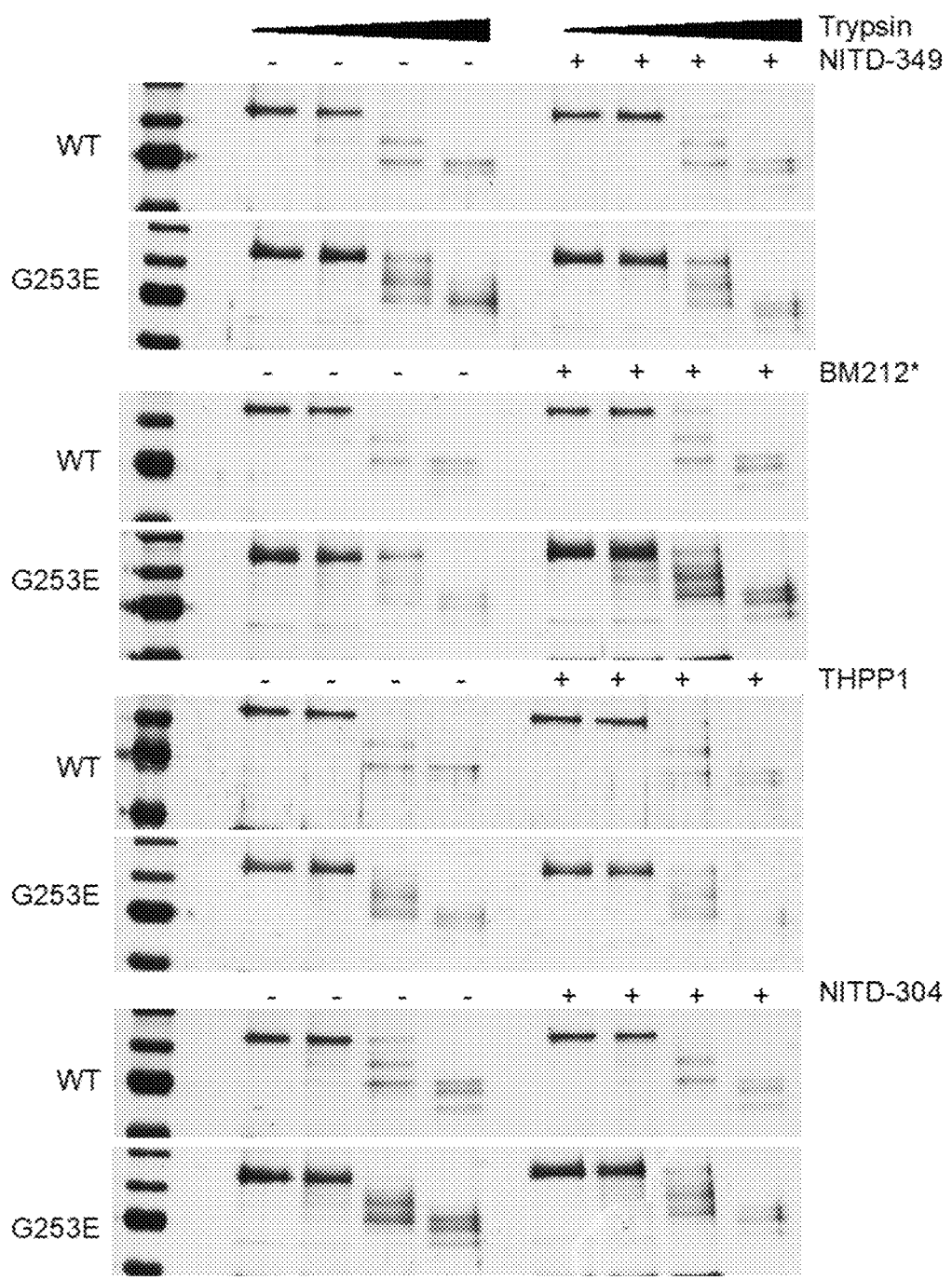

FIG. 18 shows proteolytic profiles of the wild-type MmpL3$^{WT}$ and its resistant variant MmpL3$^{G253E}$ in the presence and absence of inhibitors. Purified proteins (100 nM final concentrations) were incubated with increasing concentrations of trypsin (0.01, 0.1 and 1.0 µg/mL). Inhibitors were added where indicated to the final concentration of 200 µM prior to trypsin. The digest was carried out for 30 min at 37° C. and the tryptic fragments were separated by 12% SDS-PAGE followed by silver nitrate staining.

Figure 19A:
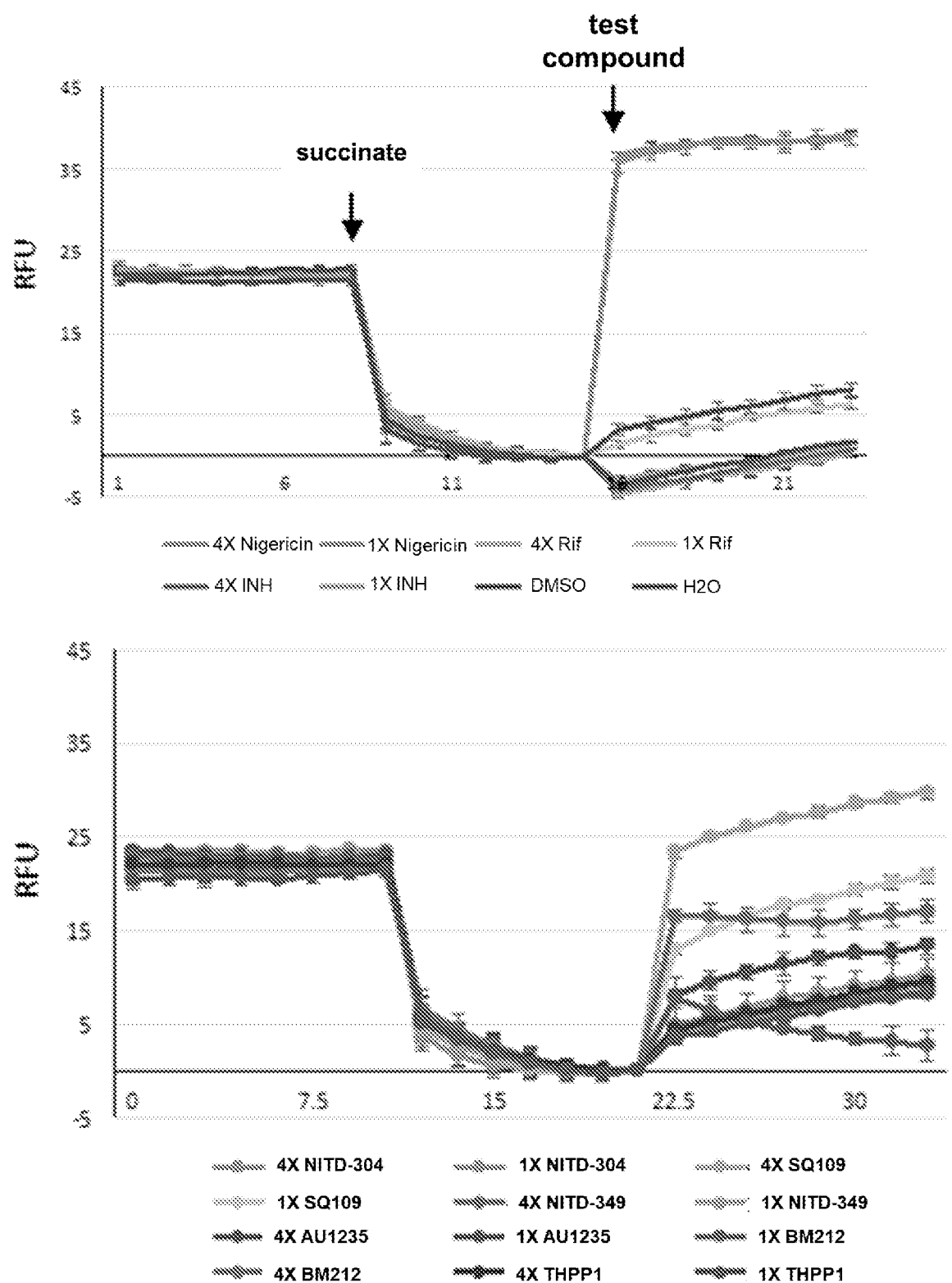
Figure 19B:
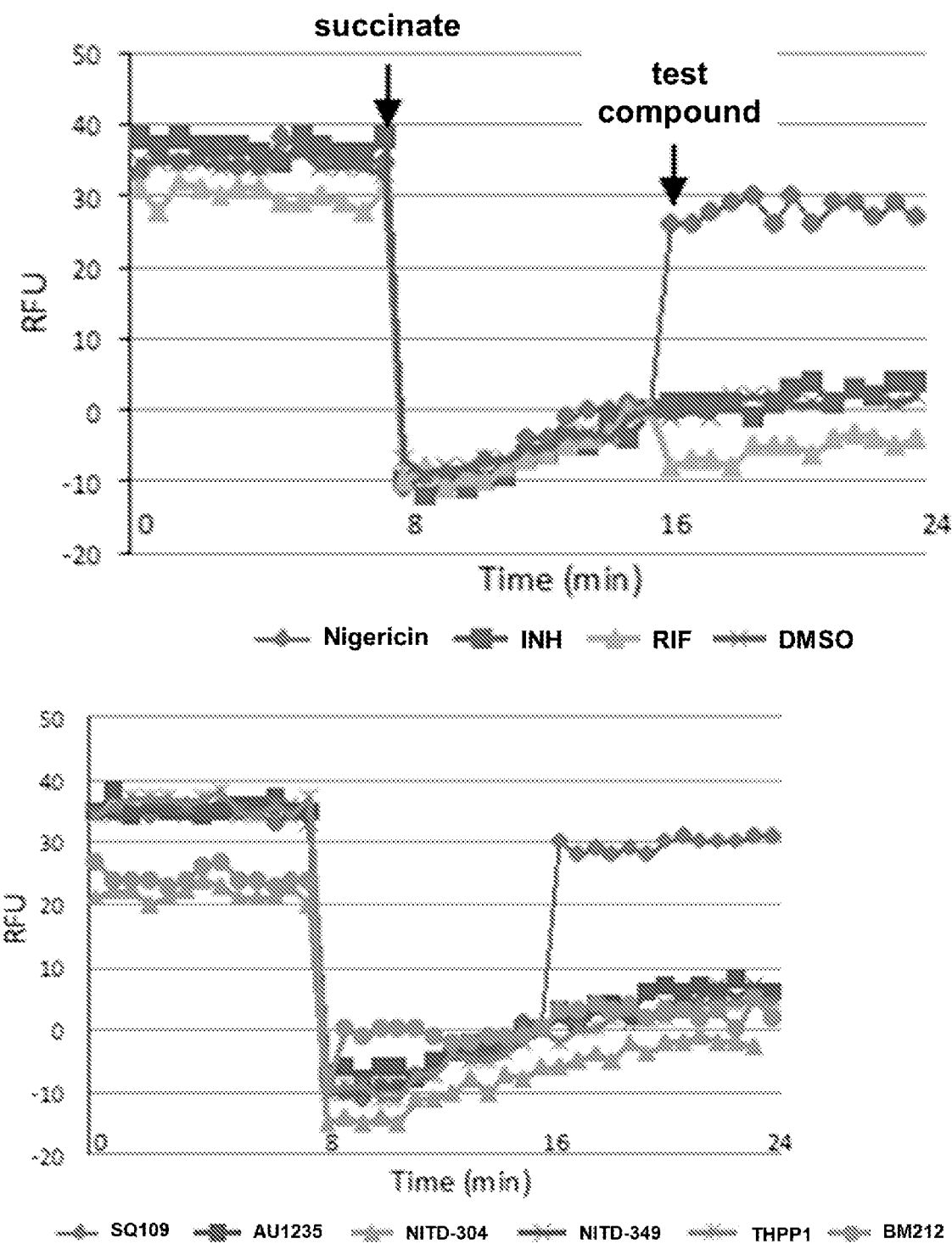

FIGS. 19A-19B show effects of SQ109, BM212, THPP1, AU1235, NITD-304 and NITD-349 on the electrochemical proton gradient (ΔpH) of Mtb and E. coli inverted membrane vesicles. FIG. 19A: The reactions were initiated by adding 5 mM succinate. Upon stabilization of the signal, control compounds (INH, RIF, nigericin), the MmpL3 inhibitors or diluent (water, used for INH, or 0.2% DMSO, used for all other compounds) were added and proton translocation monitored fluorimetrically. MmpL3 inhibitors and controls were used at one and four times their MIC concentrations against Mtb. Shown are the averages and standard deviations (error bars) of triplicate measurements. Addition of nigericin or SQ109 at 1× and 4× their MIC values, AU1235 at 4× its MIC value and BM212 at 4× its MIC value results in an increase of fluorescence intensity indicative of ΔpH collapse. FIG. 19B: Shows the same ACMA assay as describe above using E. coli BL21(DE3) IMVs. All compounds were used at a final concentration of 2 µg/mL (equivalent to 5.9 µM for NITD-304, 6.5 µM for NITD-349, 6 µM for SQ109, 4.8 µM for BM212, 6.2 µM for AU1235 and 4.3 µM for THPP1). Nigericin (positive control; 2 µg/mL; 2.7 µM) and SQ109 collapse the ΔpH of E. coli IMVs.

DETAILED DESCRIPTION

The mycolic acid transporter MmpL3 has been reported to be the putative target of compounds having activity against Mycobacterium tuberculosis (Mtb) or nontuberculous mycobacteria (NTM). The potency that MmpL3 inhibitors display against multi-drug resistant (MDR) strains of Mtb, and their synergistic interactions with a number of anti-TB drugs and drug candidates (see e.g., Li, et al, Antimicrob. Agents Chemother. 2017, 61:DOI 10.1128/AAC.02399-16; and Li et al, Front Microbiol. 2018, 9:1547) further highlight the potential that MmpL3 inhibitors have to reduce the duration of TB and MDR-TB treatments. Accordingly, a number of MmpL3 inhibitors are currently under development; among them, SQ109 (see e.g., Sacksteder et al, Future Microbiol. 2012, 7:823-837), which has completed phase II efficacy studies in TB patients in Africa, and a number indolecarboxamide- and tetrapyrazolopyrimidine-based inhibitors selected on the basis of their mycobactericidal activity, tolerability, favorable pharmacokinetic profiles and efficacy in acute and chronic murine models of TB and NTM infections (see e.g., Rao et al, Sci. Transl. Med. 2013, 5:214ra168; Lun et al, Nat. Commun. 2013, 4:2907; Remuinan et al, PLoS ONE 2013, 8:e60933; Yokokawa et al, ACS Med Chem. Lett. 2013, 4:451-455; Stec et al, J. Med Chem. 2016, 59:6232-6247; Cox et al, Nat. Microbiol. 2016, 1:15006; Franz et al, Bioorg. Med Chem. 2017, 25:3746-3755; Kozikowski et al, J. Med Chem. 2017, 60:5876-5888; De Groote et al, Front Microbiol. 2018, 9:2231; and Pandya et al, Antimicrob. Agents Chemother. 2019, 63:DOI 10.1128/AAC.02245-18).

The lack of simple and relatively high-throughput assays to rapidly screen potential MmpL3 inhibitors currently represents an obstacle to further development. For example, some of these inhibitors have more than one target in Mtb (including other targets in the mycolic acid biosynthetic pathway) (see e.g., Cox et al, Nat. Microbiol. 2016, 1:15006; and Li et al, Antimicrob. Agents Chemother. 2014, 58:6413-

6423). It has been observed that a subset of compounds may exert their inhibitory effect on MmpL3 by dissipating the proton motive force (PMF) from which MmpL transporters derive their energy (see e.g., Li et al, *Antimicrob. Agents Chemother.* 2014, 58:6413-6423; Li et al, *J. Med. Chem.* 2014, 57:3126-3139; Feng et al, *Proc. Natl. Acad. Sci. USA* 2015, 112:E7073-7082; and Foss et al, *ACS Infect. Dis.* 2016, 2:500-508), raising questions as to the direct or indirect mechanism of inhibition of MmpL3. Recent literature reports (see e.g., Xu et al, *Proc. Nat. Acad. Sci. USA* 2017, 114:7993-7998) provided evidence of a direct interaction between MmpL3 and the inhibitor BM212 (see e.g., La Rosa et al, *Antimicrob. Agents Chemother.* 2012, 56:324-331), by showing that the [$^{14}$C]-labeled inhibitor bound to the purified MmpL3 protein from *Mycobacterium smegmatis* (Msmg). Further reports discuss development of a spheroplast-based flippase assay for MmpL3. Although informative in that this assay provided the first direct evidence of the build-up of TMM in the inner leaflet of the plasma membrane following MmpL3 inhibition, the cumbersome preparation of spheroplasts that this assay requires, and the fact that it does not readily distinguish between direct and indirect mechanisms of inhibition of the transporter, limits its usefulness for compound screening.

The present application discloses development of in vitro and whole cell-based assays enabling the identification of direct inhibitors of MmpL3 from Mtb, and their use to validate the interaction of five known MmpL3 inhibitors with the transporter. Biolayer interferometry- and surface plasmon resonance-based assays suggest that some inhibitors induce conformational changes in MmpL3. Limited proteolysis experiments further suggest that one of the most commonly identified resistance mutations in MmpL3 causes conformational changes in the protein, thereby providing a plausible mechanism through which missense mutations may confer cross-resistance to a broad variety of inhibitors.

The crystal structure of MmpL3 alone and in complex with SQ109, an adamantyl urea and indolecarboxamide (see e.g., Zhang et al, *Cell* 2019, 176:636-648) confirms a common inhibitor binding site located in the middle region of the transmembrane domain of MmpL3 (see e.g., Belardinelli et al, *ACS Infect. Dis.* 2016, 2:702-713) and provides a structural rationale for the functionality of the assays and methods described herein.

Compounds

The present application provides a compound of Formula I:

A-B-C or a salt thereof, wherein:
A is a detectable moiety;
B is a linking group; and
C is an MmpL3 inhibitor moiety.

In some embodiments, A is a fluorescent detectable moiety. In some embodiments, the fluorescent detectable moiety comprises a xanthene moiety, a BODIPY moiety (e.g., a BODIPY 493/503 moiety, a BODIPY FL moiety, a BODIPY FL-X moiety, and the like), an anthracene moiety, an anthraquinone moiety, an acridine moiety, or any combination thereof.

In some embodiments, the xanthene moiety is selected from the group consisting of a fluorescein moiety (e.g., a 6-carboxyfluorescein moiety, a carboxyfluorescein succinimidyl ester moiety, a fluorescein isothiocyanate, and the like), a rhodamine moiety (e.g., a carboxytetramethylrhodamine moiety, a tetramethylrhodamine moiety, a rhodamine 6G moiety, a rhodamine 123 moiety, a rhodamine B moiety, and the like), an Oregon green moiety (e.g., an Oregon Green 488 moiety, an Oregon Green 514 moiety, and the like), an eosin moiety (e.g., an eosin Y moiety, an eosin B moiety, and the like), and a Texas red moiety.

In some embodiments, the acridine moiety is selected from the group consisting of a proflavin moiety, an acridine orange moiety, and an acridine yellow moiety. In some embodiments, the fluorescent detectable moiety comprises a xanthene moiety or a BODIPY moiety. In some embodiments, the fluorescent detectable moiety comprises a xanthene moiety. In some embodiments, the fluorescent detectable moiety comprises a BODIPY moiety.

In some embodiments, A is a fluorescent detectable moiety selected from the group consisting of:

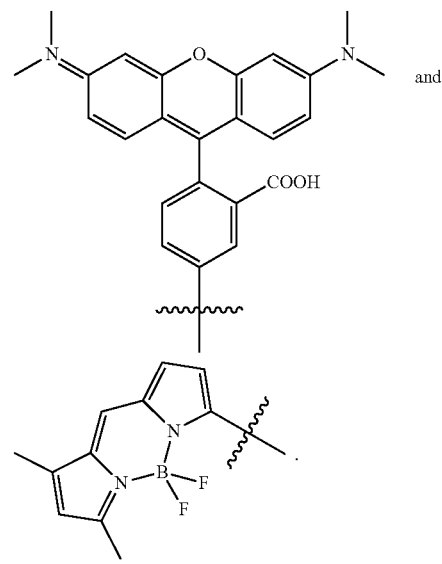

and wherein ∼∼∼∼ refers to the bond between A and B.

In some embodiments, A is:

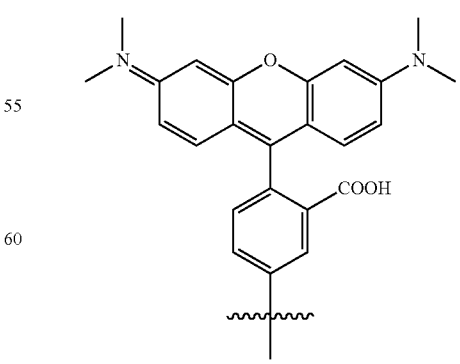

wherein ∼∼∼∼ refers to the bond between A and B.

In some embodiments, A is:

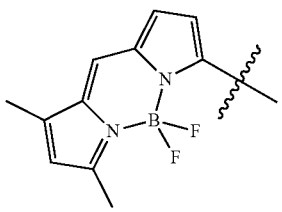

wherein ⁓⁓⁓ refers to the bond between A and B.

In some embodiments, B is a linking group comprising one or more alkylene groups, one or more C(O)NH groups, or one or more 5-10 membered heteroaryl rings, or any combination thereof.

In some embodiments, B is a linking group comprising one or more (e.g., 1, 2, 3, or 4) alkylene groups. In some embodiments, B is a linking group comprising one or more (e.g., 1, 2, 3, or 4) C(O)NH groups. In some embodiments, B is a linking group comprising one or more (e.g., 1, 2, 3, or 4) 5-10 membered heteroaryl rings. In some embodiments, B is a linking group comprising one or more (e.g., 1, 2, 3, or 4) alkylene groups and one or more (e.g., 1, 2, 3, or 4) C(O)NH groups. In some embodiments, B is a linking group comprising one or more (e.g., 1, 2, 3, or 4) alkylene groups and one or more (e.g., 1, 2, 3, or 4) 5-10 membered heteroaryl rings. In some embodiments, B is a linking group comprising one or more (e.g., 1, 2, 3, or 4) C(O)NH groups and one or more (e.g., 1, 2, 3, or 4) 5-10 membered heteroaryl rings. In some embodiments, B is a linking group comprising one or more (e.g., 1, 2, 3, or 4) alkylene groups, one or more (e.g., 1, 2, 3, or 4) C(O)NH groups, and one or more (e.g., 1, 2, 3, or 4) 5-10 membered heteroaryl rings. In some embodiments, each of the one or more alkylene groups is an independently selected $C_{1-10}$ alkylene group. In some embodiments, each of the one or more 5-10 membered heteroaryl rings is an independently selected 5-10 membered heteroaryl ring. In some embodiments, each of the heteroaryl rings is a 5-6 membered heteroaryl ring. In some embodiments, each heteroaryl ring is a triazolyl ring.

In some embodiments, B is a linking group comprising one or more $C_{1-10}$ alkylene groups, one or more C(O)NH groups, and one 5-10 membered heteroaryl ring. In some embodiments, B is a linking group comprising one, two, or three $C_{1-10}$ alkylene groups, one C(O)NH group, and one, two, or three 5-6 membered heteroaryl rings. In some embodiments, B is a linking group comprising one, two, or three $C_{1-10}$ alkylene groups, one C(O)NH group, and one 5-6 membered heteroaryl ring.

In some embodiments, B is a linking group selected from the group consisting of:
—C(O)NH—($C_{1-10}$ alkylene)-(5-6 membered heteroaryl)-($C_{1-10}$ alkylene)-; and
—($C_{1-10}$ alkylene)-C(O)NH—($C_{1-10}$ alkylene)-(5-6 membered heteroaryl)-($C_{1-10}$ alkylene)-.

In some embodiments, B is a linking group selected from the group consisting of:
—C(O)NH—($C_{1-6}$ alkylene)-(5-6 membered heteroaryl)-($C_{1-3}$ alkylene)-; and
—($C_{1-3}$ alkylene)-C(O)NH—($C_{1-3}$ alkylene)-(5-6 membered heteroaryl)-($C_{1-3}$ alkylene)-.

In some embodiments, B is a linking group selected from the group consisting of:

—C(O)NHCH$_2$CH$_2$CH$_2$CH$_2$CH$_2$CH$_2$-triazolyl-CH$_2$—; and

—CH$_2$CH$_2$C(O)NHCH$_2$CH$_2$CH$_2$-triazolyl-CH$_2$—.

In some embodiments, C is an MmpL3 inhibitor moiety selected from the group consisting of:

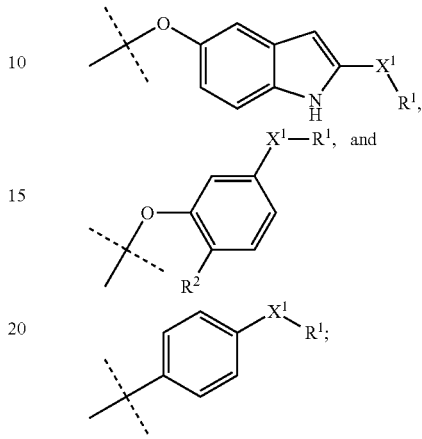

wherein:
------ refers to the bond between B and C;
$X^1$ is selected from the group consisting of C(O)NH, $C_{1-4}$ alkyl-C(O)NH, and NHC(O)NH;
$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups; and
$R^2$ is selected from the group consisting of C(O)$C_{1-4}$ alkyl and C(O)$C_{1-4}$ alkoxy. In some embodiments, C is

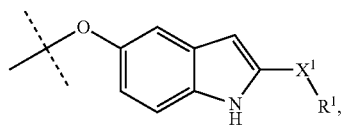

wherein:
------ refers to the bond between B and C;
$X^1$ is selected from the group consisting of C(O)NH, $C_{1-4}$ alkyl-C(O)NH, and NHC(O)NH; and
$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups.

In some embodiments, C is

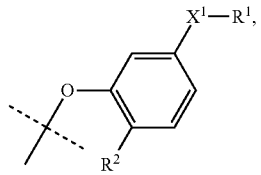

wherein:

------ refers to the bond between B and C;

$X^1$ is selected from the group consisting of C(O)NH, $C_{1-4}$ alkyl-C(O)NH, and NHC(O)NH;

$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups; and $R^2$ is selected from the group consisting of C(O)$C_{1-4}$ alkyl and C(O)$C_{1-4}$ alkoxy.

In some embodiments, C is

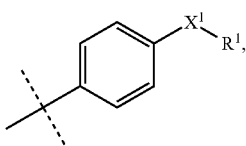

wherein:

------ refers to the bond between B and C;

$X^1$ is selected from the group consisting of C(O)NH, $C_{1-4}$ alkyl-C(O)NH, and NHC(O)NH; and $R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups.

In some embodiments, C is an MmpL3 inhibitor moiety selected from the group consisting of:

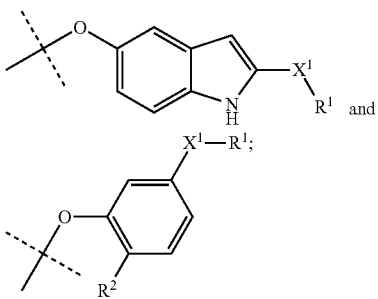

wherein:

------ refers to the bond between B and C;

$X^1$ is selected from the group consisting of C(O)NH, $C_{1-4}$ alkyl-C(O)NH, and NHC(O)NH;

$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups; and $R^2$ is selected from the group consisting of C(O)$C_{1-4}$ alkyl and C(O)$C_{1-4}$ alkoxy.

In some embodiments, $X^1$ is selected from the group consisting of C(O)NH, $CH_2$C(O)NH, and NHC(O)NH. In some embodiments, $X^1$ is selected from the group consisting of C(O)NH and NHC(O)NH. In some embodiments, $X^1$ is C(O)NH. In some embodiments, $X^1$ is $CH_2$C(O)NH. In some embodiments, $X^1$ is NHC(O)NH.

In some embodiments, C is

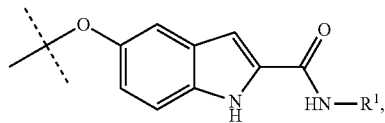

wherein:

------ refers to the bond between B and C; and $R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups.

In some embodiments, C is

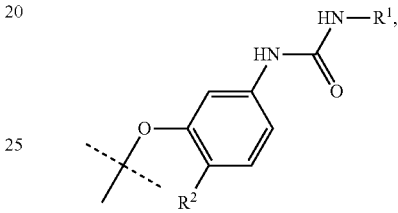

wherein:

------ refers to the bond between B and C;

$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups; and $R^2$ is selected from the group consisting of C(O)$C_{1-4}$ alkyl and C(O)$C_{1-4}$ alkoxy.

In some embodiments, C is

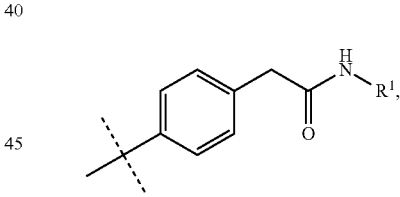

wherein:

------ refers to the bond between B and C;

$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups.

In some embodiments, $R^1$ is $C_{5-10}$ cycloalkyl, which is optionally substituted by 1, 2, or 3 independently selected $C_{1-4}$ alkyl groups. In some embodiments, $R^1$ is selected from the group consisting of cyclooctyl, bicyclo[3.1.1]heptyl, and adamantyl, each of which is optionally substituted by 1, 2, or 3 methyl groups. In some embodiments, $R^1$ is selected from the group consisting of cyclooctyl, trimethylbicyclo [3.1.1]heptyl, and adamantyl. In some embodiments, $R^1$ is cyclooctyl. In some embodiments, $R^1$ is adamantyl. In some embodiments, $R^1$ is trimethylbicyclo[3.1.1]heptyl.

In some embodiments, $R^2$ is C(O)$C_{1-4}$ alkoxy. In some embodiments, $R^2$ is C(O)OCH$_3$.

In some embodiments:

A is a fluorescent detectable moiety;

B is a linking group comprising one or more alkylene groups, one or more C(O)NH groups, and one or more 5-10 membered heteroaryl rings; and C is an MmpL3 inhibitor moiety selected from the group consisting of:

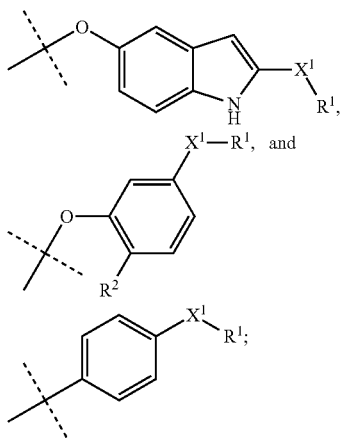

wherein:

------ refers to the bond between B and C;

$X^1$ is selected from the group consisting of C(O)NH, $C_{1-4}$ alkyl-C(O)NH, and NHC(O)NH;

$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups; and $R^2$ is selected from the group consisting of C(O)$C_{1-4}$ alkyl and C(O)$C_{1-4}$ alkoxy.

In some embodiments:

A is a fluorescent detectable moiety;

B is a linking group comprising one or more alkylene groups, one or more C(O)NH groups, and one or more 5-10 membered heteroaryl rings; and C is an MmpL3 inhibitor moiety selected from the group consisting of:

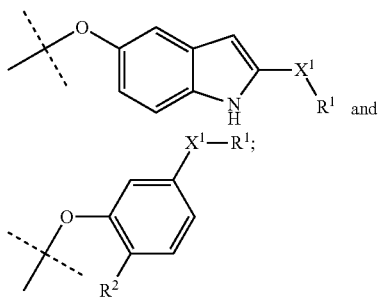

wherein:

------ refers to the bond between B and C;

$X^1$ is selected from the group consisting of C(O)NH and NHC(O)NH;

$R^1$ is selected from the group consisting of $C_{5-10}$ cycloalkyl, $C_{6-10}$ aryl, —$C_{1-4}$ alkyl-$C_{5-10}$ cycloalkyl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 independently selected $C_{1-4}$ alkyl groups; and $R^2$ is selected from the group consisting of C(O)$C_{1-4}$ alkyl and C(O)$C_{1-4}$ alkoxy.

In some embodiments:

A is a fluorescent detectable moiety comprising a xanthene moiety or a BODIPY moiety:

B is a linking group comprising one or more $C_{1-10}$ alkylene groups, one or more C(O)NH groups, and one 5-6 membered heteroaryl ring; and C is an MmpL3 inhibitor moiety selected from the group consisting of:

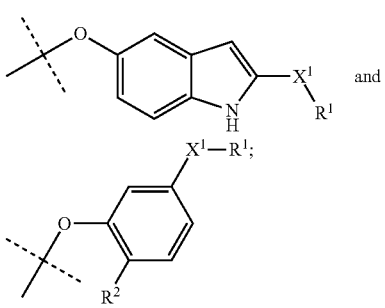

wherein:

------ refers to the bond between B and C;

$X^1$ is selected from the group consisting of C(O)NH and NHC(O)NH;

$R^1$ is $C_{5-10}$ cycloalkyl, which is optionally substituted by 1, 2, 3, or 4 independently selected $C_{1-4}$ alkyl groups; and $R^2$ is C(O)$C_{1-4}$ alkoxy.

In some embodiments:

A is a fluorescent detectable moiety comprising a xanthene moiety or a BODIPY moiety:

B is a linking group comprising one or more $C_{1-10}$ alkylene groups, one or more C(O)NH groups, and one 5-6 membered heteroaryl ring; and C is an MmpL3 inhibitor moiety selected from the group consisting of:

and

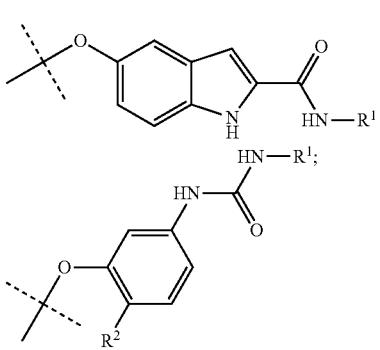

wherein:

------ refers to the bond between B and C;

$R^1$ is $C_{5-10}$ cycloalkyl, which is optionally substituted by 1, 2, 3, or 4 independently selected $C_{1-4}$ alkyl groups; and $R^2$ is C(O)$C_{1-4}$ alkoxy.

In some embodiments:

A is a fluorescent detectable moiety selected from the group consisting of:

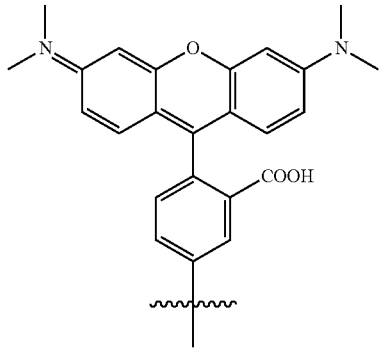

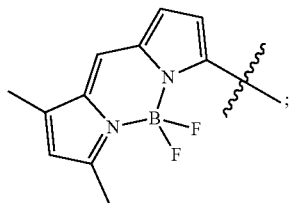

wherein ⌇⌇⌇ refers to the bond between A and B;

B is a linking group comprising one or more $C_{1-10}$ alkylene groups, one or more C(O)NH groups, and one 5-6 membered heteroaryl ring; and C is an MmpL3 inhibitor moiety selected from the group consisting of:

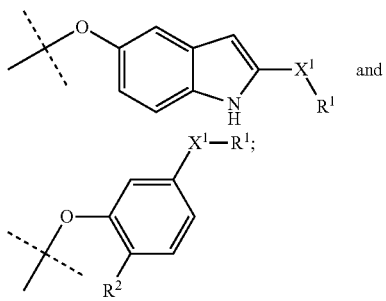

wherein:

------ refers to the bond between B and C;

$X^1$ is selected from the group consisting of C(O)NH and NHC(O)NH;

$R^1$ is $C_{5-10}$ cycloalkyl, which is optionally substituted by 1, 2, 3, or 4 independently selected $C_{1-4}$ alkyl groups; and $R^2$ is C(O)$C_{1-4}$ alkoxy.

In some embodiments:

A is a fluorescent detectable moiety selected from the group consisting of:

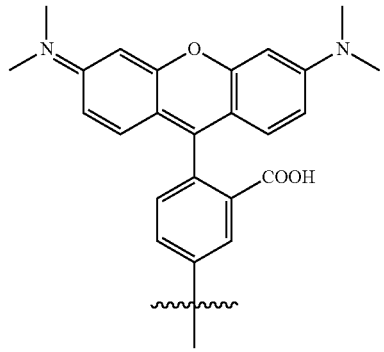

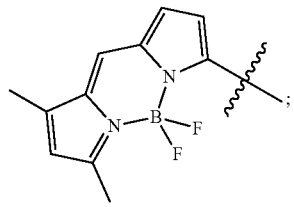

wherein ⌇⌇⌇ refers to the bond between A and B;

B is a linking group selected from the group consisting of —C(O)NH—($C_{1-6}$ alkylene)-(triazolyl)-($C_{1-3}$ alkylene)- and —($C_{1-3}$ alkylene)-C(O)NH—($C_{1-3}$ alkylene)-(triazolyl)-($C_{1-3}$ alkylene)-; and C is an MmpL3 inhibitor moiety selected from the group consisting of:

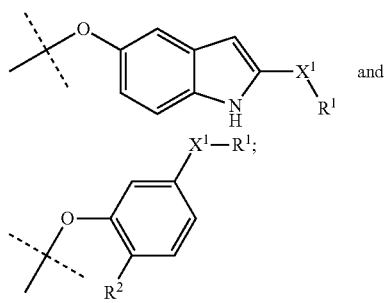

wherein:

------ refers to the bond between B and C;

$X^1$ is selected from the group consisting of C(O)NH and NHC(O)NH;

$R^1$ is selected from the group consisting of cyclooctyl, bicyclo[3.1.1]heptyl, and adamantyl, each of which is optionally substituted by 1, 2, or 3 methyl groups; and $R^2$ is C(O)OCH$_3$.

In some embodiments:

A is a fluorescent detectable moiety selected from the group consisting of:

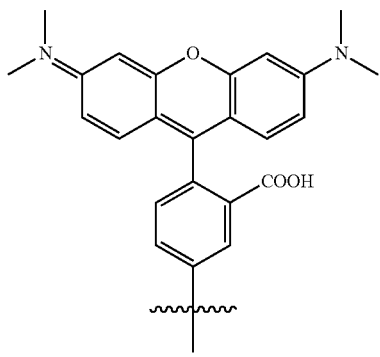

and

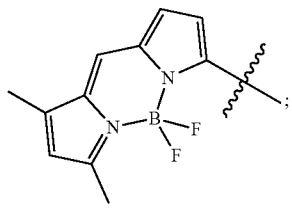

wherein ∿∿∿ refers to the bond between A and B; B is a linking group selected from the group consisting of —C(O)NH—(C$_{1-6}$ alkylene)-(triazolyl)-(C$_{1-3}$ alkylene)- and —(C$_{1-3}$ alkylene)-C(O)NH—(C$_{1-3}$ alkylene)-(triazolyl)-(C$_{1-3}$ alkylene)-; and C is an MmpL3 inhibitor moiety selected from the group consisting of:

and

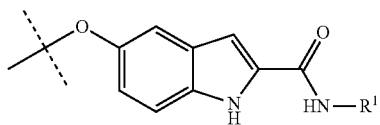

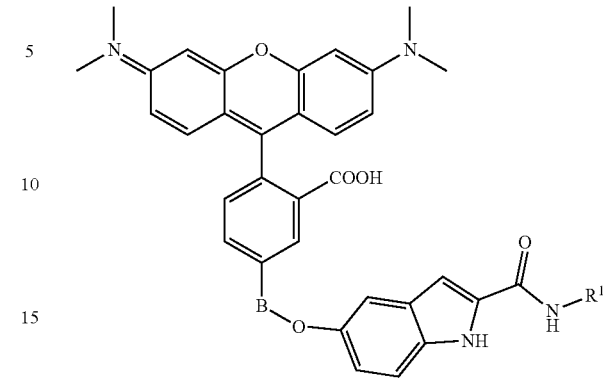

wherein:

------ refers to the bond between B and C; and

R$^1$ is selected from the group consisting of cyclooctyl, bicyclo[3.1.1]heptyl, and adamantyl, each of which is optionally substituted by 1, 2, or 3 methyl groups.

In some embodiments, the compound of Formula I is a compound of Formula II:

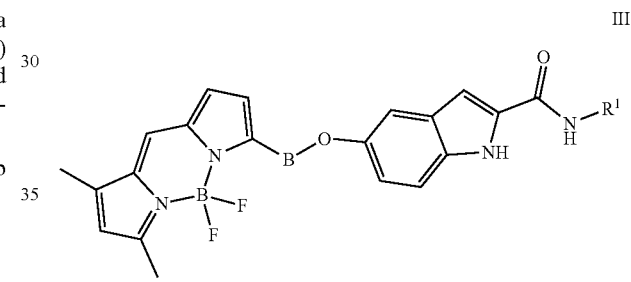

or a salt thereof, wherein variables B and R$^1$ are defined according to the definitions provided herein for compounds of Formula I.

In some embodiments, the compound of Formula I is a compound of Formula III:

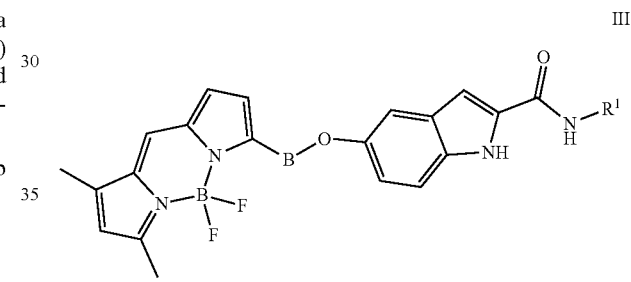

or a salt thereof, wherein variables B and R$^1$ are defined according to the definitions provided herein for compounds of Formula I.

In some embodiments, the compound of Formula I is a compound of Formula IV:

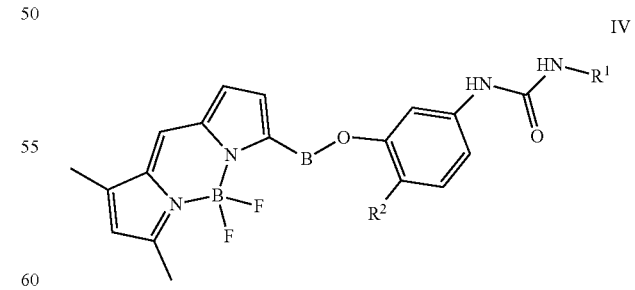

or a salt thereof, wherein variables B and R$^1$ are defined according to the definitions provided herein for compounds of Formula I.

In some embodiments, the compound provided herein is selected from the group consisting of:

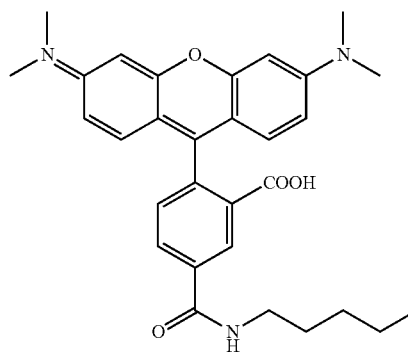
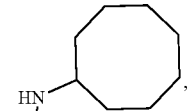
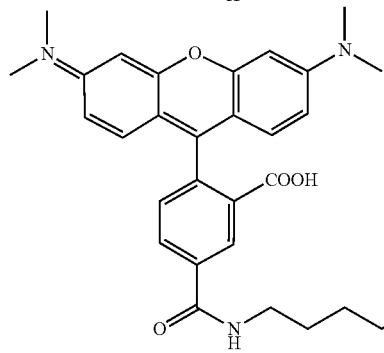
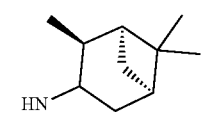
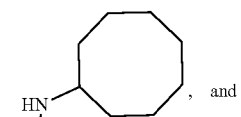
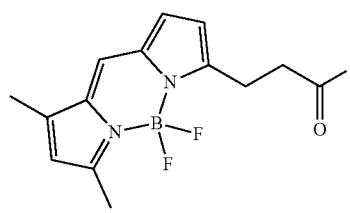
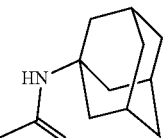
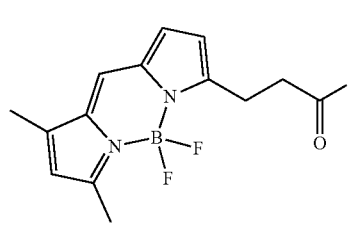
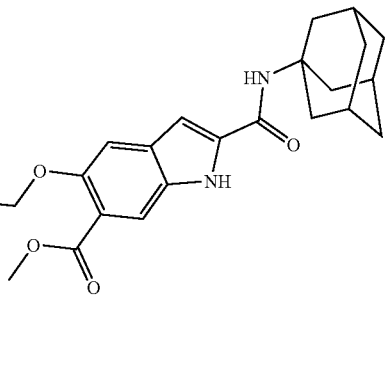

or a salt thereof.

Synthesis

Indolecarboxamide (IC)-based probes were designed using lipophilic head groups (e.g., cyclooctyl, isocampheyl) that are known to promote high anti-mycobacterial activity through MmpL3 inhibition (see e.g., Franz et al, *Bioorg. Med. Chem.* 2017, 25:3746-3755). Structure-activity relationships of the IC scaffold have shown that substitution at the C5-position on the indole ring is well tolerated with respect to antimycobacterial activity (see e.g., Onajole et al., *J. Med. Chem.* 2013, 56:4093-4103; and Stec et al., *J. Med. Chem.* 2016, 59:6232-6247). Detectable functional groups (e.g., fluorescent groups) were linked through the indole.

Urea-based inhibitors have been reported as effective anti-tubercular agents acting through the inhibition of the MmpL3 transporter (see e.g., Grzegorzewicz et al., *Nat. Chem. Biol.* 2012, 8:334-341). Adamantyl urea-based methyl salicylate (AU) was reported with a potent Mtb MIC value of 0.4 µg/mL (see e.g., Brown et al., *Bioorg. Med. Chem.* 2011, 19:5585-5595). Representative fluorescent detectable agents (TAMRA- and BODIPY-based) were selected with unique absorption and emission spectra in the orange/red and green regions of the electromagnetic spectrum to exemplify a breadth of utility and to circumvent any non-specific absorption or emission quenching from other biological or chemical components.

MmpL3 chemical probes, Compounds 1-4, were synthesized according to Scheme 1. ICs (1 and 2 of Scheme 1) and AU (5 of Scheme 1) were synthesized according to previously reported methods. In brief, the free hydroxyl group on either IC or AU was alkylated using propargyl bromide. The fluorophore was attached via click reaction conditions, affording final fluorescent MmpL3 chemical probes (Compounds 1-4; i.e., North 100, North 114, North 131, and North 132, respectively). Reagents and conditions of Scheme 1: (a) propargyl bromide, $K_2CO_3$, DMF, room temperature, 12 hr; (b) TAMRA- or BODIPY-linked azide, $CuSO_4$, sodium ascorbate, DMSO, room temperature, overnight.

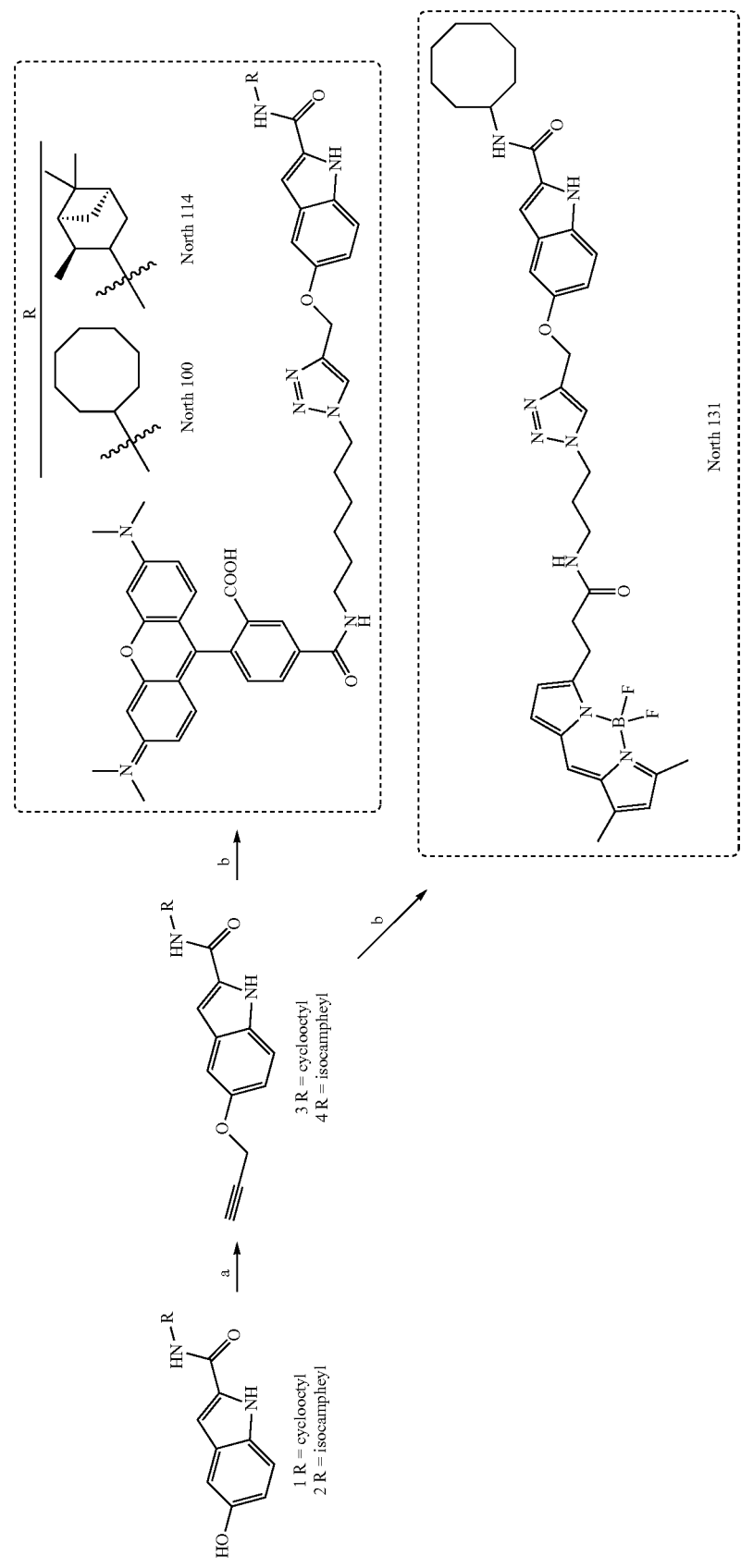

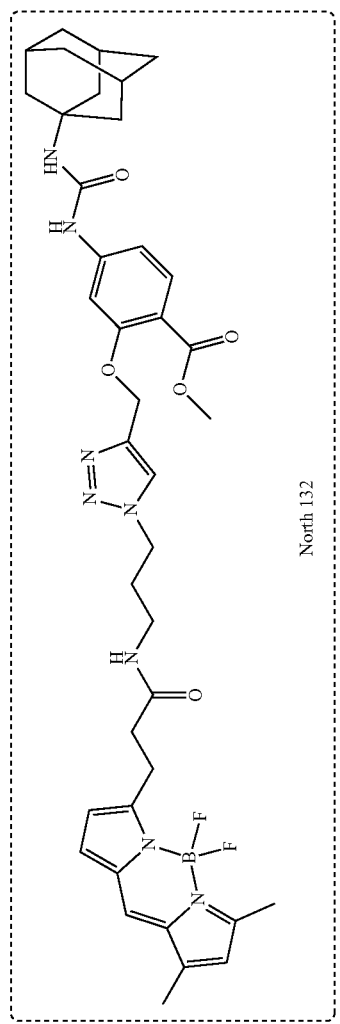
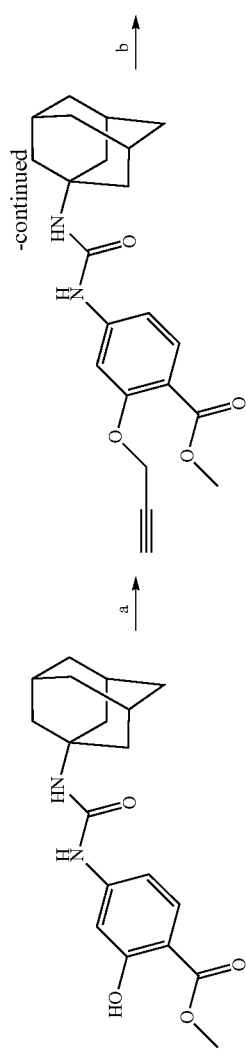

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$—includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "BODIPY" refers to fluorescent moiety having a 4,4-difluoro-4-bora-3a,4a-diaza-s-indacene core, as shown below. In some embodiments, the fluorescent moiety provided herein is a substituted BODIPY moiety.

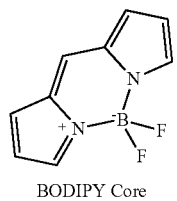

BODIPY Core

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl" refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and iso-propoxy), butoxy (e.g., n-butoxy and tert-butoxy), and the like. In some embodiments, the alkyl group has 1 to 6, 1 to 4, or 1 to 3 carbon atoms.

As used herein, the term "aryl" refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 10 carbon atoms (i.e., a $C_{6-10}$ aryl). In some embodiments, the aryl group is a substituted or unsubstituted phenyl.

As used herein, "cycloalkyl" refers to non-aromatic cyclic hydrocarbons including cyclized alkyl and/or alkenyl groups. Cycloalkyl groups can include mono- or polycyclic groups (e.g., having 2, 3 or 4 fused rings; bicyclic cycloalkyl groups; and tricyclic cycloalkyl groups) and spirocycles. Cycloalkyl groups can have 5, 6, 7, 8, 9, or 10 ring-forming carbons (i.e., a $C_{5-10}$ cycloalkyl group). In some embodiments, the cycloalkyl is cyclopentyl, cyclohexyl, cycloheptyl, cyclooctyl, cyclononyl, or adamantyl. In some embodiments, the cycloalkyl has 5-10 ring-forming carbon atoms (i.e., a $C_{5-10}$ cycloalkyl group).

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2, 4-triazole, 1H- and 2H-isoindole, and 1H- and 2H-pyrazole. Tautomeric forms can be in equilibrium or sterically locked into one form by appropriate substitution.

All compounds and salts thereof can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The present application further provides salts (e.g., pharmaceutically acceptable salts) of the compounds provided herein. The phrase "pharmaceutically acceptable" is employed herein to refer to those compounds and compositions, which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977).

Conventional methods for preparing salt forms are described, for example, in Handbook of Pharmaceutical Salts: Properties, Selection, and Use, Wiley-VCH, 2002.

Methods of Use

The present application further provides methods of identifying an inhibitor of MmpL3. In some embodiments, the method is an in vitro method. In some embodiments, the method is an in vivo method.

In some embodiments, the method comprises:

i) contacting a cell or a gene with a compound provided herein, or a salt thereof, to form a compound-MmpL3 complex in the cell or gene;

ii) contacting the cell or gene with a test compound; and iii) measuring displacement of the compound from the compound-MmpL3 complex and formation of a test compound-MmpL3 complex in the cell or gene.

In some embodiments, the method comprises contacting the compound and test compound with a cell. In some embodiments, the cell is selected from the group consisting of an Msmg cell and an Mtb cell. In some embodiments, the cell is an Msmg cell (e.g., a Msmg mc$^2$155 cell). In some embodiments, the cell is an Mtb cell (e.g., an Mtb H37Rv strain mc$^2$6206 cell).

In some embodiments, the method comprises contacting the compound and test compound with a gene. In some embodiments, the gene is an Mtb mmpL3 gene (e.g., mmpL3tbI). In some embodiments, the gene is an Mtb mmpL3 WT gene. In some embodiments, the gene is an Mtb mmpL3 mutant gene. In some embodiments, the mutant is selected from the group consisting of G253E, S288T, S309C, T311I, Q372R, L567P, S591I, F644C, V684G, and V684A.

In some embodiments, step i) and step ii) are performed simultaneously (e.g., the cell is contacted with the compound provided herein and the test compound simultaneously). In some embodiments, step i) and step ii) are performed sequentially (e.g., the cell is first contacted with the compound provided herein, and after a time sufficient to allow formation of the compound-MmpL3 complex, the cell is contacted with the test compound).

In some embodiments, the measuring comprises quantitative measuring displacement of the compound from the compound-MmpL3 complex and formation of a test compound-MmpL3 complex in the cell. In some embodiments, the displacement is measured by comparing the relative fluorescence intensity (RFI) of the cell after contacting the cell with the compound provided herein, or a salt thereof, to form the compound-MmpL3 complex in the cell (i.e., the initial RFI), with the RFI after contacting the cell with a test compound.

In some embodiments, displacement is identified by a decrease in the initial RFI upon contacting the cell with the test compound. In some embodiments, the RFI is decreased by about 1% or greater, for example, by about 10% or greater, by about 20% or greater, by about 30% or greater, by about 40% or greater, by about 50% or greater, by about 60% or greater, by about 70% or greater, by about 80% or greater, by about 90% or greater, by about 95% or greater, by about 99% or greater. In some embodiments, the RFI is decreased by about 1% to about 99%, for example, about 1% to about 95%, about 1% to about 90%, about 1% to about 75%, about 1% to about 50%, about 1% to about 25%, about 1% to about 10%, about 10% to about 99%, about 10% to about 95%, about 10% to about 90%, about 10% to about 75%, about 10% to about 50%, about 10% to about 25%, about 25% to about 99%, about 25% to about 95%, about 25% to about 90%, about 25% to about 75%, about 25% to about 50%, about 50% to about 99%, about 50% to about 95%, about 50% to about 90%, about 50% to about 75%, about 75% to about 99%, about 75% to about 95%, about 75% to about 90%, about 90% to about 99%, about 90% to about 95%, or about 95% to about 99%.

In some embodiments, the measuring comprises qualitative measuring displacement of the compound from the compound-MmpL3 complex and formation of a test compound-MmpL3 complex in the cell. In some embodiments, the displacement is measured by flow cytometry. In some embodiments, the method provided herein is a high throughput screening method. In some embodiments, the measuring comprises imaging the cell. In some embodiments, the imaging comprises fluorescence imaging (e.g., fluorescence microscopy).

Compositions

The compounds and salts provided herein can be administered in the form of compositions. In some embodiments, the compositions comprise a compound provided herein, or a salt thereof, in combination with one or more carriers (e.g., excipients). In making the compositions provided herein, the compound provided herein is typically mixed with an excipient, diluted by an excipient, or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of powders, suspensions, emulsions, solutions, syrups, aerosols, and sterile injectable solutions.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

General Methods and Materials

Reagents and Chemicals

All reagents were purchased from Sigma Aldrich. All chemicals were reagent grade and used without further purification. Mass Spectra was acquired on Applied Biosystems 3200 Q trap LC/MS/MS system. HPLC purity analysis was performed on an Agilent Technologies 1260 Infinity using a 50×3.0 mm Kinetex 5 um EVo C18 100 Å chromatography column with a gradient mobile phase with flow rate of 1 mL/min for 8 min with PDA detector.

Gradient conditions for Compound 1 and Compound 2: solvent A (0.1% formic acid in water) and solvent B (0.1% formic acid in MeOH): 0-1.00 min 95% solvent A, 1-8.00 min solvent 0-70% solvent B (linear gradients).

Gradient conditions for Compound 3 and Compound 4: solvent A (0.1% formic acid in water) and solvent B (0.1% Formic acid in MeOH): 0-1.00 min 95% solvent A, 1-9.00 min solvent 0-70% solvent B (linear gradients).

MmpL3 Inhibitor Synthesis

Indole-2-carboxamides and methyl 1-(1-adamantyl)-3-(4-aminosalicylate)urea were synthesized according to previously reported methods (see e.g., Franz et al., *Bioorg. Med. Chem.* 2017, 25:3746-3755; and Brown et al., *Bioorg. Med. Chem.* 2011, 19:5585-5595).

Bacterial Strains and Growth Conditions

The avirulent auxotrophic Mtb H37Rv strain mc$^2$6206 (ΔpanCDΔleuCD) was grown at 37° C. in Middlebrook 7H9-OADC-0.05% tyloxapol supplemented with 0.2% casaminoacids, 48 µg/mL pantothenate and 50 µg/mL L-leucine or on similarly supplemented Middlebrook 7H11-OADC agar medium. Msmg mc$^2$155 was grown in Middlebrook 7H9 broth (Difco) with 10% albumin-dextrose-catalase (ADC) supplement and 0.05% Tween 80, Luria Bertani (LB) medium (10 g/L Bacto-tryptone, 5 g/L yeast extract and 5 g/L NaCl) (Difco) and on 7H11-ADC or LB agar at 37° C. Kanamycin (Kan; 25 µg/mL), streptomycin (Str, 20 µg/mL), and hygromycin (Hyg; 50 µg/mL) were added as needed.

Expression of Mutated Variants of MmpL3tb

Seventy-seven mutated variants of MmpL3tb were tested for susceptibility to MmpL3 inhibitors, including C-terminally truncated and point-mutated MmpL3tb variants generated according to previous reports (see e.g., Belardinelli et al, *ACS Infect. Dis.* 2016, 2:702-713; total of 59 variants). Other mutants (L189A; L189R; G253E; G253R; G253W; S288T; T311I; Q372R; L567P; S591I; S591W; S591G; F644C; F644Y; V684A; V684G; V684I; V684W) were generated using a standard two-step PCR overlap method or PCR-amplified from the genomic DNA of AU1235-, NITD-304- and NITD-349-Mtb spontaneous resistant mutants. All variants were cloned in the mycobacterial expression mycobacterial plasmid, pMVGH1, under control of the hsp60 promoter and expressed in the background of a Msmg mmpL3 deletion mutant (MsmgΔmmpL3) according to reported procedures (see e.g., Grzegorzewicz et al, *Nat. Chem. Biol.* 2012, 8:334-341; and Belardinelli et al, *ACS Infect. Dis.* 2016, 2:702-713). MsmgΔmmpL3/pMVGH1-mmpL3tb-gfp was similarly generated by expressing in MsmgΔmmpL3 the mmpL3 gene from Mtb fused to gfp at the 3'-end.

Drug-Susceptibility Testing

The susceptibility of MsmgΔmmpL3 expressing different variants of MmpL3tb to inhibitors and control drugs was determined in 96-well microtiter plates at 37° C. in 7H9-ADC-0.05% Tween 80 medium using the resazurin blue test (see e.g., Martin et al, *Antimicrob. Agents Chemother.* 2003, 47:3616-3619).

Whole Cell Radiolabeling Experiments

Radiolabeling of Msmg and Mtb (0.5 μCi/mL; specific activity, 54.3 Ci/mol, Perkin Elmer) was performed for 3 h (Msmg) or 24 h (Mtb) at 37° C. with shaking. MmpL3 inhibitors and inhibitor probes (Compounds 1-4) were added at the same time as [1,2-$^{14}$C]acetic acid to the bacterial cultures.

Lipid and Mycolic Acid Analyses

Total lipids extraction from bacterial cells and preparation of fatty acid and mycolic acid methyl esters from extractable lipids and delipidated cells were performed according to previously reported procedures (see e.g., Grzegorzewicz et al, *Nat. Chem. Biol.* 2012, 8:334-341). [1,2-$^{14}$C]acetic acid-derived lipids and fatty acid/mycolic acid methyl esters were separated by TLC on aluminum-backed silica gel 60-precoated plates $F_{254}$ (E. Merck) and revealed by PhosphorImaging.

Membrane Potential and Electrochemical Proton Gradient Measurements in Intact Mtb Cells The effects of inhibitors on the transmembrane potential (ΔΨ) and transmembrane electrochemical proton gradient (ΔpH) of intact Mtb H37Rv $mc^2$6206 cells were determined by fluorescence quenching of the membrane potential-sensitive probe 3-3'Diethyloxacarbocyanine iodide [$DiOC_2(3)$] (ThermoFisher) and the pH-sensitive probe 5-chloromethylfluorescein diacetate (CMFDA) (ThermoFisher), respectively, according to previous reports (see e.g., Foss et al, *ACS Infect. Dis.* 2016, 2:500-508). For ΔΨ measurements, Mtb cells were labeled with 60 μM $DiOC_2$ in PBS supplemented with 50 mM KCl, pH 7.2, for 4 hours at 37° C. For ΔpH measurements, Mtb cells were labeled with 10 μM CMFDA in PBS, pH 7.0, for 4 hours at 37° C. Changes in fluorescence due to the disruption of ΔΨ or ΔpH upon inhibitor treatment were monitored for 30 minutes with a fluorescence spectrophotometer (Victor X5, PerkinElmer). $DiOC_2(3)$ was excited at 485 nm, and emission was measured at 615 and 535 nm. The ratio of fluorescence intensity at 615 nm vs 535 nm is relative to the strength of ΔΨ. The excitation wavelengths for the ΔpH assay were 440 and 490 nm and fluorescence emission was measured at 520 nm. The pH of the bacterial cytoplasm was measured by calculating the ratio of fluorescence intensity excited at 490 vs 440 nm.

Microscopy

MsmgΔmmpL3/pMVGH1-mmpL3tb-gfp cultures grown to exponential phase and treated for 4 h with 2 μM of Compound 1 and Compound 2 at 37° C. were collected, washed twice in phosphate-buffered saline containing 0.05% Tween 80, and fixed in freshly prepared 2% paraformaldehyde for 30 min at room temperature. Approximately $10^6$ cells were next transferred to a glass slide by Cytospin, mounted with Fluoro-Gel (Electron Microscopy Science) and visualized using a KEYENCE BZ-X700 fluorescence microscope. Alternatively, cells were visualized using an Olympus FV-1000 confocal microscope. Multiple independent experiments were performed and images from one representative experiment are shown.

MmpL3tb and MmpL3tb(G253E) Purification

To purify MmpL3tb and its G253E variant for BLI assays, MsmgΔmmpL3/pMVGH1-mmpL3tb and MsmgΔmmpL3/pMVGH1-mmpL3tb(G253E) cells (see e.g., Grzegorzewicz et al., Nat. Chem. Biol. 2012, 8:334-341) were grown in one liter of 7H9-ADC medium supplemented with 0.2% glycerol, 0.05% Tween-80, 25 μg/mL kanamycin, 50 μg/mL hygromycin B for 48 hours at 30° C. with shaking. Cells were collected by centrifugation and resuspended in 20 mL of TM Buffer (10 mM Tris pH 8.0, 1 mM $MgCl_2$) supplemented with 100 μg/mL DNase I and 1 mM PMSF, prior to breaking using French Press at 20,000 psi. Unbroken cells were removed by centrifugation at 4,000×g, and membranes collected by ultracentrifugation at 185,000×g, at 4° C. for 1 hour. Upon solubilization of the membrane pellets for 4-12 hours at 4° C. in TS Buffer (10 mM Tris pH 8.0, 150 mM NaCl, 0.5% n-dodecyl-β-D-maltoside [DDM]), the insoluble material was removed by ultracentrifugation at 185,000×g, at 4° C. for 1 hour, and the final NaCl concentration of the supernatant was increased to 200 mM. Solubilized membrane proteins were first passed through a HiTrap Q-FF (GE Healthcare) anion exchange column at a flow rate of 0.5 mL/min. The flow-through was collected and adjusted to 400 mM NaCl and 10 mM imidazole (final concentrations) prior to loading onto His-Bind affinity resin (Novagen). Wash solutions consisted of TW buffer (10 mM Tris pH 8.0, 400 mM NaCl, 20 mM imidazole, 0.03% DDM) followed by HW buffer (20 mM HEPES pH 8.0, 400 mM NaCl, 20 mM imidazole, 0.2% Triton X-100). MmpL3tb was finally eluted with HE Buffer (20 mM HEPES pH 8.0, 400 mM NaCl, 500 mM imidazole, 0.2% Triton X-100).

For the flow bead assay, MmpL3tb-GFP was purified from MsmgΔmmpL3/pMVGH1-mmpL3tb-gfp as follows. Cells grown at 32° C. in 7H9-ADC-Tween 0.05% containing hygromycin and kanamycin to an $OD_{600}$ of 0.8 were collected and resuspended in 50 mM Tris-HCl (pH 7.5) buffer containing 150 mM NaCl, protease cocktail inhibitors (Sigma-Aldrich) and Dnase I. Cells were broken by bead beating and unbroken cells removed by centrifugation at 6,000×g for 20 min. Total membrane fractions were isolated by ultracentrifugation at 100,000×g for 1 hour at 4° C. and resuspended in 50 mM Tris-HCl (pH 7.5) buffer containing 150 mM NaCl, 10% glycerol and 1% n-dodecyl β-D-malto-pyranoside (DDM). After removal of the insoluble fraction by ultracentrifugation, solubilized proteins were loaded onto a HisTrap™ column (GE Healthcare) and MmpL3tb-GFP purified by FPLC using standard protocols modified to include 0.1% DDM in the elution buffer. MmpL3tb-GFP-containing fractions were pooled, run through a PD10 desalting column (GE Healthcare), and finally concentrated using Amicon ultra-4 centrifugal filter units (MWCO 30 kDa; Sigma).

Binding of Purified MmpL3tb to Flow Beads and Competition Binding Assays with Inhibitor Probe(s)

Purified MmpL3tb-GFP and MmpL3tb were coated onto goat anti-mouse IgG (H&L)-coated polystyrene particles (Spherotech) previously treated with a mouse anti-His IgG antibody (Sigma). To assess fluorescent probe binding and for competition binding assays, MmpL3tb- and MmpL3tb-GFP-coated beads were incubated for 15 min at room temperature with different concentrations of the probes in the presence or absence of test inhibitors. After three washes in PBS pH 7.0-5% glycerol, the TAMRA and BODIPY FL mean fluorescence intensities of the beads was analyzed by flow cytometry on a Cytek Aurora Spectral cytometer. Flow Cytometry Standard (FCS) file data were analyzed using Flowjo® software (Treestar Inc., Ashland, Oreg.).

Competition Binding Assays Using Intact Msmg Cells

Competition binding assays in intact MsmgΔmmpL3/pMVGH1-mmpL3tb bacilli were conducted by treating the cells with 4 μM of probe Compound 2 or Compound 1 for one hour at 37° C., prior to washing the cells twice with 7H9-ADC-0.05% Tween 80 and resuspending them with different concentrations of the test compounds for another hour at 37° C. Treated cells washed with 7H9-ADC-0.05% Tween 80 and fixed with 2% paraformaldehyde were finally resuspended in PBS-0.05% Tween 80 and subjected to flow cytometry analysis as described above.

Biolayer Interferometry

Biolayer interferometry was performed using AR2G sensors loaded with purified MmpL3tb on an Octet RED96 instrument (ForteBIO). Sensors were hydrated for 1 hour and then activated for 600 seconds with 20 mM 1-ethyl-3-(-3-dimethylaminopropyl) carbodiimide hydrochloride (EDC) and 10 mM Sulfo-N-hydroxysuccinimide (Sulfo-NHS) (AR2G Reagent Kit, ForteBIO). Activated sensors were loaded in wells containing the purified protein in sodium acetate buffer, pH 4.0, then quenched for 500 seconds in ethanolamine, pH 8.0, and finally returned to assay buffer (20 mM HEPES-KOH pH 8.0, 150 mM NaCl, 0.2% Triton X-100). A second set of sensors, devoid of MmpL3tb protein, was activated as above and then quenched to serve as an empty sensor control for double-subtraction data processing.

BLI binding assays were performed as follows: After sensor equilibration for 250 seconds, a baseline was established in assay buffer for 60 seconds. Two-fold dilutions of compounds were then scanned for interaction with the proteins. Upon association of the test compounds for 30 seconds, sensors were returned to the baseline well for dissociation for 60 seconds. Sensors were dipped into fresh assay buffer and allowed to equilibrate for 250 seconds between two binding assays. Sensors were oriented so that a protein-loaded sensor was dipped into fresh assay buffer while another protein-loaded sensor was incubated with the test compounds (first reference). The entire assay was repeated with the set of sensors devoid of MmpL3tb protein using the same compound plate after the assays with loaded sensors were complete (second reference). All assay steps were performed in the Octet RED96 instrument at 25° C. under agitation (500 rpm). Assay development and data acquisition was performed using the BLI Acquisition Software 9.0.0.37 (ForteBIO). Data were processed and binding curves fit using the BLI Analysis Software 9.0.0.12 (ForteBIO).

Surface Plasmon Resonance

For the amino-coupling of MmpL3tb, CM5 chip surfaces were activated with 0.05 M N-hydroxysuccinimide and 0.2 M N-ethyl-N-(3-diethylaminopropyl)carbodiimide (BIAcore). MmpL3tb was injected over surfaces immediately after activation. After immobilization, the excess of reactive groups was blocked by injecting 0.5 M ethanolamine HCl (pH 8.0). Immobilization and subsequent binding experiments were conducted in running buffer containing 25 mM HEPES-KOH (pH 7.0), 150 mM NaCl, 0.2% Triton X-100 (HEPES-TX). The CM5 chip contained four chambers, one of which contained the immobilized MmpL3tb (ligand), whereas the second (control surface) was activated and processed in the same way but protein was omitted during the immobilization step. For kinetic modeling, the simplest models that would be compatible with one or two distinct events during both inhibitor binding and dissociation were considered. The four models are: (i) Simple 1:1 binding model; (ii) Heterogeneous Ligand (HL), in which different protein populations on chip surface have different kinetic properties; (iii) Two-State Reaction or ligand-induced conformational change, wherein conformational change occurs on the same time scale as ligand binding; and (iv) Bivalent Analyte, where multiple analytes bind independently at nonidentical sites. Distinguishing between these models is possible if the data are fit globally; that is, by fitting all sensorgrams obtained at various protein concentrations using the same set of parameters (see e.g., Tikhonova et al, *Proc. Natl. Acad. Sci. USA*, 2009, 106:16416-16421).

Limited Proteolysis of MmpLt3b

Purified protein was diluted in assay buffer (150 mM NaCl, 20 mM HEPES-KOH pH 8.0, 0.2% Triton X-100) to a final concentration of 100 nM. Compounds were added to the protein sample to a final concentration of 200 µM (solubility permitting) in DMSO (5% final concentration) and allowed to incubate for 5 min at room temperature prior to digestion with 0.01, 0.1 and 1.0 µg/mL trypsin for 30 min at 37° C. Protein samples were analyzed by SDS-PAGE and visualized by silver staining.

Assay for Succinate-Driven Proton Translocation into *E. coli* and Mtb Inverted Membrane Vesicles (IMVs)

Succinate-driven proton translocation assays with the fluorescent substrate ACMA were conducted as previously described (see e.g., Li et al. *J. Med. Chem.* 2014, 57: 3126-3139) to determine the effect of MmpL3 inhibitors on the electrochemical proton gradient of Mtb H37Rv mc²6206 and *E. coli* BL21(DE3) IMVs. IMVs (0.18 mg/mL membrane proteins) were pre-incubated at 37° C. in 10 mM HEPES-KOH pH 7.5, 100 mM KCl, 5 mM $MgCl_2$ containing 2 µM ACMA and the baseline monitored for 10 min with a fluorescence spectrophotometer (Victor X5, PerkinElmer). The reaction was then initiated by adding 5 mM succinate. Upon stabilization of the signal, control compounds (INH, RIF, nigericin), MmpL3 inhibitors, or diluent (0.2% DMSO or water) were added and proton translocation monitored fluorimetrically. The excitation and emission wavelengths were 410 nm and 480 nm, respectively.

Example 1. General Procedures for Synthesis of Alkyne Intermediates

To a solution of the indole-2-carboxamide or urea-based analog (1 equiv.) in anhydrous dimethylformamide (DMF) (for ICs) or tetrahydrofuran (THF) (for urea-based analog) at room temperature was added potassium carbonate (1 equiv.). Next, propargyl bromide (1.2 equiv.) was added dropwise and the resulting mixture was stirred for 12 h. Water was added and the mixture was extracted with EtOAc (3×10 mL). The organic layers were separated, washed with brine, dried over anhydrous $Na_2SO_4$, filtered, and concentrated under reduced pressure. The residue was purified by flash chromatography on silica gel using EtOAc/hexane gradient.

Intermediate 1. N-cyclooctyl-5-(prop-2-yn-1-yloxy)-1H-indole-2-carboxamide

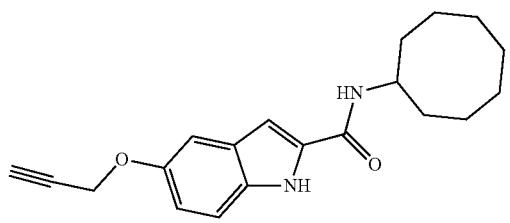 [SMILES: C#CCOc1ccc2[nH]c(C(=O)NC3CCCCCCC3)cc2c1]

$^1$H NMR (400 MHz, $CDCl_3$) δ=1.52-1.79 (m, 13H), 1.91-2.02 (m, 2H), 2.51 (s, 1H), 4.23 (sept, J=2 Hz, 1H), 4.72 (s, 2H), 6.07 (d, J=8 Hz, 1H), 6.74 (d, J=4 Hz, 1H), 7.00 (d, J=4 Hz, 1H), 7.16 (s, 1H), 7.35 (d, J=8 Hz, 1H), 9.45 (s, 1H); ESI-MS m/z: [M+Na]$^+$ calculated for $C_{20}H_{24}N_2NaO_2$: 347.2, found: 347.5.

Intermediate 2. 5-(prop-2-yn-1-yloxy)-N-((1S,2S,5R)-2,6,6-trimethylbicyclo[3.1.1]heptan-3-yl)-1H-indole-2-carboxamide

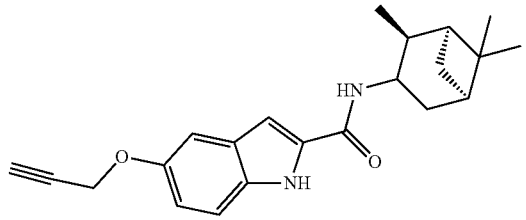 [SMILES: C#CCOc1ccc2[nH]c(C(=O)NC3C[C@H]4C[C@@H]([C@@H]3C)C4(C)C)cc2c1]

$^1$H NMR (400 MHz, $CDCl_3$) δ=0.95 (d, J=12 Hz, 1H), 1.14 (s, 3H), 1.20 (s, 3H), 1.28 (s, 3H), 1.67-1.72 (m, 1H), 1.90-1.97 (m, 2H), 2.02-2.06 (m, 1H), 2.47-2.54 (m, 2H), 2.71-2.79 (m, 1H), 4.54-4.62 (m, 1H), 4.74 (s, 2H), 6.10 (d, J=8 Hz, 1H), 6.82 (s, 1H), 7.01-7.04 (m, 1H), 7.18 (s, 1H), 7.40 (d, J=8 Hz, 1H), 9.84 (s, 1H); ESI-MS m/z: [M+H]$^+$ calculated for $C_{22}H_{27}N_2O_2$: 351.2, found: 351.4.

Intermediate 3. Methyl 4-(3-((3s,5s,7s)-adamantan-1-yl)ureido)-2-(prop-2-yn-1-yloxy)benzoate

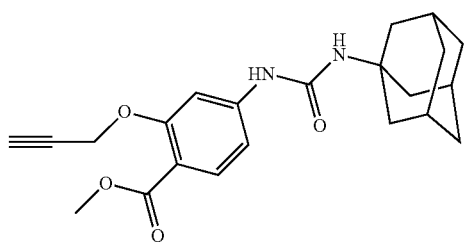 [SMILES: C#CCOc1cc(NC(=O)NC23CC4CC(CC(C4)C2)C3)ccc1C(=O)OC]

$^1$H NMR (400 MHz, CDCl$_3$) δ=1.67 (br, 6H), 2.01 (br, 6H), 2.08 (br, 3H), 2.52 (s, 1H), 3.91 (s, 3H), 4.69 (s, 2H), 6.85 (d, J=2 Hz, 1H), 6.98 (d, J=4 Hz, 1H), 7.07 (s, 1H), 7.69 (d, J=4 Hz, 1H), 10.84 (s, 1H) ESI-MS m/z: [M+H]$^+$ calculated for C$_{22}$H$_{26}$N$_2$NaO$_4$: 405.2, found: 405.4.

Example 2. General Procedures for Synthesis of Compounds 1-4

TAMRA- or BODIPY-linked azide (1 equiv.), alkyne intermediate (Intermediate 1, 2, or 3; 1.4 equiv.), sodium ascorbate (1.5 equiv.), CuSO$_4$ (1.2 equiv.) were dissolved in DMSO and stirred overnight in dark at room temperature. Cold water was added to the reaction mixture to precipitate product. After centrifugation, the pellet was washed with water and acetone to afford final product.

Compound 1. 5-((6-(4-(((2-(cyclooctylcarbamoyl)-1H-indol-5-yl)oxy)methyl)-1H-1,2,3-triazol-1-yl)hexyl)carbamoyl)-2-(3-(dimethyl-λ$^4$-azanylidene)-6-(dimethylamino)-3,10-dihydroanthracen-9-yl)benzoic acid

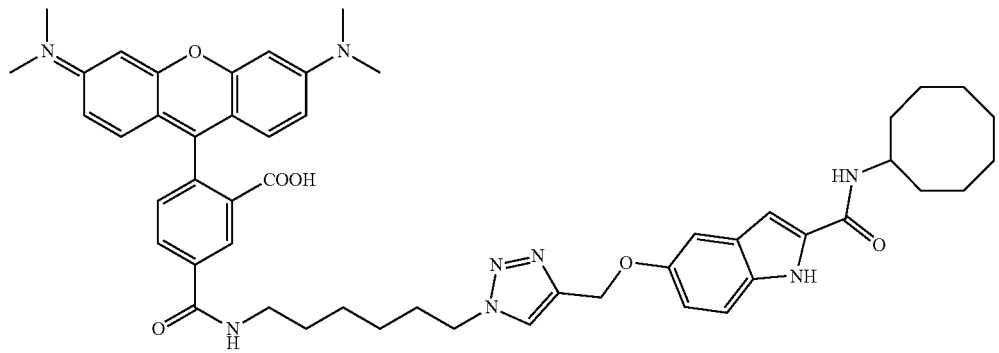

Yield: 96%; ESI-MS m/z: [M+Na]$^+$ calculated for C$_{51}$H$_{59}$N$_8$NaO$_6$: 902.4, found: 902.0; HPLC purity: 98.1%.

Compound 2. 2-(3-(dimethyl-λ$^4$-azanylidene)-6-(dimethylamino)-3,10-dihydroanthracen-9-yl)-5-((6-(4-(((2-(((1S,2S,5R)-2,6,6-trimethylbicyclo[3.1.1]heptan-3-yl)carbamoyl)-1H-indol-5-yl)oxy)methyl)-1H-1,2,3-triazol-1-yl)hexyl)carbamoyl)benzoic acid

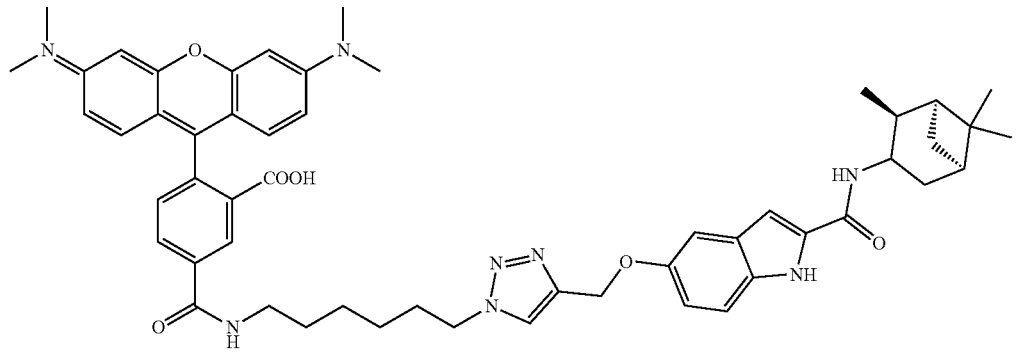

Yield: 97%; ESI-MS m/z: [M+H]$^+$ calculated for C$_{53}$H$_{62}$N$_8$O$_6$: 906.5, found: 906.3; HPLC purity: 97%.

Compound 3. N-cyclooctyl-5-((1-(3-(3-(5,5-difluoro-7,9-dimethyl-5H-5$\lambda^4$,6$\lambda^4$-dipyrrolo[1,2-c:2',1'-f][1,3,2]diazaborinin-3-yl)propanamido)propyl)-1H-1,2,3-triazol-4-yl)methoxy)-1H-indole-2-carboxamide Yield: 95%; ESI-MS m/z: [M+Na]$^+$ calculated for $C_{37}H_{45}BF_2N_8NaO_3$: 721.4, found: 721.7; HPLC purity: 96.6%

Compound 4. Methyl 4-(3-(((3s,5s,7s)-adamantan-1-yl)ureido)-2-((1-(3-(3-(5,5-difluoro-7,9-dimethyl-5H-5$\lambda^4$,6$\lambda^4$-dipyrrolo[1,2-c:2',1'-f][1,3,2]diazaborinin-3-yl)propanamido)propyl)-1H-1,2,3-triazol-4-yl)methoxy)benzoate Yield: 94.2%; ESI-MS m/z: [M+Na]$^+$ calculated for $C_{39}H_{47}BF_2N_8NaO_5$: 779.4, found: 779.7 [M+Na]$^+$; HPLC purity: 94.2%.

Example 3. Cross-Resistance Between MmpL3 Inhibitors

Figure 1:
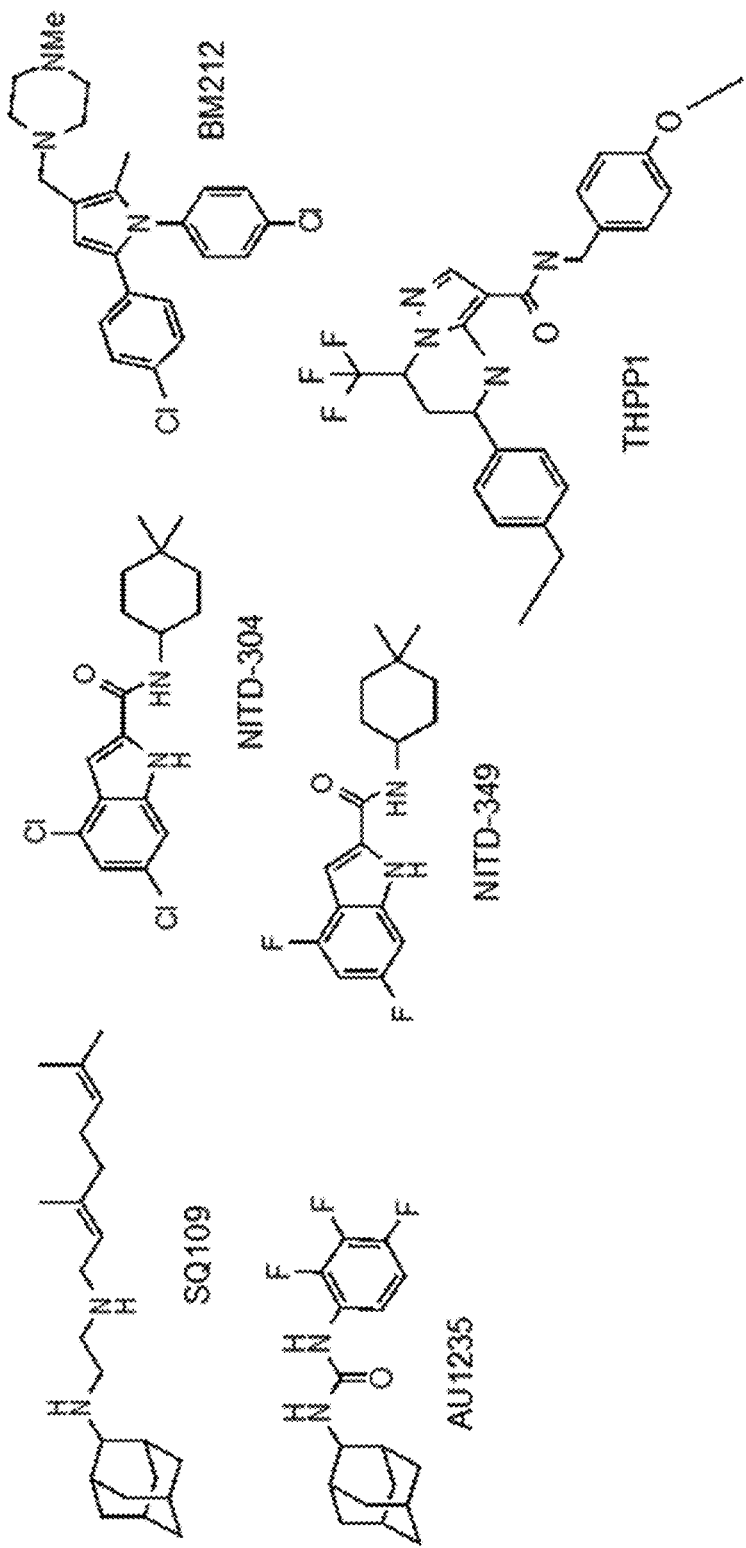
FIG. 1 shows chemical structures of six MmpL3 inhibitors as described herein.
Figure 2:
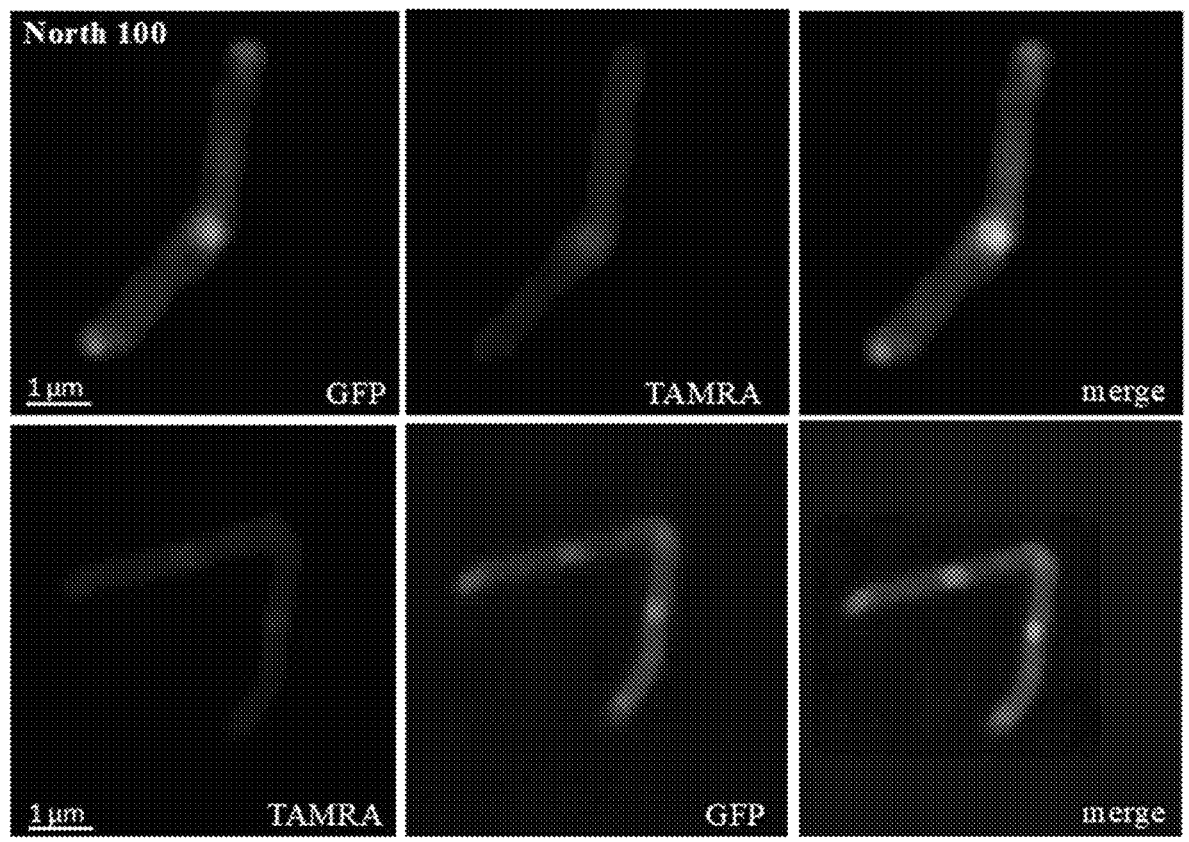
FIG. 2 shows co-localization of Compound 1 (i.e., North 100) with MmpL3tb-GFP at the old poles and septa of an *M. smegmatis* mmpL3 deletion mutant expressing an mmpL3tb-gfp fusion.

Six representative MmpL3 inhibitors were selected for this study, AU1235, SQ109, THPP1, BM212, NITD-304, and NITD-349. Structures of each inhibitor are shown in FIG. 1. Compounds AU1235, SQ109, THPP1, BM212 have been reported to inhibit the transfer of mycolic acids to their cell envelope acceptors in Mtb or *M. bovis* BCG (see e.g., Grzegorzewicz et al, *Nat. Chem. Biol.* 2012, 8:334-341; Tahlan et al, *Antimicrob. Agents Chemother.* 2012, 56:1797-1809; Remuinan et al, *PLoS ONE*, 2013, 8:e60933; and Cox et al, *Nat. Microbiol.* 2016, 1:15006). NITD-304 and NITD-349 displayed the same expected property of MmpL3 inhibitors, and was verified by metabolic labeling of Mtb H37Rv with [1,2-$^{14}$C]acetate upon treatment with increasing concentrations of the two compounds, as shown in FIGS. 9A-9B.

A number of mutations in mmpL3 were reported to increase the resistance of Mtb to one or more of the compounds listed above. To compare the level of resistance conferred by these mutations to each of the six compounds and delineate the regions of MmpL3 associated with cross-resistance, 77 different variants of the Mtb mmpL3 gene (mmpL3tb), including variants harboring missense mutations previously reported to confer resistance to the inhibitors listed above, were expressed in the background of a Msmg mmpL3 deletion mutant (MsmgΔmmpL3), and the resulting recombinant strains were tested for MICs against all six compounds. Of all the MmpL3tb variants tested, eleven increased at least 4-fold the level of resistance of the recombinant strains to one or more compounds. These variants are shown in Tables 1A-1B. With few exceptions, the variants conferred resistance to at least three out of the six compounds indicative of extensive cross-resistance between structurally unrelated chemotypes. The Q372R resistance mutation was found to be specific to the NITD compounds whereas F644C specifically impacted susceptibility to SQ109 and THPP1, and T311I only impacted the MICs of AU1235 and THPP1. The fewest resistance mutations were found for compound BM212.

MIC values in are in μg/mL. Results labeled "a" in Tables 1A-1B indicate an increase in MIC over MsmgΔmmpL3 expressing wild-type mmpL3tb of 8-fold or more; results labeled "b" indicate a 4-fold increase in MIC. No label indicates a maximum of 2-fold change in MIC which is considered within the experimental margin of error. The MICs of Compound 3 and Compound 4 against Msmg expressing WT mmpL3tb were 32 and 64 µg/mL, respectively.

TABLE 1A

Resistance Profile of Msmg mmpL3 Mutants Rescued with Mutated Variants of mmpL3tb

| Mutant | THPP1 | SQ109 | BM212 | AU1235 | NITD-304 | NITD-349 |
|---|---|---|---|---|---|---|
| MmpL3 WT | 2.5 | 0.39 | 6.25 | 0.39 | 0.06 | 0.06 |
| L189R | >50$^a$ | 3.13$^a$ | 12.5 | 1.56$^b$ | 0.25$^b$ | 0.25$^b$ |
| G253E | 10$^b$ | 1.25$^b$ | 12.5 | 3.13$^a$ | 0.4$^a$ | 0.4$^a$ |
| S288T | 6.25 | 3.13$^a$ | 25.0$^b$ | 12.5$^a$ | 0.32$^a$ | 0.64$^a$ |
| S309C | >50$^a$ | 6.25$^a$ | 12.5 | 3.13$^b$ | 0.25$^a$ | 0.5$^a$ |
| T311I | 10$^b$ | 0.78 | 12.5 | 1.56$^b$ | 0.06 | 0.125 |
| Q372R | 5 | 0.78 | 12.5 | 0.78 | 0.5$^a$ | 0.5$^a$ |
| L567P | 12.5$^b$ | 1.56$^b$ | 12.5 | 0.78 | 1$^a$ | 1$^a$ |
| S591I | >50$^a$ | 3.13$^a$ | 25.0$^b$ | 3.13$^a$ | 0.25$^a$ | 0.5$^a$ |
| F644C | >50$^a$ | 1.56$^b$ | 3.13 | 0.78 | 0.03 | 0.03 |
| V684G | 2.5 | 0.39 | 12.5 | 3.13$^a$ | 0.25$^b$ | 0.25$^b$ |
| V684A | 5 | 0.39 | 6.25 | 1.56$^b$ | 0.5$^a$ | 0.5$^a$ |

TABLE 1B

Resistance Profile of Msmg mmpL3 Mutants Rescued with Mutated Variants of mmpL3tb

| Mutant | North 4 | North 21 | Compound 1 | Compound 2 |
|---|---|---|---|---|
| MmpL3 WT | 0.16 | 0.05 | 8 | 4 |
| L189R | 1.28[a] | 0.2[b] | >32[b] | 8 |
| G253E | 1.28[a] | 0.2[b] | >32[b] | 8 |
| S288T | 1.28[a] | 0.2[b] | >32[b] | 4 |
| S309C | 1.28[a] | 0.2[b] | >32[b] | 8 |
| T311I | 0.08 | 0.05 | >32[b] | 4 |
| Q372R | 0.32 | 0.05 | >32[b] | 16[b] |
| L567P | 0.64[b] | 0.1 | 32[b] | 4 |
| S591I | 0.64[b] | 0.1 | >32[b] | 8 |
| F644C | 0.32 | 0.05 | 16 | 8 |
| V684G | 1.28[a] | 0.2[b] | >32[b] | 4 |
| V684A | 0.32 | 0.05 | >32[b] | 4 |

To further analyze the apparent lack of specificity of a number of resistance mutations, the nature of the mutations was modified at positions L189, G253, S591, F644 and V684 of MmpL3tb so as to change the size, polarity, and/or charge of these cross-resistance-associated residues; how these changes affected the MICs of each inhibitor was then analyzed. Amino acid changes introduced at positions 189, 591 and 644 of MmpL3tb restored the transporter's susceptibility to all inhibitor series, and compound-specific susceptibility patterns were observed in response to some of the mutations introduced at positions 253 (G253R and G253W) and 684 (V684W and V684I), as shown in Table 2.

The importance of a negative charge at position 253 (G253E) was noted for resistance to THPP1, SQ109, AU1235, and both indolecarboxamides, whereas a positive charge at position 189 (L189R) appeared to be necessary for resistance to the same inhibitors, as shown in Table 2. These results support the hypothesis that direct and specific interactions between the inhibitors and the side chains of some MmpL3 amino acid residues are critical to their activity.

TABLE 2

Effect of Modifying the Nature of the Amino Acid Residue at Positions of MmpL3tb Associated with Cross-Resistance on MICs (MIC values are in μg/mL; CIP, ciprofloxacin (control drug))

| Mutant | THPP1 | SQ109 | BM212 | AU1235 | NITD-304 | NITD-349 | CIP |
|---|---|---|---|---|---|---|---|
| L189R | >32 | 1.25-2.5 | 8 | 1.25 | 0.5 | 0.5 | 0.31 |
| LI89A | 8[c] | 0.31-0.62[c] | 8 | 0.62[c] | 0.12[c] | 0.12[c] | 0.31 |
| G253E | 8 | 1.25 | 8 | 5 | 0.5 | 0.5 | 0.31 |
| G253R | 2[c] | 0.31-0.62[c] | 8 | 0.62[c] | 0.12-0.25[c] | 0.12-0.25[c] | 0.31 |
| G253W | 2[d] | 0.15-0.3[d] | 8 | 2.5-5 | 0.25 | 0.5 | 0.31 |
| S591I | 8 | 1.25-2.5 | 16 | 2.5 | 0.25 | 0.12-0.25 | 0.31 |
| S591W | 2[c] | 0.31[c] | 4[c] | 0.62[c] | 0.06[c] | 0.06-0.12[c] | 0.31 |
| S591G | 1[c] | 0.31[c] | 1[c] | 0.31-0.62[c] | 0.06-0.12[c] | 0.06-0.12[c] | 0.31 |
| F644C/I/L | >32 | 0.62-1.25 | 4 | 0.62 | 0.02-0.06 | 0.03-0.06 | 0.31 |
| F644Y | 4[c] | 0.15-0.31[c] | 8 | 0.15[c] | 0.06 | 0.03 | 0.31 |
| V684G | 4 | 0.31-0.62 | 4 | 2.5 | 0.12-0.25 | 0.12-0.25 | 0.31 |
| V684A | 4 | 0.15-0.31 | 4 | 1.25 | 0.25 | 0.25 | 0.31 |
| V684I | 1[c] | 0.31-0.62 | 2 | 0.31[c] | 0.06[c] | 0.06[c] | 0.31 |
| V684W | 2[d] | 0.07-0.15[d] | 4 | 0.62 | 0.25 | 0.5 | 0.31 |
| MmpL3 WT | 2 | 0.31 | 4 | 0.31 | 0.06 | 0.06 | 0.31 |

Mutations in bold letters of Table 2 correspond to the original resistance mutations identified by whole genome sequencing of spontaneous resistant mutants. These are identical to the resistance mutations shown in Tables 1A-1B and are referred to as the parent mutants. Other mutations were generated for the purpose of this experiment and similarly expressed in the background of MsmgΔmmpL3 as described herein. Mutations that reverted the resistance phenotype of the parent mutants to at least three inhibitor series are labeled "c" in Table 2. Mutations that reverted the resistance phenotype of the parent mutants to no more than one or two inhibitors are labeled "d" in Table 2.

As shown in FIG. 10, all cross-resistance mutations mapped to the central region of transmembrane segments of MmpL3, thought to be important for proton translocation or proton-driven conformational changes in the transporter (see e.g., Belardinelli et al, *ACS Infect. Dis.* 2016, 2:702-713).

Accordingly, the majority of these mutations were found to negatively impact the transport activity of MmpL3, as evidenced by the slower growth of the mutants on agar medium and reduced rates of mycolic acid transfer to the cell wall, as shown in FIGS. 11A-11B. That the resistance phenotype associated with these mutations did not result from a significant increase in the level of expression of mmpL3tb in the mutants was verified by qRT-PCR, as shown in FIG. 12.

Collectively, these results support the hypothesis that MmpL3 inhibitors interact directly and with a relative specificity to a common transmembrane region of MmpL3tb that is critical to the activity of the transporter.

Example 4. Synthesis of IC and Urea-Based Inhibitor Probes and Evidence of Colocalization with MmpL3tb in Intact Cells Identification of a common inhibitor binding region in MmpL3tb next prompted the design of fluorescent inhibitor probes targeted to the same region of the transporter. Adamantyl urea-based (Compound 4) and indolecarboxamide-based probes (Compounds 1-3) harboring either tetramethylrhodamine (TAMRA) or BODIPY FL fluorophores were designed and synthesized as described in Example 2.

That all of the probes were on-target and thus displayed the expected inhibitory effect on the transfer of mycolic acids to trehalose dimycolate and arabinogalactan in intact MsmgΔmmpL3/pMVGH1-mmpL3tb cells was verified by metabolic labeling with [1,2-$^{14}$C]acetate, as shown in FIGS. 13A-13B. The same MmpL3tb mutations found to confer resistance to multiple series of compounds also increased resistance to the inhibitor probes Compound 1 and/or Compound 2 (see Table 1B) indicating that these probes should effectively compete with test inhibitors for the same binding region of MmpL3tb. Compound 3 and Compound 4 had too high MICs against MsmgΔmmpL3 expressing wild-type mmpL3tb to be tested against the mutants, as shown in Table 1B.

The TAMRA-labeled Compound 1 and Compound 2 probes were incubated with the Msmg strain MsmgΔmmpL3/pMVGH1-mmpL3tb-GFP expressing MmpL3tb C-terminally fused to GFP. As reported previously (see e.g., Carel et al, *PLoS ONE* 2014, 9:e97148), the MmpL3tb-GFP fusion protein concentrated at the old pole and septum of the cells with the greatest fluorescence intensity mapping to the septum, as shown in FIG. 2. Fluorescence microscopic analyses of MsmgΔmmpL3/pMVGH1-mmpL3tb-GFP cells labeled with Compound 1 and Compound 2 pointed to the colocalization of the probes with MmpL3tb-GFP, as shown in FIGS. 2 and 14. In contrast, no colocalization was observed when a TAMRA-labeled probe unrelated to MmpL3 inhibitors (TAMRA-Mannose) was used, as shown in FIG. 14.

Example 5. Evidence of Inhibitor Probe Binding to MmpL3tb In Vitro and Development of a Competition Binding Assay To directly assess the ability of Compounds 1, 2, and 4 to interact with purified MmpL3tb in vitro, the MmpL3tb and MmpL3tb-GFP proteins purified from the Msmg strains MsmgΔmmpL3/pMVGH1-mmpL3tb and MsmgΔmmpL3/pMVGH1-mmpL3tb-gfp, respectively, were bound to polystyrene particles as described above, and the particles were exposed to various concentrations of Compound 1, Compound 2 and Compound 4 for 15 min at room temperature. Flow cytometry analysis of the MmpL3tb- and MmpL3tb-GFP-coated particles revealed a concentration-dependent binding of all probes to the particles, as shown in FIGS. 3A and 15. Negligible probe binding was observed in the absence of MmpL3tb or MmpL3tb-GFP on the particles (i.e., both untreated particles and particles treated with the mouse anti-His IgG antibody only), on particles harboring the GFP protein alone, or when the TAMRA-mannose probe was used, as shown in FIG. 3A.

Having established that Compounds 1, 2, and 4 bind to purified MmpL3tb, a displacement analysis was performed to determine if displacement of Compound 2 would occur upon addition of increasing concentrations of each of the six prototypical inhibitors to the reaction mixture. As shown in FIG. 3B, a clear concentration-dependent displacement of Compound 2 by NITD-304, NITD-349, AU1235, BM212, and THPP1 was observed. The displacement was not significant for SQ109. Without being bound by theory, the residual binding of Compound 2 to MmpL3tb may be explained by the relatively high hydrophobicity of this probe, making it prone to accumulate in the hydrophobic environment of MmpL3tb. Whether due to a competition between the test inhibitors and the fluorescent probe for the same binding site on MmpL3tb, or to conformational changes in MmpL3tb induced by the test inhibitors (see e.g., Zhang et al, *Cell*, 2019, 176:636-648) reducing the affinity of the protein for the fluorescent probe, five out the six test compounds clearly proved capable of displacing Compound 2 in a concentration-dependent manner, indicative of a direct interaction with the mycolic acid transporter.

Example 6. Competition Binding Between MmpL3 Inhibitor and Inhibitor Probes in Intact Mycobacterial Cells The metabolic labeling of probe-treated MsmgΔmmpL3/pMVGH1-mmpL3tb cells (see FIGS. 13A-13B) and the colocalization of Compound 1 and Compound 2 with MmpL3tb-GFP in intact bacilli (see FIGS. 2 and 14) both indicating that the inhibitor probes reached their target in whole cells, the flow cytometry-based displacement assay was adapted as described above to intact cells to assess the assay in rapid screening of MmpL3tb inhibitors. Flow cytometry-based competition binding assays between Compound 2 or Compound 1 and MmpL3 inhibitors were performed using MsmgΔmmpL3/pMVGH1-mmpL3tb cells as a source of MmpL3tb target. Prior to performing these assays, it was verified by metabolic labeling with [1,2-$^{14}$C]acetate that BM212, THPP1, NITD-304, NITD-349 and SQ109 actually targeted MmpL3tb in the Msmg recombinant system, as shown in FIGS. 16A-16B. Targeting of AU1235 was previously reported (see e.g., Grzegorzewicz et al, *Nat. Chem. Biol.* 2012, 8:334-341).

Addition of increasing concentrations of the six prototypical compounds to MsmgΔmmpL3/pMVGH1-mmpL3tb cells previously labeled with either Compound 1 or Compound 2 revealed a concentration-dependent displacement of the probe by all six inhibitors that was not observed with the control drugs INH and RIF, as shown in FIG. 4.

Example 7. Detection of Inhibitor Binding to MmpL3 Using Biolayer Interferometry and Surface Plasmon Resonance As an alternative and more direct approach to monitor inhibitor binding to purified MmpL3tb, a biolayer interferometry (BLI) assay and a Surface Plasmon Resonance (SPR) assay were developed.

BLI Assay

MmpL3tb purified from Msmg was immobilized onto the surface of sensor tips and compound interaction with MmpL3tb was monitored by first dipping the sensors into microplate wells containing increasing concentrations of test compounds (association), followed by dipping into wells containing buffer alone (dissociation). The kinetics of compound binding and dissociation to MmpL3tb was monitored in real-time. Among the compounds tested, SQ109, North 4, and North 21 (structures shown below) consistently bound to MmpL3tb with the strongest signals, as shown in FIGS. 17A-17B. A weak binding signal was also detected for AU1235. BM212 is poorly soluble and only yielded weak binding signals. No signal was detected for THPP1, NITD-304 or NITD-349. It was also found that the fluorescence of Compound 1 and Compound 2 interferes with the BLI detection method; these probes could thus not be tested for binding using this method.

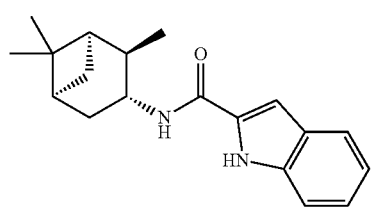

North 4

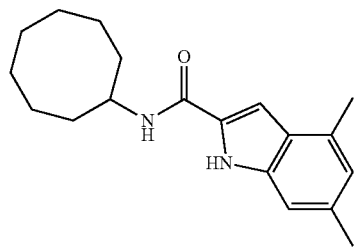

North 21

SPR Assay

Figure 5:
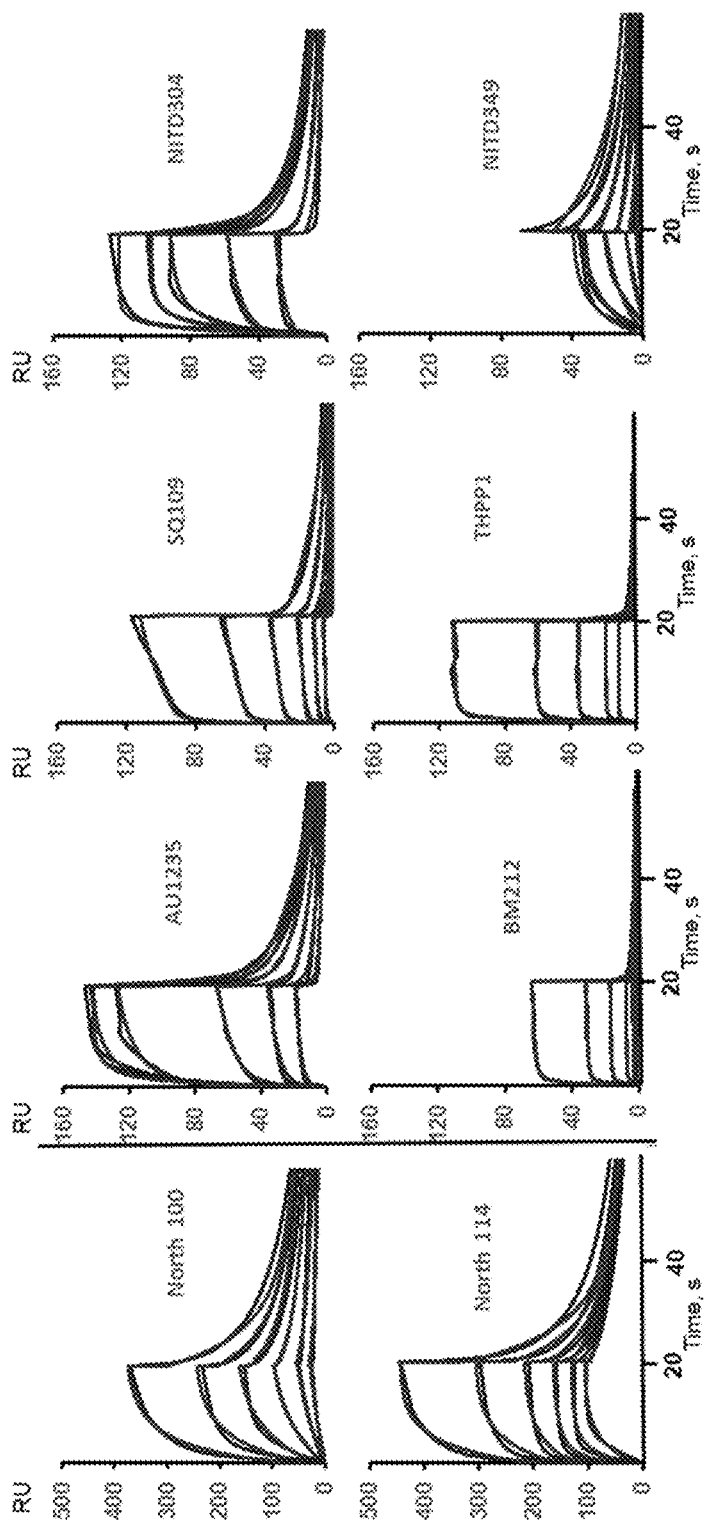
FIG. 5 shows direct interactions of inhibitors with MmpL3tb as measured by Surface Plasmon Resonance. MmpL3tb protein was immobilized at the density ~12,000 response units, (RU) and compounds were injected in HEPES-TX buffer supplemented with 5% DMSO at concentrations 1.625, 3.75, 7.5, 15, 30, 60 μM for BM212 and 12.5, 25, 50, 100, 200, 400 μM for the rest of compounds.

Purified MmpL3tb protein was immobilized onto the surface of CM5 chips and increasing concentrations of inhibitors were injected over the surface. Unlike BLI, SPR is insensitive to fluorescence and both Compounds 1-2 were included in the SPR experiments. All tested compounds were found to bind to MmpL3tb specifically, albeit with signals of different strengths and different apparent affinities, as shown in FIG. 5. Fitting the data into kinetic models yielded the on- and off-rates and the dissociation constants for each compound, as shown in Table 3.

TABLE 3

Global fit kinetic parameters describing interactions of inhibitors with the purified MmpL3tb protein

| | Kinetic parameters[a] | | | | | | |
|---|---|---|---|---|---|---|---|
| Inhibitor | ka1 (1/M*s) | kd1 (1/s) | ka2 (1/RU*s) | kd2 (1/s) | KD1 (mM) | KD2 (mM) | Model |
| SQ109 | 1208.2 | 2.32 | 0.025 | 0.0436 | 1.2122 | — | Two-state reaction |
| BM212 | 1054.8 | 1.67 | 0.005 | 0.0222 | 1.2884 | — | Two-state reaction |
| AU1235 | 1858.1 | 0.39 | 0.019 | 0.0316 | 0.1322 | — | Two-state reaction |
| THPP1 | 512.6 | 1.46 | 0.002 | 0.0233 | 2.6307 | — | Two-state reaction |
| NITD304 | 1953.6 | 0.26 | 0.013 | 0.0216 | 0.0825 | — | Two-state reaction |
| NITD349 | 426.1 | 0.06 | 0.005 | 0.0002 | 0.0054 | — | Two-state reaction |
| North100 | 2138.3 | 0.19 | 0.039 | 0.0273 | 0.0361 | — | Two-state reaction |
| North114 | 36380.1 | 0.02 | 540.582 | 0.1556 | 0.0005 | 0.288 | Heterogeneous ligand |

[a]Data were fit globally using the indicated models. ka1, ka2, kd1 and kd2 are microscopic rate constants; KD1 and KD2 are equilibrium dissociation constants calculated from the ratio of the dissociation and association rate constants.

With the exception of Compound 2, the best fit was found for the Two-State Reaction model that postulates a conformational change following inhibitor binding. Indeed, binding of small molecule inhibitors to large proteins such as immobilized MmpL3tb is unlikely to lead to large changes in mass. Hence, the strong SPR signals observed for Compound 1, Compound 2, AU1235, SQ109, NITD-304, and THPP1 are likely due to conformational changes in the transporter induced by the binding of these inhibitors, a hypothesis supported by the high-resolution crystal structure of MmpL3 from Msmg in complex with SQ109 and an indolecarboxamide inhibitor (see e.g., Zhang et al, Cell 2019, 176:636-648). The dissociation constants (KD) describing the binding of the inhibitors to MmpL3tb range from the low millimolar to low micromolar concentrations, with NITD-349, NITD-304, AU1235 and Compound 1 having the highest affinities to the transporter. Compound 2 presented a submicromolar affinity for one of the MmpL3tb states.

Example 8. Conformational Changes in MmpL3 Upon Inhibitor Binding

Assuming that the inhibition of MmpL3 by some of the test compounds results from conformational changes in the transporter upon inhibitor binding, it is possible that mutations conferring resistance to these inhibitors themselves alter the conformation of MmpL3 to protect its activity. Such mutations may either prevent the inhibitor from binding to MmpL3 or restore TMM export activity despite inhibitor-induced conformational changes. The G253E variant of MmpL3tb confers resistance to all prototypic inhibitors with the exception of BM212, as shown in Tables 1A-1B. This MmpL3tb variant was therefore purified and compared with the interactions of inhibitors with WT MmpL3tb versus MmpL3tb(G253E) by BL. Surprisingly, while no binding to MmpL3tb(G253E) was detected for SQ109 and North 21, the binding of North 4 to MmpL3tb was unaltered by the G253E mutation, as shown in FIGS. 17A-17B. No differences in BLI signals were observed for the other tested compounds. Thus, the G253E substitution specifically affects the interactions of some inhibitors with MmpL3tb.

To determine whether the binding of inhibitors and the G253E substitution affected the conformation of MmpL3tb, a partial proteolysis analysis was conducted. The purified parent and G253E MmpL3tb variants were treated with increasing concentrations of trypsin in the presence and absence of inhibitors. It was found that the proteolytic patterns of the WT and G253E variants differ from one another. The tryptic profiles of WT MmpL3tb comprise four fragments with approximate molecular masses of 78 kDa (band 1), 69 kDa (band 2), 65 kDa (band 3) and 59 kDa (band 4) that are reproducibly present on the gels, as shown in FIG. 6. The last three tryptic fragments are the most stable and accumulate at the highest concentration of trypsin (1 μg/mL). In contrast, in addition to the 69, 65, and 59 kDa fragments that are common with the WT, the proteolytic profiles of MmpL3tb(G253E) contain two unique bands with estimated molecular masses of 90 kDa (band 5) and 75 kDa (band 6). This result suggests that the G253E substitution stabilizes a different conformation of MmpL3tb, which could be contributing to changes in inhibitor binding and resistance.

The addition of a molar excess of inhibitors changed the relative amounts of tryptic fragments but not the proteolytic profiles of the MmpL3tb WT and G253E variants, as shown in FIGS. 6 and 18. This result was consistent with transient changes in MmpL3tb upon inhibitor binding and was in agreement with the fast on- and off kinetics of their interactions with the protein, as shown in FIGS. 5, 17A, and 17B.

Example 9. Effect of MmpL3 Inhibition Versus Inhibitors on the PMF of Mtb

The deleterious impact of MmpL3 inhibition on the PMF and energy production of mycobacterial cells has been suggested by two independent studies. Literature reports have shown that genetically silencing mmpL3 in Mtb leads to the repression of a number of genes involved in energy production, including atpB which encodes a component of the ATP synthase, and nuoB, nuoD and nuoH which encode subunits of the NADH dehydrogenase (see e.g., Degiacomi et al, *Sci. Rep.* 2017, 7:43495). Second was the observation that Msmg mutants resistant to a novel class of MmpL3 inhibitors and whose growth properties were consistent with reduced MmpL3 activity displayed a significantly higher membrane potential than their WT parent strain (see e.g., McNeil et al, *Microbiology,* 2017, 163:1065-1070). Since treating mycobacteria with some MmpL3 inhibitors has been reported to alter the transmembrane potential ($\Delta\Psi$), the transmembrane electrochemical proton gradient ($\Delta pH$) or both components of the PMF (see e.g., Li et al, *Antimicrob. Agents Chemother.* 2014, 58:6413-6423; Li et al, *J. Med. Chem.* 2014, 57:3126-3139; Feng et al, *Proc. Natl. Acad. Sci. USA* 2015, 112:E7073-7082; and Foss et al, *ACS Infect. Dis.* 2016, 2:500-508), these observations called into question whether the inhibitors were responsible for PMF dissipation (i.e., independent of their binding to MmpL3) as suggested in literature reports (see e.g., Li et al, *Antimicrob. Agents Chemother.* 2014, 58:6413-6423), or whether the impact on PMF was secondary to the inhibition of MmpL3.

To differentiate between these two hypotheses, the effect of genetically silencing mmpL3 on each of the two components of the PMF of Mtb was measured. A previously reported mmpL3 conditional knock-down, MmpL3-DUC, (see e.g., Li et al, *Antimicrob. Agents Chemother.* 2016, 60:5198-5207) was used to measure the impact of mmpL3 silencing on the $\Delta\Psi$ and $\Delta pH$ of Mtb by labeling with 3,3'-diethyloxacarbocyanine iodide [DiOC$_2$(3)] and 5-chloromethyl-fluorescein diacetate (CMFDA), respectively. While the progressive silencing of mmpL3 with increasing concentrations of anhydro-tetracycline (ATc) did not significantly impact the intracellular pH of the cells, a ATc concentration-dependent increase in $\Delta\Psi$ (up to two-fold above WT levels) was observed, which stabilized at ATc concentrations at and above 1 ng/mL, as shown in FIG. 7. Thus, the decrease in proton uptake associated with MmpL3-mediated substrate export that follows mmpL3 silencing leads to a significant increase in $\Delta\Psi$ in Mtb.

Next, the same labeling approach with the fluorescent dyes DiOC$_2$ and CMFDA was used to investigate the effect of all six MmpL3 inhibitors on the PMF of the same Mtb H37Rv mc$^2$6206 wild-type parent strain as above (rather than that of Msmg). Consistent with earlier findings in Msmg (see e.g., Li et al, *Antimicrob. Agents Chemother.* 2014, 58:6413-6423), SQ109 dissipated $\Delta\Psi$ in a concentration-dependent manner while BM212 only showed an effect on $\Delta\Psi$ at the highest concentration tested (8×MIC), and other MmpL3 inhibitors failed to show any effect at all at concentrations up to 20 times their MIC value, as shown in FIG. 8A. BM212 at 8×MIC and SQ109 at 4 and 20×MIC further collapsed $\Delta pH$ whereas other MmpL3 inhibitors showed no such effect in this assay, as shown in FIG. 8B. The effect of BM212 and SQ109 on $\Delta pH$ further reflected in a succinate-driven proton translocation assay with the fluorescent substrate ACMA (see e.g., Li et al, *J. Med. Chem.* 2014, 57:3126-3139) using Mtb H37Rv mc$^2$6206 inverted membrane vesicles (IMVs). It was found that AU1235 also collapsed $\Delta pH$ in this assay when used at 4-fold MIC concentration, as shown in FIG. 19A. Reasons why the effect of AU1235 on $\Delta pH$ was detected in the IMV assay but not in the assay using intact Mtb bacilli may be due to the inefficient or slow penetration of this compound inside cells, and to the relatively short time of exposure of intact bacilli to the inhibitor (30 min). Regarding the broad-spectrum uncoupling activity of SQ109, this inhibitor similarly dissipated the pH gradient of IMVs prepared from *E. coli* which are naturally devoid of MmpL3. BM212, AU1235 and the three other MmpL3 inhibitors, in contrast, showed no such activity, as shown in FIG. 19B.

Since the impact of BM212, AU1235, and SQ109 on PMF dissipation was (i) not shared by all classes of MmpL3 inhibitors and (ii) did not phenocopy the effect of silencing mmpL3 in Mtb, it was concluded that the observed effects of a subset of MmpL3 inhibitors on $\Delta\Psi$ and $\Delta pH$ was not consecutive to the suppression of MmpL3 activity but rather a consequence of secondary effects of these compounds on the bacilli.

As described throughout the Examples, multiple independent analyses, including direct detection of fluorescent and unlabeled inhibitor binding to purified MmpL3tb, colocalization of inhibitor probes and MmpL3tb in intact bacilli, comparative proteolysis of MmpL3 WT in the presence and absence of inhibitors, and in vitro and whole cell-based competition binding assays, point to the direct binding of all analyzed, structurally different, series of compounds to the transporter. BLI, SPR, and limited proteolysis of the MmpL3tb protein further point to conformational changes in the transporter as a result of the binding of most compounds.

The results described herein point to a direct mechanism of inhibition of MmpL3 by all compound series analyzed herein, whether or not the compounds display additional effects on PMF that potentiates their activity. The typical lipophilicity associated with MmpL3 inhibitors (see e.g., Li et al, *Front Microbiol.* 2018, 9:1547), which likely favors partitioning in the phospholipid bilayer where the compounds interact with MmpL3 (see e.g., Belardinelli et al, *ACS Infect. Dis.* 2016, 2:702-713; and Zhang et al, *Cell,*

2019, 176:636-648), is most probably a key driver of their efficacy. Given the vulnerability of MmpL3 (see e.g., Li et al, *Antimicrob. Agents Chemother.* 2016, 60:5198-5207), it is to be expected that compounds with even weak binding affinity to the transporter may still show potency, thereby explaining the bias of phenotypic screens toward hits targeting MmpL3 (see e.g., Goldman et al, *Tuberculosis,* 2013, 93:569-588). In addition, MmpL3 inhibition may mask potential secondary effects or targets of selected hits. That SQ109, BM212 and some THPP compounds show activity against non-replicating persistent Mtb bacilli (see e.g., Li et al, *Antimicrob. Agents Chemother.* 2014, 58:6413-6423), and that SQ109, BM212 and AU1235 dissipate one or both components of the PMF in Mtb (unlike most other MmpL3 inhibitors) are indications that these inhibitors target more than one aspect of the physiology of mycobacteria.

The specificity of a subset of resistance mutations for some compound series contrasts with the finding of a number of mutations conferring broad-spectrum resistance to chemically diverse inhibitors, as shown in Tables 1A-1B. In view of the conformational change induced by the G253E mutation (see FIG. 6), it is believed that some broad-spectrum resistance mutations may function to either restore TMM export to levels sufficient to sustain growth, or to simultaneously prevent multiple series of compounds from accessing their binding site on the transporter. Both hypotheses were supported by the BLI experiments, wherein the MmpL3tb G253E variant lost the ability to bind some inhibitors (e.g., North 21; SQ109) yet retained the ability to bind others (e.g., North 4) (see FIGS. 17A-17B) despite having become resistant to all of them. A further observation resulting from the analysis of PMF in a Mtb mmpL3 conditional knock-down was that mmpL3 silencing led to an increase in $\Delta\Psi$ [see FIG. 7].

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula I:

A-B-C or a salt thereof, wherein:
A is a fluorescent detectable moiety selected from the group consisting of:

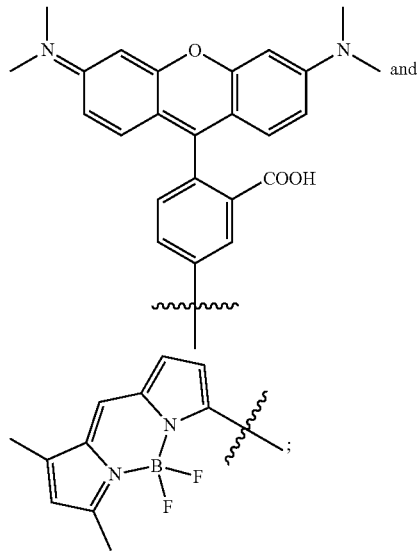

and

B is a linking group selected from the group consisting of:
—C(O)NH—(C$_{1-10}$ alkylene)-(5-6 membered heteroaryl)-(C$_{1-10}$ alkylene)-; and
—(C$_{1-10}$ alkylene)-C(O)NH—(C$_{1-10}$ alkylene)-(5-6 membered heteroaryl)-(C$_{1-10}$ alkylene)-; and
C is an MmpL3 inhibitor moiety selected from the group consisting of:

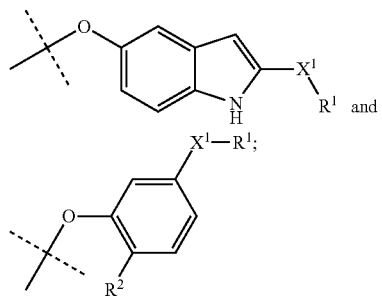

wherein:
X$^1$ is selected from the group consisting of C(O)NH and NHC(O)NH;
R$^1$ is C$_{5-10}$ cycloalkyl, which is optionally substituted by 1, 2, 3, or 4 independently selected C$_{1-4}$ alkyl groups; and
R$^2$ is C(O)C$_{1-4}$ alkoxy.

2. The compound of claim 1, or a salt thereof, wherein B is —C(O)NH—(C$_{1-10}$ alkylene)-(5-6 membered heteroaryl)-(C$_{1-10}$ alkylene)-.

3. The compound of claim 1, or a salt thereof, wherein the fluorescent detectable moiety is:

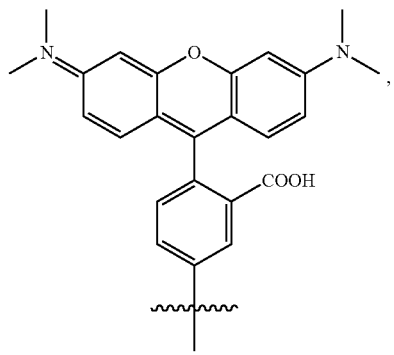

wherein ⁓⁓⁓ refers to the bond between A and B.

4. The compound of claim 1, or a salt thereof, wherein the fluorescent detectable moiety is:

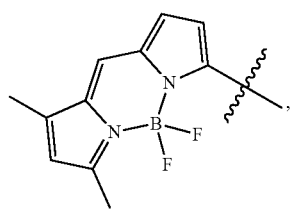

wherein ⁓⁓⁓ refers to the bond between A and B.

5. The compound of claim 1, or a salt thereof, wherein B is
—(C$_{1-10}$ alkylene)-C(O)NH—(C$_{1-10}$ alkylene)-(5-6 membered heteroaryl)-(C$_{1-10}$ alkylene)-.

6. The compound of claim 1, or a salt thereof, wherein B is a linking group selected from the group consisting of:
—C(O)NH—(C$_{1-6}$ alkylene)-(5-6 membered heteroaryl)-(C$_{1-3}$ alkylene)-; and
—(C$_{1-3}$ alkylene)-C(O)NH—(C$_{1-3}$ alkylene)-(5-6 membered heteroaryl)-(C$_{1-3}$ alkylene)-.

7. The compound of claim 1, or a salt thereof, wherein B is a linking group selected from the group consisting of:
—C(O)NHCH$_2$CH$_2$CH$_2$CH$_2$CH$_2$CH$_2$-triazolyl-CH$_2$—; and
—CH$_2$CH$_2$C(O)NHCH$_2$CH$_2$CH$_2$-triazolyl-CH$_2$—.

8. The compound of claim 1, or a salt thereof, wherein X$^1$ is C(O)NH.

9. The compound of claim 1, or a salt thereof, wherein X$^1$ is NHC(O)NH.

10. The compound of claim 1, or a salt thereof, wherein R$^1$ is C$_{5-10}$ cycloalkyl, which is optionally substituted by 1, 2, or 3 independently selected C$_{1-4}$ alkyl groups.

11. The compound of claim 1, or a salt thereof, wherein R$^1$ is selected from the group consisting of cyclooctyl, bicyclo[3.1.1]heptyl, and adamantyl, each of which is optionally substituted by 1, 2, or 3 methyl groups.

12. The compound of claim 1, or a salt thereof, wherein R$^2$ is C(O)OCH$_3$.

13. The compound of claim 1, or a salt thereof, wherein:
A is a fluorescent detectable moiety selected from the group consisting of:

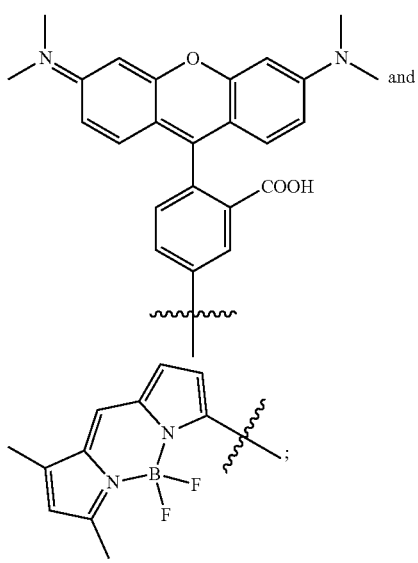

wherein ∿∿∿ refers to the bond between A and B;

B is a linking group selected from the group consisting of —C(O)NH—($C_{1-6}$ alkylene)-(triazolyl)-($C_{1-3}$ alkylene)- and —($C_{1-3}$ alkylene)-C(O)NH—($C_{1-3}$ alkylene)-(triazolyl)-($C_{1-3}$ alkylene)-; and C is an MmpL3 inhibitor moiety selected from the group consisting of:

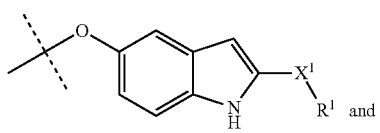

wherein:

------ refers to the bond between B and C;

$X^1$ is selected from the group consisting of C(O)NH and NHC(O)NH;

$R^1$ is selected from the group consisting of cyclooctyl, bicyclo[3.1.1]heptyl, and adamantyl, each of which is optionally substituted by 1, 2, or 3 methyl groups; and $R^2$ is C(O)OCH$_3$.

14. The compound of claim 1, or a salt thereof, wherein the compound of Formula I is a compound of Formula II, a compound of Formula III, or a compound of Formula IV:

II

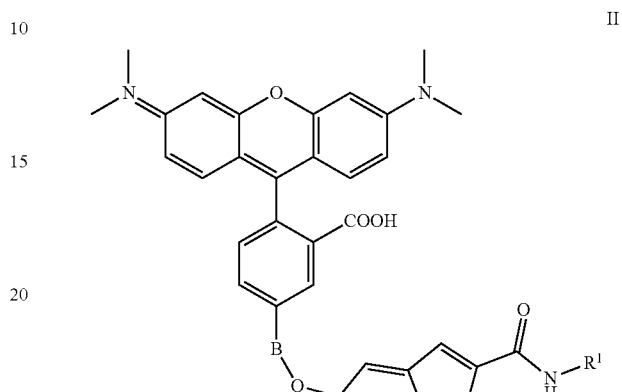

III

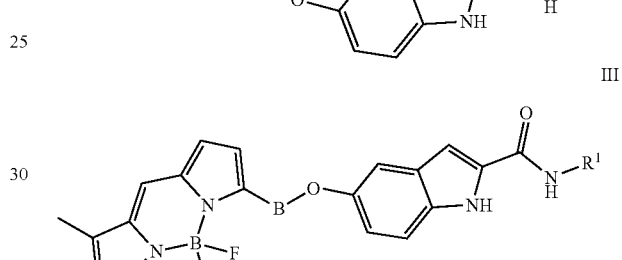

IV

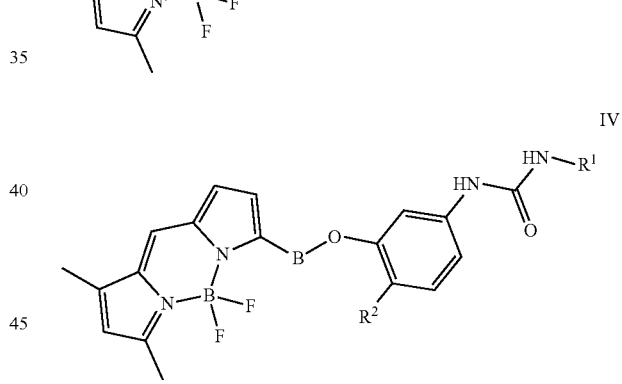

or a salt thereof.

15. The compound of claim 1, which is selected from the group consisting of:

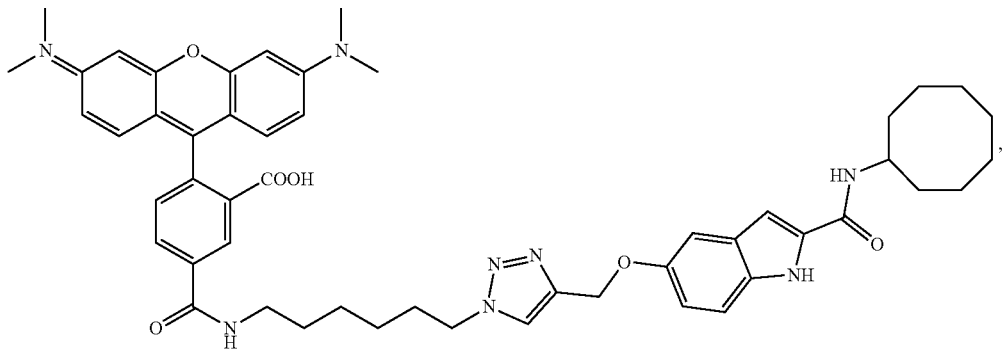

-continued

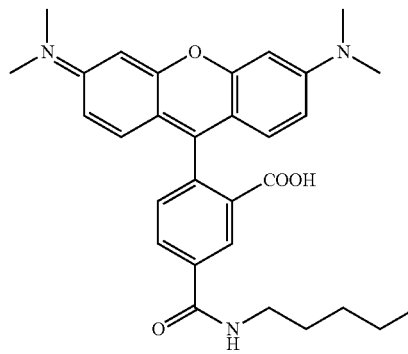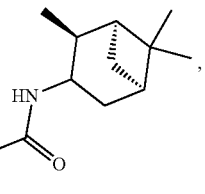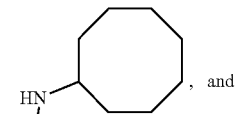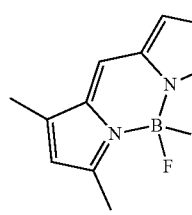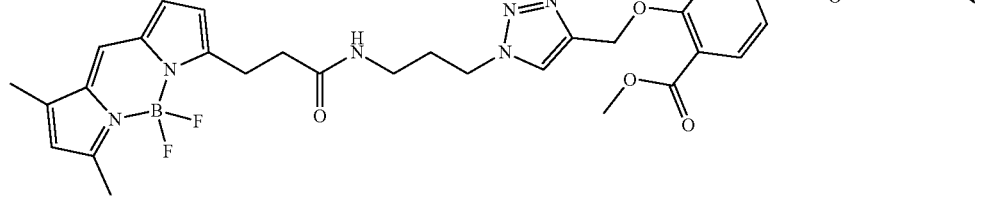

or a salt thereof.

16. A composition, comprising a compound of claim 1, or a salt thereof, and a carrier.

17. A method of identifying an inhibitor of MmpL3, comprising:
  i) contacting a cell with a compound of claim 1, or a salt thereof, to form a compound-MmpL3 complex in the cell;
  ii) contacting the cell with a test compound; and
  iii) measuring displacement of the compound from the compound-MmpL3 complex and formation of a test compound-MmpL3 complex in the cell.

\* \* \* \* \*

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: PCR primer sequence

<400> SEQUENCE: 1
cgtgttctcc gacctggtga tg                                              22

<210> SEQ ID NO 2
<211> LENGTH: 19
<212> TYPE: DNA
<213> ORGANISM: Artificial Sequence
<220> FEATURE:
<223> OTHER INFORMATION: PCR primer sequence

<400> SEQUENCE: 2
gcttgcgctc gtcgggcag                                                  19

<210> SEQ ID NO 3
<211> LENGTH: 20
<212> TYPE: DNA
<213> ORGANISM: Artificial Sequence
<220> FEATURE:
<223> OTHER INFORMATION: PCR primer sequence

<400> SEQUENCE: 3
cggtgcacat ggtcgaggtg                                                 20

<210> SEQ ID NO 4
<211> LENGTH: 20
<212> TYPE: DNA
<213> ORGANISM: Artificial Sequence
<220> FEATURE:
<223> OTHER INFORMATION: PCR primer sequence

<400> SEQUENCE: 4
tcgtcgccga tggtctggtc                                                 20